US008071747B2

(12) United States Patent
Skeiky et al.

(10) Patent No.: US 8,071,747 B2
(45) Date of Patent: Dec. 6, 2011

(54) FUSION PROTEINS OF MYCOBACTERIUM TUBERCULOSIS

(75) Inventors: Yasir Skeiky, Bellevue, WA (US); Steven Reed, Bellevue, WA (US); Mark Alderson, Bainbridge Island, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 12/490,272

(22) Filed: Jun. 23, 2009

(65) Prior Publication Data

US 2010/0015096 A1 Jan. 21, 2010

Related U.S. Application Data

(63) Continuation of application No. 11/418,848, filed on May 5, 2006, now Pat. No. 7,976,844, which is a continuation of application No. 09/886,349, filed on Jun. 20, 2001, now Pat. No. 7,083,796, which is a continuation-in-part of application No. 09/597,796, filed on Jun. 20, 2000, now Pat. No. 7,186,412, which is a continuation-in-part of application No. 09/287,849, filed on Apr. 7, 1999, now Pat. No. 6,627,198, which is a continuation-in-part of application No. 09/223,040, filed on Dec. 30, 1998, now Pat. No. 6,544,522.

(60) Provisional application No. 60/265,737, filed on Feb. 1, 2001, provisional application No. 60/158,338, filed on Oct. 7, 1999, provisional application No. 60/158,425, filed on Oct. 7, 1999.

(51) Int. Cl.
C07H 21/04 (2006.01)
C07H 21/02 (2006.01)
A61K 39/04 (2006.01)

(52) U.S. Cl. .................. 536/23.7; 536/23.1; 424/248.1; 424/234.1; 424/185.1; 424/184.1

(58) Field of Classification Search ................ 536/23.1, 536/23.7; 424/184.1, 185.1, 234.1, 248.1
See application file for complete search history.

(56) References Cited

U.S. PATENT DOCUMENTS

| | | |
|---|---|---|
| 3,943,119 A | 3/1976 | Tsumita et al. |
| 4,235,877 A | 11/1980 | Fullerton |
| 4,436,727 A | 3/1984 | Ribi |
| 4,603,112 A | 7/1986 | Paoletti et al. |
| 4,689,397 A | 8/1987 | Shinnick et al. |
| 4,751,180 A | 6/1988 | Cousens et al. |
| 4,769,330 A | 9/1988 | Paoletti et al. |
| 4,777,127 A | 10/1988 | Suni et al. |
| 4,866,034 A | 9/1989 | Ribi |
| 4,876,089 A | 10/1989 | Luciw et al. |
| 4,877,611 A | 10/1989 | Cantrell |
| 4,879,213 A | 11/1989 | Fox et al. |
| 4,897,268 A | 1/1990 | Tice et al. |
| 4,912,094 A | 3/1990 | Myers et al. |
| 4,935,233 A | 6/1990 | Bell et al. |
| 4,946,778 A | 8/1990 | Ladner et al. |
| 4,952,395 A | 8/1990 | Shinnick et al. |
| 5,108,745 A | 4/1992 | Horwitz |
| 5,145,684 A | 9/1992 | Liversidge et al. |
| 5,240,856 A | 8/1993 | Goffe et al. |
| 5,330,754 A | 7/1994 | Kapoor et al. |
| 5,466,468 A | 11/1995 | Schneider et al. |
| 5,478,726 A | 12/1995 | Shinnick et al. |
| 5,504,005 A | 4/1996 | Bloom et al. |
| 5,543,158 A | 8/1996 | Gref et al. |
| 5,565,213 A | 10/1996 | Nakamori et al. |
| 5,567,434 A | 10/1996 | Szoka |
| 5,580,579 A | 12/1996 | Ruddy et al. |
| 5,583,112 A | 12/1996 | Kensil et al. |
| 5,599,545 A | 2/1997 | Stanford et al. |
| 5,616,500 A | 4/1997 | Steinert et al. |
| 5,639,653 A | 6/1997 | Bloom et al. |
| 5,714,593 A | 2/1998 | Laqueyrerie et al. |
| 5,780,045 A | 7/1998 | McQuinn |
| 5,783,386 A | 7/1998 | Jacobs, Jr. et al. |
| 5,795,587 A | 8/1998 | Gao et al. |
| 5,804,212 A | 9/1998 | Illum |
| 5,811,128 A | 9/1998 | Tice et al. |
| 5,814,344 A | 9/1998 | Tice et al. |
| 5,817,473 A | 10/1998 | Das et al. |
| 5,820,883 A | 10/1998 | Tice et al. |
| 5,853,763 A | 12/1998 | Tice et al. |
| 5,856,462 A | 1/1999 | Agrawal |
| 5,928,647 A | 7/1999 | Rock |
| 5,942,252 A | 8/1999 | Tice et al. |
| 5,955,077 A | 9/1999 | Andersen et al. |
| 5,985,287 A | 11/1999 | Tan et al. |
| 6,001,361 A | 12/1999 | Tan et al. |

(Continued)

FOREIGN PATENT DOCUMENTS

EP 345242 12/1989

(Continued)

OTHER PUBLICATIONS

Carter, P. and Wells, J., "Dissecting the catalytic triad of a serine protease," *Nature*, vol. 322, pp. 564-568 (Apr. 1988).
Cole, et al. "Deciphering the biology of *Mycobacterium tuberculosis* from the complete genome sequence"; *Nature*, vol. 393, pp. 537-544 (Jun. 1998).
Collins, F.M. "New Generation of Tuberculosis Vaccines," 2001, Clinical Microbiology Newsletter, vol. 23, No. 3, pp. 17-23.
Content, et al., "The Genes Coding for the Antigen 85 Complexes of *Mycobacterium tuberculosis* and *Mycobacterium bovis* BCG Are Members of a Gene Family: Cloning, Sequence Determination, and Genomic Organization of the Gene Coding for Antigen 85-C of *M. tuberculosis*"; *Infection and Immunity*, vol. 59(9), pp. 3205-3212 (Sep. 1991).
Labouesse, B., et al., "Conformational changes in enzyme catalysis," *Biochemistry*, vol. 48, pp. 2137-2145 (1962).

(Continued)

Primary Examiner — Rodney P. Swartz
(74) Attorney, Agent, or Firm — Convergent Law Group LLP

(57) ABSTRACT

The present invention relates to compositions and fusion proteins containing at least two *Mycobacterium* sp. antigens, and nucleic acids encoding such compositions and fusion proteins. The compositions of the invention increase serological sensitivity of sera from individuals infected with tuberculosis, and methods for their use in the diagnosis, treatment, and prevention of tuberculosis infection.

48 Claims, 9 Drawing Sheets

U.S. PATENT DOCUMENTS

| | | | |
|---|---|---|---|
| 6,034,218 A | 3/2000 | Reed et al. | |
| 6,037,135 A | 3/2000 | Kubo et al. | |
| 6,113,918 A | 9/2000 | Johnson et al. | |
| 6,290,969 B1 | 9/2001 | Reed et al. | |
| 6,338,852 B1 | 1/2002 | Reed et al. | |
| 6,350,456 B1 | 2/2002 | Reed et al. | |
| 6,355,257 B1 | 3/2002 | Johnson et al. | |
| 6,458,366 B1 | 10/2002 | Reed et al. | |
| 6,465,633 B1 | 10/2002 | Skeiky | |
| 6,544,522 B1 | 4/2003 | Skeiky et al. | |
| 6,555,653 B2 | 4/2003 | Alderson et al. | |
| 6,592,877 B1 | 7/2003 | Reed et al. | |
| 6,613,881 B1 | 9/2003 | Alderson et al. | |
| 6,627,198 B2 | 9/2003 | Reed et al. | |
| 6,949,246 B2 | 9/2005 | Reed et al. | |
| 6,962,710 B2 | 11/2005 | Reed et al. | |
| 6,977,069 B2 | 12/2005 | Reed et al. | |
| 7,026,465 B2 | 4/2006 | Skeiky et al. | |
| 7,064,195 B2 | 6/2006 | Skeiky et al. | |
| 7,083,796 B2 | 8/2006 | Skeiky et al. | |
| 7,087,713 B2 | 8/2006 | Campos-Neto et al. | |
| 7,122,196 B2 | 10/2006 | Reed et al. | |
| 7,186,412 B1 | 3/2007 | Skeiky et al. | |
| 7,261,897 B2 | 8/2007 | Skeiky et al. | |
| 7,311,922 B1 | 12/2007 | Skeiky et al. | |
| 7,335,369 B2 | 2/2008 | Reed et al. | |
| 7,678,375 B2 | 3/2010 | Skeiky et al. | |
| 7,691,993 B2 | 4/2010 | Skeiky et al. | |
| 2006/0193876 A1 | 8/2006 | Skeiky et al. | |
| 2007/0054336 A1 | 3/2007 | Campos-Neto et al. | |
| 2007/0141087 A1 | 6/2007 | Reed et al. | |
| 2008/0176798 A1 | 7/2008 | Campos-Neto et al. | |
| 2008/0199405 A1 | 8/2008 | Reed et al. | |
| 2008/0269151 A1 | 10/2008 | Skeiky et al. | |
| 2008/0317716 A1 | 12/2008 | Skeiky et al. | |
| 2009/0017077 A1 | 1/2009 | Reed et al. | |
| 2009/0018095 A1 | 1/2009 | Skeiky et al. | |
| 2009/0022742 A1 | 1/2009 | Campos-Neto et al. | |
| 2009/0281168 A1 | 11/2009 | Reed et al. | |
| 2009/0306195 A1 | 12/2009 | Skeiky et al. | |
| 2010/0015096 A1 | 1/2010 | Skeiky et al. | |
| 2010/0183657 A1 | 7/2010 | Skeiky et al. | |
| 2010/0183677 A1 | 7/2010 | Skeiky et al. | |

FOREIGN PATENT DOCUMENTS

| | | |
|---|---|---|
| EP | 419355 | 3/1991 |
| EP | 519218 | 12/1992 |
| FR | 2244539 | 4/1975 |
| FR | 2265402 | 10/1975 |
| GB | 2200651 | 8/1988 |
| GB | 2298862 | 9/1996 |
| HU | 158035 | 3/1971 |
| RU | 2024021 | 11/1994 |
| WO | WO 88/05823 | 8/1988 |
| WO | WO 88/06591 | 9/1988 |
| WO | WO 89/01973 | 3/1989 |
| WO | WO 89/06280 | 7/1989 |
| WO | WO 91/02805 | 3/1991 |
| WO | WO 91/04272 | 4/1991 |
| WO | WO 91/14448 | 10/1991 |
| WO | WO 91/18926 | 12/1991 |
| WO | WO 92/04049 | 3/1992 |
| WO | WO 92/07243 | 4/1992 |
| WO | WO 92/14154 | 8/1992 |
| WO | WO 92/14823 | 9/1992 |
| WO | WO 92/16628 | 10/1992 |
| WO | WO 92/21697 | 12/1992 |
| WO | WO 92/21758 | 12/1992 |
| WO | WO 94/00153 | 1/1994 |
| WO | WO 94/00228 | 1/1994 |
| WO | WO 94/00492 | 1/1994 |
| WO | WO 94/00493 | 1/1994 |
| WO | WO 94/14069 | 6/1994 |
| WO | WO 94/20078 | 9/1994 |
| WO | WO 94/23701 | 10/1994 |
| WO | WO 95/01440 | 1/1995 |
| WO | WO 95/01441 | 1/1995 |
| WO | WO 95/14713 | 6/1995 |
| WO | WO 95/17210 | 6/1995 |
| WO | WO 95/17511 | 6/1995 |
| WO | WO 95/31216 | 11/1995 |
| WO | WO 96/02555 | 2/1996 |
| WO | WO 96/06638 | 3/1996 |
| WO | WO 96/15241 | 5/1996 |
| WO | WO 96/23885 | 8/1996 |
| WO | WO 96/28551 | 9/1996 |
| WO | WO 96/33739 | 10/1996 |
| WO | WO 96/38591 | 12/1996 |
| WO | WO 97/09248 | 3/1997 |
| WO | WO 97/09249 | 3/1997 |
| WO | WO 97/09428 | 3/1997 |
| WO | WO 97/09429 | 3/1997 |
| WO | WO 97/24447 | 10/1997 |
| WO | WO 98/07868 | 2/1998 |
| WO | WO 98/16645 | 4/1998 |
| WO | WO 98/16646 | 4/1998 |
| WO | WO 98/44119 | 10/1998 |
| WO | WO 98/53075 | 11/1998 |
| WO | WO 98/53076 | 11/1998 |
| WO | WO 99/09186 | 2/1999 |
| WO | WO99/33488 | 7/1999 |
| WO | WO 99/42076 | 8/1999 |
| WO | WO 99/42118 | 8/1999 |
| WO | WO 99/51748 A2 | 10/1999 |
| WO | WO 99/52549 | 10/1999 |
| WO | WO 00/09159 | 2/2000 |
| WO | WO 01/24820 A1 | 4/2001 |
| WO | WO 01/34802 A2 | 5/2001 |
| WO | WO 01/34803 | 5/2001 |
| WO | WO 01/51633 A2 | 7/2001 |
| WO | WO 01/62893 | 8/2001 |
| WO | WO 01/73032 A2 | 10/2001 |
| WO | WO 01/90152 | 11/2001 |
| WO | WO 01/90152 A2 | 11/2001 |
| WO | WO 01/98460 A2 | 12/2001 |
| WO | WO 2005/076101 | 8/2005 |
| WO | WO 2008/107370 | 9/2008 |

OTHER PUBLICATIONS

Skeiky, Y., et al., "Cloning, Expression, and Immunological Evaluation of Two Putative Secreted Serine Protease Antigens of *Mycobacterium tuberculosis*," Infection and Immunity, vol. 67(8), pp. 3998-4007 (Aug. 1999).

Verbon, et al., "The 14,000-Molecular-Weight Antigen of *Mycobacterium tuberculosis* Is Related to the Alpha-Crystallin Family of Low-Molecular-Weight Heat Shock Proteins"; *Journal of Bacteriology*, vol. 174(4), pp. 1352-1359 (Feb. 1992).

Wang, et al., "A novel method for increasing the expression level of recombinant proteins," *Protein Expression and Purification*, vol. 30(1), pp. 124-133 (Jul. 2003).

Altschul, et al., "Gapped BLAST and PSI-BLAST: a new generation of protein database search programs," Nuc. Acids Res. (25):3389-3402 (1977).

Alderson, et al., "Expression Cloning of an Immunodominant Family of *Mycobacterium tuberculosis* Antigens Using Human Cd4+ T Cells," J. Exp. Med. 191(3): 551-559 (2000).

Andersen and Hansen, "Structure and Mapping of Antigenic Domains of Protein Antigen b, a 38,000-Molecular-Weight Protein of *Mycobacterium tuberculosis*," Infection and Immunity 37(8):2481-2488 (1989).

Andersen and Heron, "Specificity of a Protective Memory Immune Response against *Mycobacterium tuberculosis*," Infection and Immunity 61(3):844-851 (1993).

Andersen, "Effective Vaccination of Mice against *Mycobacterium tuberculosis* Infection with a Soluble Mixture of Secreted Mycobacterial Proteins," Infection and Immunity 62(6):2536-2544 (1994).

Andersen, et al., "Identification of Immunodominant Antigens of *Mycobacterium tuberculosis*," Scand. J. Immunol 6:823-831 (1992).

Andersen, et al., "The T Cell Response to Secreted Antigens and *Mycobacterium tuberculosis*," Immunobiol 191:537-547 (1994).

Fsihi, et al. "The Mycrobacterium Leprae genome: systematic sequence ananlysis identifies key catabolic enzymes, ATPdependaent transport system and a novel PoIA locus associated with genomic variability," Molecular Microbiology 16(5):909-919 (1995).

Arnon, "Synthetic Peptides as a Basis for Vaccine Design," Molecular Immunology 28(2):209-215 (1991).

Ausubel, et al., "Isolation of Proteins for Microsequence Analysis," Current Protocols in Molecular Biology, Wiley & Sons, NY, pp. 10.19.1-10.19.12 (1993).

Banchereau, et al., "Dendritic cells and the control of immunity," Nature 392:245-251 (1998).

Barnes, et al., "Immunoreactivity of a 10-kDa Antigen of *Mycobacterium tuberculosis*," J. of Immunology 148(6):1835-1840 (1992).

Barrera, et al., Humoral Response to *Mycobacterium tuberculosis* in Patients with Human Immunodeficienty Virus Infection Tuberde and Lung Disease 73(4):187-91 (1992).

Batzer, et al., "Enhances evolutionary PCR using oligonucleotides with inosine at the 3' terminus" Nuc. Acids Res. 19:5081 (1991).

Berkner, "Development of Adenovirus Vectors for the Expression of Heterologous Genes," Biotechniques 6:616-627 (1988).

Boesen et al., "Human T-Cell Responses to Secreted Antigen Fractions of *Mycobacterium tuberculosis*," Infection and Immunity 63(4):1491-1497 (1995).

Borremans et al., "Cloning, Sequencing Determination, and Expression of a 32-Kilodalton-Protein Gene of *Mycobacterium tuberculosis*," Infection and Immunity 57(10):3123-3130 (1989).

Bowie, et al., "Deciphering the Message of Protein Sequences: Tolerance to Amino Acid Substitutions" Science 257-1306-10 (1990).

Brandt, et al., "ESAT-6 subunit vaccination against *Mycobacterium tuberculosis*," Infection and Immunity 68(2):791-795 (2000).

Brandt, et al., "The Protective Effect of the *Mycobacterium bovis* BCG Vaccine is Increased by Coadministration with the *Mycobacterium tuberculosis* 72-Kilodalton Fusion Polyprotein Mtb72F in *M. tuberculosis*-Infected Guinea Pigs" Infection and Immunity 72(11):6622-32 (2004).

Burgess, et al. "Possible Dissociation of the Heparin-binding and Mitogenic Activities of Heparin-Binding (Acidic Fibroblast) Growth Factor-1 from its Receptor-binding Activities by Site-Directed Mutagenesis of a Single Lysine Residue" J. Cell. Biol. 111:2129-2138 (1990).

Cameron, et al., "Identification and characterization of a putative serine protease expressed in vivo by *Mycobacterium avium* subsp. Paratuberculosisi," Microbiology 140( 8):1977-1982 (1994).

Campos-Neto, et al., "Cutting Edge: CD40 Ligand Is Not Essential for the Development of Cell-Mediated Immunity and Resistance to *Mycobacterium tuberculosis*," J. Immunol. 160(5): 2037-2041 (1988).

Carter, "Peptide Analysis Protocols," Methods in Molecular Biology, Chapter 1.1, 36:193-206 (1994).

Chaitra, et al., "Defining putative T cell epitopes from PE and PPE families of protein of *M. tuberculosis* with vaccine potential" Vaccine 23(10):1265-72 (2005).

Chaitra, et al., "HLA A0201-restricted cytotoxic T-cell epitopes in three PE/PPE family proteins of *M. tuberculosis*" Scand. J. of Immunology 67(4):411-17 (2008).

Chan and Kaufmann, Tuberculosis: Pathogenesis, Protection and Control, Chap. 24, ASM Press (1994).

Chen, et al., "T Cells for Tumor Therapy can be Obtained from Antigen-loaded Sponge Implants" Cancer Res. 54: 1065-1070 (1994).

Cirillo, et al., "Isolation and characterization of the aspartokinase and aspartate semialdehyde dehydrogenase operon from mycobacteria," Molecular Microbiology 11(4): 629-639 (1994).

Cohen, "Naked DNA Points Way to Vaccines" Science 259: 1691-1692 (1993).

Colbere-Garapin, et al., "A New Dominant Hybrid Selective Marker for Higher Eucaryotic Cells," J. Mol. Biol. 150:1-14 (1981).

Coler, et al. "Molecular cloning and immunologic reactivity of a novel low molecular mass antigen for *Mycobacterium tuberculosis*," J. Immunol. 161(5):2356-2364 (1998).

Coombes, et al., "Single dose, polymeric, microparticle-based vaccines: the influence of formulation conditions on the magnitude and duration of the immune response to a protein antigen," Vaccine 14: 1429-1438 (1996).

Coruzzi, et al., "Tissue-specific and light-regulated expression of a pea nuclear gene encoding the small subunit of ribulose-1,5-biphosphate carboxylase," EMBO 3: 1671-1680 (1984).

Creighton, Protein Structure: A Practical Approach, pp. 184-186 (1989).

Creighton, Proteins: Structures and Molecular Properties, pp. 314-315 (1984).

Daleine, et al., "Preliminary evaluation of a *Mycobacterium tuberculosis* lipoligosaccharide (LOS) antigen in the serological diagnosis of tuberculosis in HIV seropositive and seronegative patients," Tuberde and Lung Disease, 76( 3): 234-39 (1995).

Devereaux, et al., "A Comprehensive System of Sequence Analysis Tools for the VAX," Nuc. Acids Res. 12: 387-395 (1984).

Dillon, et al., "Molecular Characterization and Human T-Cell Responses to a Member of Novel *Mycobacterium tuberculosis* mtb39 Gene Family," Infection and Immunity 67( 6): 2941-2950 (1999).

Doran, et al., "Characertisation of a Novel Repetitive DNA sequence from *Mycrobacerium bovis*," FEMS Microbiology Letters 96: 179-186 (1992).

Eiglmeier, et al., "Use of an ordered cosmid library to deduce the genomic organization of *Mycobacterium leprae*," Mol. Microbiol. 7(2):197-206 (1993).

Fifis, et al., "Purification and Characterization of Major Antigens from a *Mycobacterium bovis* Culture Filtrate," Infection and Immunity 59(3):800-807 (1991).

Fisher-Hoch, et al., "Protection of rhesus monkey from fatal Lassa fever by vaccination with a recombinant vaccinia virus containing the Lassa virus glycoprotein gene" PNAS USA 86: 317-321 (1989).

Flexner, et al., "Vaccinia Virus Expression Vectors" Vaccine 8:17-21 (1989).

Flexner, "Attenuation and immugenicity in primates of vaccinia virus recombinants expression human interleukin-2," Ann. NY. Acad. Sci. 569: 86-103 (1989).

Flynn, et al., "An essential Role for Interferon γ in Resistance to *Mycobacterium tuberculosis* Infection," J. of Experimental Medicine 178: 2249-2254 (1993).

Garcia, "Nucleotide Sequence and Expression of pneumococcal autolysin gene from its own promoter in *E. coli*," Gene (43):265-292 (1986).

Geysen, et al. "Cognitive features of continuous antigenic determinants," J. Mol. Recognition 1:32-41 (1988).

Goodman-Smitkoff, et al., "Defining minimal requirements for antibody production to peptide antigens," Vaccine 8: 257-262 (1990).

Grant, et al., "Expression and Secretion Vectors for Yeast," Methods Enzymol. 153: 516-544 (1987).

Greenspan and Di Cera, "Defining epitopes: It's not as easy as it seems," Nature Biotechnology 17: 936-937 (1999).

Greenway, et al., "Enhancement of protective immune responses to Venezuelan equine encephalitis (VEE) virus with microencapsulated vaccine," Vaccine 13:1411-1420 (1995).

Griffin, et al., "Animal Models of Protective Immunity in Tuberculosis to Evaluate Candidate Vaccines;" Trends in Microbiology 3(11): 418-423 (1995).

Guzman, et al., "Efficient Gene Transfer into Myocardium by Direct Injection of Adenovirus," Cir. Res. 73: 1202-1207 (1993).

Harrison's Principles of Internal Medicine, vol. 1, pp. 1004-1014 (1998).

Harrison's Principles of Internal Medicine, vol. 1, pp. 1019-1023 (1998).

Hartman and Mulligan, "Two dominant-acting selectable markers for gene transfer studies in mammalian cells," PNAS USA 85:8047-51 (1988).

Hendrickson, et al., "Mass Spectrometric Identification of Mtb81, A Novel Serological Marker for Tuberculosis," J. Clin. Microbiol 38(6):2354-2361 (2000).

Higgins and Sharp, "Fast and sensitive multiple sequence alignments on a microcomputer," Cabios 5:151-153 (1989).

Hobbs, McGraw Hill Yearbook of Science and Technology, pp. 191-196 (1992).

Horn, et al., "Synthesis of oligonucleotides on cellulose," Nucl. Acids Res. Symposia Series, pp. 225-232 (1980).

Horwitz et al., "Protective immunity against tuberculosis induced by vaccination with major extracellular proteins of *Mycobacterium tuberculosis*," PNAS USA 92:1530-1534 (1995).

Jacobs, "Advances in mycobacterial genetics: new promises for old diseases," Immunobiology 184(2-3):147-156 (1992).

Jurcevic, et al., "T cell responses to a mixture of *Mycobacterium tuberculosis* peptide with complementary HLA-DR binding profiles," Clinical and Experimental Immunology 105(3): 416-421 (1996).

Kadival, et al. "Radioimmunoassay of tuberculous antigen," Indian J. Med. Res. 75:765-770 (1982).

Kalinowski, et al., "Genetic and biochemical analysis of the aspartokinase from Corynebacterium glutamicum," Molecular Microbiology 5:1197-1204 (1991).

Kass-Eisler, et al., "Quantitative determination of Adenoviral-mediated gene delivery to rat cardiac myocytes in vitro and in vivo," PNAS USA 90:11498-11502 (1993).

Karlin and Altschul, "Applications and statistics for multiple high-scoring segments in molecular sequences," PNAS USA 90: 5873-5787 (1993).

Kaufmann, et al., "Vaccination against tuberculosis and leprosy," Immunobiology 184(2-3): 208-229 (1992).

Khanolkar-Young, et al., "Results of the Third Immunology of Tuberculosis Antimycobacterial Monoclonal Antibody Workshop" Infection and Immunity 60(9):3925-927 (1992).

Kohler and Milstein, "Continuous cultures of fused cells secreting antibodies of predefined sequence," Nature 256:495-497 (1975).

Kolls, "Prolonged and effective blockade of TNF activity through Adenoviral-mediated gene transfer," PNAS USA 91:215-219 (1994).

Kozak, "Comparison of Initiation of Protein Synthesis in Procaryotes, Eucaryotes, and Organelles;" Microbiological Review, pp. 1-45 (1983).

Kroll, et al., "A Multifunctional Prokaryotic Protein Expression System: Overproduction, Affinity Purification, and Selective Detection," DNA Cell Biol. 12:441-453 (1993).

Lewin, Genes IV, Oxford University Press, pp. 124-126 (1990).

Launois, et al., "T-Cell Epitope Mapping of the Major Secreted Mycobacterial Antigen AG85A in Tuberculosis and Leprosy," Infection and Immunity 62:3679-87 (1994).

Lazar, et al., "Transforming Growth Factor-alpha Mutation of Aspartic Acid 47 and Leucine 48 results in Different Biological Activities" Mol. Cell. Biol. 8(3):1247-1252 (1988).

Leao, et al., "Immunological and functional characterization of proteins of the *Mycobacterium tuberculosis* antigen 85 complex using synthetic peptides," J. Gen. Microbiol. 139:1543-1549 (1993).

Lee, et al. "Characterization of the Major Membrane Protein of Virulent *Mycobacterium tuberculosis*," Infection and Immunity 60:2066-2074 (1992).

Lerner, et al., "Cloning and structure of the *Bacillus subtilis* aspartate transcarbamylas gene (pyrB)," J. Biol. Chem. 261(24):11156-11165 (1986).

Lewinsohn, et al., "Characterization of HumanCD8+ T Cells Reactive with *Mycobacterium tuberculosis*-infected Antigen-presenting Cells," J. Exp. Med. 187(10):1633-1640 (1998).

Li, et al., "Important Role of the Amino Acid Attached to tRNA in Formylation and in Initiation of Protein Synthesis in *Escherichia coli*," J. Biol. Chem., 271:1022-1028 (1996).

Ljungqvist, et al., "Antibody Responses Against *Mycobacterium tuberculosis* in 11 Strains of Inbred Mice Novel Monoclonal Antibody Specificities Generated by Fusions Using Spleens from BALB B10 and CBA-J Mice," Infections and Immunity 56(8):1994-98 (1988).

Logan and Shenk, "Advenovirus tripartite leader sequence enhances translation of mRNAs late after infection," PNAS USA 81: 365-3659 (1984).

Lowrie, et al., "Towards a DNA vaccine against tuberculosis," Vaccine 12(16):1537-1540 (1994).

Lowy, et al., "Isolation of transforming DNA: Cloning the Hamster aprt Gene," Cell 22:817-23 (1990).

Maddox, et al., "Elevated Serum Levels in Human Pregnancy of a Molecule Immunochemically similar to Eosinophil Granule Major Basic Protein," J. Exp. Med. 158:1211-1216 (1983).

Mahairas, et al., "Molecular Analysis of Genetic Differences Between *Mycrobacterium bovis* BCG and Virulent *M. bovis*," J. of Bacteriology 178(5): 1274-1282 (1996).

Mahvi, et al., "DNA Cancer Vaccines—A Gene Gun Approach," Imm. and Cell Bio. 75: 456-460 (1997).

Manca, et al., "Molecular cloning, purification, and serological characterization of MPT63, a novel antigen secreted by *Mycobacterium tuberculosis*," Infection and Immunity 65(1):16-23 (1997).

Nosoh, et al., Protein Stability and Stabilization through Protein Engineering, chap. 7, p. 197 (1991).

Oettinger, et al., "Cloning and B-cell-epitope mapping of MPT64 from *Mycobacterium tuberculosis* H37Rv," Infection and Immunity 62(5):2058-2064 (1994).

Orme, "Prospects for new vaccines against tuberculosis," Trends in Microbiology 3(10):401-404 (1995).

Ortega, et al., "Single-step purification on DEAE-sephacel of recombinant polypeptides produced in *Escherichia coli*," Biotechnology 10:795-798 (1992).

Pal, et al., "Immunization with extracellular proteins of *Mycobacterium tuberculosis* induces cell-mediated immune responses and substantial protective immunity in a guinea pig model of pulmonary tuberculosis", Infection and Immunity 60(11):4781-4792 (1992).

Pancholi, et al., "Dendritic cells efficiently immunoselect mycobacterial-reactive T cells in human blood, including clonable antigen-reactive precursors," Immunology 76(2):217-224 (1992).

Parker, et al., "Targeted Gene Walking Polymerase Chain Reactions," Nuc. Acids Res. 19: 3055-60 (1991).

Paul, Fundamental Immunology, chap. 8, 243-247 (1993).

Philipp, et al., "An integrated map of the genome of the tubercle bacillus, *Mycobacterium tuberculosis* H37Rv, and comparison with *Mycobacterium leprae*," PNAS USA 93(7):3132-3137 (1996).

Porath, et al., "Immobilized Metal Ion Affinity Chromatography," Proto Exp. Purif. 3:263-281 (1992).

Pouthier, et al., "Anti-A60 immunoglobulin G in the serodiagnosis of tuberculosis in HIV-seropositive and seronegative patients," AIDS 8(9):1277-80 (1994).

Reed, et al., "Tuberculosis vaccine development: from mouse to man," Microbes and Infection 7(5-6):992-31 (2005).

Reed, et al., "Defined tuberculosis vaccine, Mtb72F/AS02A, evidence of protection in cynomolgus monkeys," PNAS 106(7):2301-06 (2009).

Rhodes, et al., "Transformations of Maize by the Electroporation of Embryos," Methods Mol. Biol. 55:121-131 (1995).

Rinke De Wit, et al., "A Mycobacterium leprae-specific gene encoding an immunologically recognized 45 kDa protein," Mol. Microbiol. 10(4):829-838 (1993).

Rinke De Wit, et al., "Mycobacteria contains two groEL genes: the second *Mycobacterium leprae* groEL gene is arranged in an operon with groES," Mol. Microbiol. 6(14):1995-2007 (1992).

Riveau, et al., "Synthetic peptide vaccines against peptides and biological mediators," Trends in Pharmacological Sciences 11:194-198 (1990).

Roberts, et al., "Prediction of HIV peptide epitopes by a novel algorithm," AIDS Research and Human Retroviruses 12:593-610 (1996).

Romain, et al., "Identification of a *Mycobacterium bovis* BCG 45/47-Kilodalton Antigen Complex, an Immunodominant Target for Antibody Response after Immunization with Living Bacteria," Infection and Immunity 61(2):742-750 (1993).

Romain, et al., "Isolation of a proline-rich mycobacterial protein eliciting delayed-type hypersensitivity reactions only in guinea pigs immunized with living mycobacteria," PNAS USA 90:5322-5326 (1993).

Romain, et al., "Preparation of Tuberculin Antigen L," Ann. Inst. Pasteur/Microbiol. 136B:235-248 (1985).

Romano, et al., "Immunogenicity and protective efficacy of tuberculosis subunit vaccines expression PPE44 (Rv2770c)," Vaccine, 26(48):6053-63 (2008).

Rolland, "From Genes to Gene Medicines: Recent Advances in Nonviral Gene Delivery," Crit. Rev. Therap. Drug Carrier Systems 15:143-198 (1998).
Rosenfeld, et al., "Adenovirus-Mediated Transfere of a Recombinant Alpha-1 Antitrypsin Gene to Lung Epithelium in Vivo," Science 252:431-434 (1991).
Rossolini, et al., "Use of deoxyinosine-containing primers versus degenerate primers," Mol. Cell. Probes 8:91-98 (1994).
Sanderson, et al., "Identification of a CD4+ T Cell-stimulating Antigen of Pathogenic Bacteria by Expression Cloning," J. Exp. Med. 182(6):1751-1757 (1995).
Sato, et al., "Immunostimulatory DNA Sequences Necessary for Effective Intradermal Gene Immunization," Science 273:352 (1996).
Scharf, et al., "Heat Stress Promoters and Transcription Factors," Results Probl. Cell Differ. 20:125-162 (1994).
Schorey, "A *Mycobacterium leprae* Gene Encoding a Fibronectin Binding Protein is Used for Efficient Invasion of Epithelial Cells and Schwann Cells," Infection and Immunity 63(7):2652-2657 (1995).
Shinnick, "The 65-Kilodalton Antigen of *Mycobacterioum tuberculosis*," J. of Bacteriology 169(3): 1080-1088 (1987).
Singh, et al., "In Vitro Characterization of T Cells from Mycobacterium W-Vaccinated Mice," Infection and Immunity 60(1):257-263 (1992).
Sinha, et al., "Immunological properties of a 30 Kda secretory protein of *Mycobacterium tuberculosis* H37RA," Vaccine 15(6-7): 689-99 (1997).
Simonney, et al., "Analysis of the immunological humoral response to *Mycobacterium tuberculosis* glycolipid antigens (DAT, PGLTb1) for diagnosis of tuberculosis in HIV-seropositive and seronegative patients," Eur. J. of Clin. Microbiology and Infectious Disease 14(10):883-891 (1995).
Skeiky, et al., "LeIF: a recombinant leishmania protein that induces an IL-12 mediated Th cytokine profile," J. of Immunology 161: 6171-79 (1998).
Skeiky, et al., "Differential immune responses and protective efficacy induced by components of a tuberculosis polyprotein vaccine, Mtb72F, delivered as naked DNA or recombinant protein," J. of Immunology 172(12):7618-28 (2004).
Skorko-Glonek, "Comparison of the structure of wild-type HtrA heat shock protease and mutant HtrA proteins. A Fourier transform infrared spectroscopic study," JBC 270(19): 11140-11146 (1995).
Skuce, et al., "Discrimination of *M. tuberculosis* complex bacterial using novel VNTR-PCR targets," Microbiology 148(2):519-28 (2002).
Sorensen, et al., "Purification and characterization of a low-molecular-mass T-cell antigen secreted by *Mycobacterium tuberculosis*," Infection and Immunity 63(5): 1710-1717 (1995).
Stoute, et al., "A Preliminary Evaluation of a Recombinant Circumsporozoite Protein Vaccine Against Plasmodium Falciparum Malaria," New Engl. J. Med. 336:86-91 (1997).
St. Pierre, et al., "A refined vector system for the in vitro construction of single-copy transcriptional or translational fusions to lacZ," Gene169:65-68 (1996).
Timmerman and Levy, "Dendritic Cell Vaccines for Cancer Immunotherapy," Ann. Rev. Med 50: 507-529 (1999).
Triglia, et al., "A Procedure for In Vitro Amplification of DNA Sequences that Lie Outside the Boundaries of Known Sequences," Nucl. Acids Res. 16:8186 (1988).
Tsenova, et al. "Evaluation of the Mtb72F Polyprotein Vaccine in a Rabbit Model," Infection and Immunity 74(4):2922-401 (2006).
Ulmer, et al., "Heterologous Protection Against Influenze by Injection of DNA Encoding a Viral Protein," Science 259:1745-1749 (1993).
Van Pittius, et al., "Evolution and expansion of the *M. tuberculosis* PE and PPE multigene families and their association with the duplication of the ESAT-6 (esx) gene cluster regions," BML Evolutionary Biology 6(1):95 (2006).
Van Soolingen, et al., "Host-Mediated Modification of PvuII Restriction in *Mycobacterium tuberculosis*," J. of Bactreriology 178(1):78-84 (1996).
Vekemans et al., "Immune Responses to Mycobacterial Antigens in the Gambian Population,", Infection and Immunity 72(1):381-88 (2004).
Von Eschen, et al., "The candidate tuberculosis vaccine Mtb72F/AS02A," Human Vaccines 5(7):475-82 (2009).
Vega-Lopez, et al., "Sequence and immunological characterization of a serine-rich antigen from *Mycobacterium leprae*," Infection and Immunity 61(5):2145-2153 (1993).
Vordemeier, et al., "Synthetic delivery system for tuberculosis vaccines: immunological evaluation of the *M. tuberculosis* 38 kDa protein entrapped in biodegradable PLG microparticles," Vaccine 13(16):1576-1582 (1995).
Wallis, et al., "Identification of Antigens of *Mycobacterium tuberculosis* Using Human Monoclonal Antibodies," J. Clin. Invest. 84:214-219 (1989).
Wang, et al., "Tuberculosis Vaccines: Past, Present and Future," Expert Rev. Vaccines 1(3):341-54 (2002).
Webb, et al., "Molecular Cloning, Expression and Immunogenicity of MTB12," Infection & Immunity 66(9):4208-4214 (1998).
Wiegeshaus, et al., "Evaluation of the protective potency of new tuberculosis vaccines," Reviews of Infectious Diseases 11(Suppl. 2):S484-S490 (1989).
Wieles, et al., "Characterization of a *Mycobacterium leprae* Antigen Related to the Secreted *Mycobacterium tuberculosis* Protein MPT32," Infection and Immunity 62(1):252-258 (1994).
Wigler, et al., "Transformation of mammalian cells with an amplifiable dominant-acting gene," PNAS USA 77:3567-70 (1980).
Wiker and Harboe, "The Antigen 85 Complex: a Major Secretion Product of *Mycobacterium tuberculosis*," Microbiological Reviews 56(4):648-661 (1992).
Winter, "The Expression of Heat Shock Proteins and Cognate Genes During Plant Development," Results Probl. Cell Differ. 17: 85-105 (1991).
Yamaguchi, et al., "Cloning and Characterization of the Gene for Immunogenic Protein MPB64 of *Mycobacterium bovis* BDG," Infection and Immunity 57(1):283-288 (1989).
Young, et al., "Screening of a Recombinant Mycobacterial DNA Library with Polyclonal Antiserum and Molecular Weight Analysis of Expressed Antigens," Infection and Immunity 55(6):1421-1425 (1987).
Zimmerman, et al., "Immunization with peptide heteroconjugates primes a T helper cell type 1-associated antibody (IgG2a) response that recognizes the native epitope on the 38-kDa protein of *Mycobacterium tuberculosis*," Vaccine Res. 5(2):103-118 (1996).
Zitvogel, et al., "Eradiation of established murine tumors using a novel cell-free vaccine: dedritic cell-derived exosomes," Nature Med. 4:594-600 (1998).
Seq_NCBI_AF2122897, 1 page, 2000.
Seq_XP002416348_CDC1551, 2 pages, 2000.
Seq_NCBI AD000020 gi: 1717739 Dec. 10, 1996, 10 pages.
Seq_NCBI _AL021930.1, 2 pages, 2000.
Seq_NCBI _AL021930, 17 pages, 2000.
Seq_Database EMBL_U34848 "*Mycobacterium bovis* deletion region 1, 6kDa early secretory antigenic target (esat6) gene", 2000.
Seq_Accession No. O05907, Database:stpremb119, publicly available Jul. 1, 1997.
Seq_Accession No. O05908, Database:stremb119, publicly available Jul. 1, 1997.
Seq_EMBL_MTCY7H7Bc, Accession No. Z95557, May 20, 1997.
Seq_EMBL_MTCY24G1, Accession No. Z83858, Jan. 13, 1997.
Seq_EMBL_MTCY19G5, Accession No. Z77826, Jul. 31, 1996.
Seq_EMBL_MTCY261, Accession No. Z97559, Jul. 10, 1997.
Seq_EMBL_Z78020, XP002224823, 2000.
Seq_EMBL_P41403, XP002224824, 2000.
Seq_EMBL_Q50596, XP002224822, 2000.
Seq_EMBL_Z17372, XP002224825, 2000.
Seq_EMBL_U90239, XP002224826, 2000.
Seq_EMBL_P97048, XP002224827, 2000.
Seq_Accession_No_AU077540, 2000.
Seq_EMBL_P15712, (Apr. 1, 1990) "PBP-1 from *M. tuberculosis*" XP002359448.
Seq_Uniprot_Q79FV1, 2000.
Seq_Uniprot_O06267, 2000.
Seq_Uniprot_P96364, 2000.
Seq_Uniprot_O05300, 2000.

Seq_Sequence Alignment_SEQ ID No. 163-*Mycobacterium smegmatis* (Cirillo et al.), 2000.
Seq_Sequence Alignment_Corynebacterium glutamicum, 2000.
Seq_Sequence alignment_*Mycobacterium segmatis*_P41403, created Nov. 1995.
Seq_NCBI_214801_Rv0287 [*Mycobacterium tuberculosisi* H37Rv]).
Seq_NCBI_CAA17362, 2000.
Seq_EMBL_Q7U0G8-Hypothetical Protein Mb1207c, Oct. 31, 2006 XP002416347.
Seq_EMBL_050430-Hypothetical Protein Mb1207c, Oct. 31, 2006, XP002416348.
Seq_Compugen_P95242, 1997.
Seq_Compugen_P96363, 1997.
Seq_Compugen_P95243, 1997.
Seq_Compugen_P96361, 1997.
Seq_Compugen_P95012, 1997.
Seq_Compugen_Q49722, 1996.
Seq_EMBL_X84741-Mycrobacteriumbovis BCG IS1081 DNA Sequence, Van Soolingen, D., 2000.
U.S. Appl. No. 09/724,685, filed Oct. 11, 1996.
First Office Action for U.S. Appl. No. 08/658,800, 1998.
Second Office Action for U.S. Appl. No. 08/658,800, 1998.
First Office Action for U.S. Appl. No. 08/659,683, 1997.
Second Office Action for U.S. Appl. No. 08/659,683, 1998.
First Office Action for U.S. Appl. No. 08/680,573, 1998.
Second Office Action for U.S. Appl. No. 08/680,573, 1998.
First Office Action for U.S. Appl. No. 08/680,574, 1997.
Second Office Action for U.S. Appl. No. 08/680,574, 1998.
First Office Action for U.S. Appl. No. 08/729,622, 1998.
Second Office Action for U.S. Appl. No. 08/729,622, 1998.
First Office Action for U.S. Appl. No. 08/730,510, 1998.
First Office Action for U.S. Appl. No. 08/818,111, 1998.
Second Office Action for U.S. Appl. No. 08/818,111, 1999.
First Office Action for U.S. Appl. No. 08/818,112, 1998.
Second Office Action for U.S. Appl. No. 08/818,112, 1998.
First Office Action for U.S. Appl. No. 08/858,998, 1998.
First Office Action for U.S. Appl. No. 08/859,381, 1998.
First Office Action for U.S. Appl. No. 08/942,341, 1998.
First Office Action for U.S. Appl. No. 0892578, 1998.
First Office Action for U.S. Appl. No. 09/056,556, 2000.
Second Office Action for U.S. Appl. No. 09/056,556, 2000.
First Office Action for U.S. Appl. No. 09/072,967, 2000.
First Office Action for U.S. Appl. No. 09/073,009, 1999.
Second Office Action for U.S. Appl. No. 09/073,009, 2000.
Third Office Action for U.S. Appl. No. 09/073,009, 2001.
Fourth Office Action for U.S. Appl. No. 09/073,009, 2001.
First Office Action for U.S. Appl. No. 09/073,010, 2000.
Second Office Action for U.S. Appl. No. 09/073,010, 2000.
Third Office Action for U.S. Appl. No. 09/073,010, 2001.
Office Action for U.S. Appl. No. 08/730,510, 1998.
Office Action for U.S. Appl. No. 09/470,191, 2001.
First Office Action for U.S. Appl. No. 09/072,596, 2001.
Orme, Preclinical testing of new vaccines for tuberculosis: A comprehensive review, Vaccine 24:2-19 (2006).
Girard, et al., A review of vacciine research and development: Tuberculosis, Vaccine 23:5725-31 (2006).
Office Action for U.S. Appl. No. 12/698,893, 2010.

Ra35 N-terminus DNA

```
gccccgccgg ccttgtcgca ggaccggttc gccgacttcc ccgcgctgcc cctcgacccg tccgcgatgg  70
tcgcccaagt ggggccacag gtggtcaaca tcaacaccaa actgggctac aacaacgccg tgggcgccgg 140
gaccggcatc gtcatcgatc ccaacggtgt cgtgctgacc tgtcgcggg cgccaccgac 210
atcaatgcgt tcagcgtcgg ctccggccaa acctacggcg tgatcgtggt cgggtatgac cgggtcgggg cgcaccgac 280
atgtcgcggt gctgcagctg cgcggtgccg cgcggtgcag cggcctacc gtggccgcg atcggtggcg gcgtcgcggt 350
tggtgagccc gtcgtcgcga tgggcaacag cggtgggcag cgtgcaggcg ggcggaacgc cccgtgccgt gcctgccgg 420
gtggtcgcgc tcggccaaac cgtgcaggcc cgtgcaggcg tcggattcgc tgaccggtgc cgaagagaca ttgaacgggt 490
tgatccagtt cgatgccgcg atccagcccg gtgattcggg cggcccgtc gtcaacggcc taggacaggt 560
ggtcggtatg aacacgggcc cgtcctag
588
```

Ra35 N-terminus amino acid sequence

Ala Pro Pro Ala Leu Ser Gln Asp Arg Phe Ala Asp Phe Pro Ala Leu Pro Leu Asp Pro Ser Ala
                    5                  10                  15                  20

Met Val Ala Gln Val Gly Pro Gln Val Val Asn Ile Asn Thr Lys Leu Gly Tyr Asn Asn Ala Val
                25                  30                  35                  40

Gly Ala Gly Thr Gly Ile Val Ile Asp Pro Asn Gly Val Val Leu Thr Asn Asn His Val Ile Ala
                45                  50                  55                  60                  65

Gly Ala Thr Asp Ile Asn Ala Phe Ser Val Gly Ser Gly Gln Thr Tyr Gly Val Asp Val Val Gly
                70                  75                  80                  85

Tyr Asp Arg Thr Gln Asp Val Ala Val Leu Gln Leu Arg Gly Ala Gly Gly Leu Pro Ser Ala Ala
                90                  95                 100                 105                 110

FIG. 4.

Ile Gly Gly Gly Val Ala Val Gly Glu Pro Val Val Ala Met Gly Asn Ser Gly Gly Gln Gly Gly
115                         120                         125                         130

Thr Pro Arg Ala Val Pro Gly Arg Val Val Ala Leu Gly Gln Thr Val Gln Ala Ser Asp Ser Leu
135                         140                         145                         150

Thr Gly Ala Glu Glu Thr Leu Asn Gly Leu Ile Gln Phe Asp Ala Ala Ile Gln Pro Gly Asp Ser
155                         160                         165                         170                         175

Gly Gly Pro Val Val Asn Gly Leu Gly Gln Val Val Gly Met Asn Thr Ala Ala Ser
180                         185                         190                         195

*FIG. 4. (CONTINUED)*

```
         Ra12
1    MHHHHHH[TAASDNFQLSQGGQGFAIPIPIGQAMAIAGQIRSGGGSPTVHIGPTAEFLG      MTB72F
1    MHHHHHH[TAASDNFQLSQGGQGFAIPIPIGQAMAIAGQIRSGGGSPTVHIGPTAEFLG      MTB72FMutSA

56   LGVVDNNGNGARVQRVVGSAPAASLGISTGDVITAVDGAPINSATAMADALNGHH          MTB72F
56   LGVVDNNGNGARVQRVVGSAPAASLGISTGDVITAVDGAPINSATAMADALNGHH          MTB72FMutSA
                                  TbH9FL
111  PGDVISVTWQTKSFFTRTFNVTLAEGPPA]E[FMVDFGALPPEINSARMYAGPGSAS        MTB72F
111  PGDVISVTWQTKSFFTRTFNVTLAEGPPA]E[FMVDFGALPPEINSARMYAGPGSAS        MTB72FMutSA

166  LVAAAQMWDSVASDLFSAASAFQSVVWGLTVGSWIGSSAGLMVAAASPYVAWMSV          MTB72F
166  LVAAAQMWDSVASDLFSAASAFQSVVWGLTVGSWIGSSAGLMVAAASPYVAWMSV          MTB72FMutSA

221  TAGQAELTAAQVRVAAAAYETAYGLTVPPPVIAENRAELMILIATNLLGQNTPAI          MTB72F
221  TAGQAELTAAQVRVAAAAYETAYGLTVPPPVIAENRAELMILIATNLLGQNTPAI          MTB72FMutSA

276  AVNEAEYGEMWAQDAAAMFGYAAATATATATLLPFEEAPEMTSAGGLLEQAAAVE          MTB72F
276  AVNEAEYGEMWAQDAAAMFGYAAATATATATLLPFEEAPEMTSAGGLLEQAAAVE          MTB72FMutSA

331  EASDTAAANQLMNNVPQALQQLAQPTQGTTPSSKLGGLWKTVSPHRSPISNMVSM          MTB72F
331  EASDTAAANQLMNNVPQALQQLAQPTQGTTPSSKLGGLWKTVSPHRSPISNMVSM          MTB72FMutSA

386  ANNHMSMTNSGVSMTNTLSSMLKGFAPAAAAQAVQTAAQNGVRAMSSLGSSLGSS          MTB72F
386  ANNHMSMTNSGVSMTNTLSSMLKGFAPAAAAQAVQTAAQNGVRAMSSLGSSLGSS          MTB72FMutSA

441  GLGGGVAANLGRAASVGSLSVPQAWAAANQAVTPAARALPLTSLTSAAERGPGQM          MTB72F
441  GLGGGVAANLGRAASVGSLSVPQAWAAANQAVTPAARALPLTSLTSAAERGPGQM          MTB72FMutSA
```

FIG. 5.

```
              Ra35
496  LGGLPVGQMGARAGGGLSGVLRVPPRPYVMPHSPAAGD APPALSQDRFADFPAL              MTB72F
496  LGGLPVGQMGARAGGGLSGVLRVPPRPYVMPHSPAAGD APPALSQDRFADFPAL              MTB72FMutSA

551  PLDPSAMVAQVGPQVVNINTKLGYNNAVGAGTGIVIDPNGVVLTNNNVIAGATDI              MTB72F
551  PLDPSAMVAQVGPQVVNINTKLGYNNAVGAGTGIVIDPNGVVLTNNHVIAGATDI              MTB72FMutSA

606  NAFSVGSGQTYGVDVVGYDRTQDVAVLQLRGAGGLPSAAIGGGVAVGEPVVAMGN              MTB72F
606  NAFSVGSGQTYGVDVVGYDRTQDVAVLQLRGAGGLPSAAIGGGVAVGEPVVAMGN              MTB72FMutSA

661  SGGQGGTPRAVPGRVVALGQTVQASDSLTGAEETLNGLIQFDAAIQPGDSGGPVV              MTB72F
661  SGGQGGTPRAVPGRVVALGQTVQASDSLTGAEETLNGLIQFDAAIQPGD A GPVV              MTB72FMutSA

716  NGLGQVVGMNTAAS                                                       MTB72F
716  NGLGQVVGMNTAAS                                                       MTB72FMutSA
```

*FIG. 5. (CONTINUED)*

```
    Ra35 N-term
  1 MHHHHHH APPALSQDRFADFPALPLDPSAMVAQVGPQVVNINTKLGYNNA  Ra35/MTB32A
  1 MHHHHHH APPALSQDRFADFPALPLDPSAMVAQVGPQVVNINTKLGYNNA  Ra35FLMutSA 51 VGAGTGIVIDPNGVVLTNNHVIAGATDINAFSVGSGQTYGVDVVGYDRTQ  Ra35/MTB32A
 51 VGAGTGIVIDPNGVVLTNNHVIAGATDINAFSVGSGQTYGVDVVGYDRTQ  Ra35FLMutSA 101 DVAVLQLRGAGGLPSAAIGGVAVGEPVVAMGNSGGQGGTPRAVPGRVVA   Ra35/MTB32A
101 DVAVLQLRGAGGLPSAAIGGVAVGEPVVAMGNSGGQGGTPRAVPGRVVA   Ra35FLMutSA
                                                      Ra12 Cterm
151 LGQTVQASDSLTGAEETLNGLIQFDAAIQPGDSGGPVVNGLGQVVGMN TA  Ra35/MTB32A
151 LGQTVQASDSLTGAEETLNGLIQFDAAIQPGDA GGPVVNGLGQVVGMN TA  Ra35FLMutSA
                 end Ra35 Nterm
201 AS DNFQLSQGGGQGFAIPIGQAMAIAGQIRSGGGGSSPTVHIGPTAFLGLGVV  Ra35/MTB32A
201 AS DNFQLSQGGGQGFAIPIGQAMAIAGQIRSGGGGSSPTVHIGPTAFLGLGVV  Ra35FLMutSA 251 DNNGNGARVQRVVGSAPAASLGISTGDVITAVDGAPINSATAMADALNGH  Ra35/MTB32A
251 DNNGNGARVQRVVGSAPAASLGISTGDVITAVDGAPINSATAMADALNGH  Ra35FLMutSA 301 HPGDVISVTWQTKSGGTRTGNVTLAEGPPA end  Ra12       Ra35/MTB32A
301 HPGDVISVTWQTKSGGTRTGNVTLAEGPPA                 Ra35FLMutSA
```

FUSION PROTEINS OF MYCOBACTERIUM TUBERCULOSIS

CROSS-REFERENCES TO RELATED APPLICATIONS

The present application is a continuation of U.S. patent application Ser. No. 11/418,848, filed 5 May 2006, now allowed, which is a continuation of U.S. patent application Ser. No. 09/886,349, filed 20 Jun. 2001, now U.S. Pat. No. 7,083,796, which claims priority to U.S. application No. 60/265,737, filed 1 Feb. 2001, and is also a continuation-in-part of U.S. patent application Ser. No. 09/597,796, filed 20 Jun. 2000, now U.S. Pat. No. 7,186,412, which claims priority to U.S. patent application Ser. No. 60/158,338, filed 7 Oct. 1999, and U.S. application Ser. No. 60/158,425, filed 7 Oct. 1999, and is also a continuation-in-part of U.S. patent application Ser. No. 09/287,849, filed 7 Apr. 1999, now U.S. Pat. No. 6,627,198, which is a continuation-in-part of U.S. patent application Ser. No. 09/223,040, filed 30 Dec. 1998, now U.S. Pat. No. 6,544,522. The contents of each document mentioned above are hereby incorporated by reference in the entirety.

STATEMENT AS TO RIGHTS TO INVENTIONS MADE UNDER FEDERALLY SPONSORED RESEARCH AND DEVELOPMENT

Not applicable.

FIELD OF THE INVENTION

The present invention relates to fusion proteins containing at least two *Mycobacterium* sp. antigens. In particular, it relates to nucleic acids encoding fusion proteins that include two or more individual *M. tuberculosis* antigens, which increase serological sensitivity of sera from individuals infected with tuberculosis, and methods for their use in the diagnosis, treatment, and prevention of tuberculosis infection.

BACKGROUND OF THE INVENTION

Tuberculosis is a chronic infectious disease caused by infection with *M. tuberculosis* and other *Mycobacterium* species. It is a major disease in developing countries, as well as an increasing problem in developed areas of the world, with about 8 million new cases and 3 million deaths each year. Although the infection may be asymptomatic for a considerable period of time, the disease is most commonly manifested as an acute inflammation of the lungs, resulting in fever and a nonproductive cough. If untreated, serious complications and death typically result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistance.

In order to control the spread of tuberculosis, effective vaccination and accurate early diagnosis of the disease are of utmost importance. Currently, vaccination with live bacteria is the most efficient method for inducing protective immunity. The most common mycobacterium employed for this purpose is *Bacillus* Calmette-Guerin (BCG), an avirulent strain of *M. bovis*. However, the safety and efficacy of BCG is a source of controversy and some countries, such as the United States, do not vaccinate the general public with this agent.

Diagnosis of tuberculosis is commonly achieved using a skin test, which involves intradermal exposure to tuberculin PPD (protein-purified derivative). Antigen-specific T cell responses result in measurable induration at the injection site by 48-72 hours after injection, which indicates exposure to mycobacterial antigens. Sensitivity and specificity have, however, been a problem with this test, and individuals vaccinated with BCG cannot be distinguished from infected individuals.

While macrophages have been shown to act as the principal effectors of *Mycobacterium* immunity, T cells are the predominant inducers of such immunity. The essential role of T cells in protection against *Mycobacterium* infection is illustrated by the frequent occurrence of *Mycobacterium* infection in AIDS patients, due to the depletion of CD4$^+$ T cells associated with human immunodeficiency virus (HIV) infection. *Mycobacterium*-reactive CD4$^+$ T cells have been shown to be potent producers of γ-interferon (IFN-γ), which, in turn, has been shown to trigger the anti-mycobacterial effects of macrophages in mice. While the role of IFN-γ in humans is less clear, studies have shown that 1,25-dihydroxy-vitamin D3, either alone or in combination with IFN-γ or tumor necrosis factor-alpha, activates human macrophages to inhibit *M. tuberculosis* infection. Furthermore, it is known that IFN-γ stimulates human macrophages to make 1,25-dihydroxy-vitamin D3. Similarly, interleukin-12 (IL-12) has been shown to play a role in stimulating resistance to *M. tuberculosis* infection. For a review of the immunology of *M. tuberculosis* infection, see Chan & Kaufmann, *Tuberculosis: Pathogenesis, Protection and Control* (Bloom ed., 1994), and *Harrison's Principles of Internal Medicine*, volume 1, pp. 1004-1014 and 1019-1023 (14$^{th}$ ed., Fauci et al., eds., 1998).

Accordingly, there is a need for improved diagnostic reagents, and improved methods for diagnosis, preventing and treating tuberculosis.

SUMMARY OF THE INVENTION

The present invention therefore provides compositions comprising at least two heterologous antigens, fusion proteins comprising the antigens, and nucleic acids encoding the antigens, where the antigens are from a *Mycobacterium* species from the tuberculosis complex and other *Mycobacterium* species that cause opportunistic infections in immune compromised patients. The present invention also relates methods of using the polypeptides and polynucleotides in the diagnosis, treatment and prevention of *Mycobacterium* infection.

In one aspect, the present invention provides compositions and fusion proteins comprising a mutated version of Ra35 (N-terminal portion of MTB32A) or Ra35FL (full length MTB32A), in which one, two, or three of the three amino acids histidine, aspartate, or serine at the active site has been mutated to a different amino acid. In one embodiment, in Ra35FL, the serine at position 183 has been mutated to an alanine residue, creating Ra35FLMutSA. In one embodiment, the DNA encoding Ra35FL has been mutated by changing a T to a G, resulting in a serine to alanine mutation at amino acid 183 of SEQ ID NO:4. In another embodiment, the present invention provides the fusion protein MTB72FMutSA, in which the Ra35 component of the fusion protein has a serine to alanine mutation at amino acid position 710 of the MTB72F sequence. In another embodiment, the present invention provides a nucleic acid encoding the fusion protein MTB72F, in which the nucleic acid encoding the Ra35 component has been mutated by changing a T to a G, resulting in a serine to alanine mutation at amino acid position 710 of the MTB72F sequence.

The present invention is based, in part, on the inventors' discovery that fusion polynucleotides, fusion polypeptides, or compositions that contain at least two heterologous *M. tuberculosis* coding sequences or antigens are highly antigenic and upon administration to a patient increase the sensitivity of tuberculosis sera. In addition, the compositions, fusion polypeptides and polynucleotides are useful as diagnostic tools in patients that may have been infected with *Mycobacterium*.

In one aspect, the compositions, fusion polypeptides, and nucleic acids of the invention are used in in vitro and in vivo assays for detecting humoral antibodies or cell-mediated immunity against *M. tuberculosis* for diagnosis of infection or monitoring of disease progression. For example, the polypeptides may be used as an in vivo diagnostic agent in the form of an intradermal skin test. The polypeptides may also be used in in vitro tests such as an ELISA with patient serum. Alternatively, the nucleic acids, the compositions, and the fusion polypeptides may be used to raise anti-*M. tuberculosis* antibodies in a non-human animal. The antibodies can be used to detect the target antigens in vivo and in vitro.

In another aspect, the compositions, fusion polypeptides and nucleic acids may be used as immunogens to generate or elicit a protective immune response in a patient. The isolated or purified polynucleotides are used to produce recombinant fusion polypeptide antigens in vitro, which are then administered as a vaccine. Alternatively, the polynucleotides may be administered directly into a subject as DNA vaccines to cause antigen expression in the subject, and the subsequent induction of an anti-*M. tuberculosis* immune response. Thus, the isolated or purified *M. tuberculosis* polypeptides and nucleic acids of the invention may be formulated as pharmaceutical compositions for administration into a subject in the prevention and/or treatment of *M. tuberculosis* infection. The immunogenicity of the fusion protein or antigens may be enhanced by the inclusion of an adjuvant, as well as additional fusion polypeptides, from *Mycobacterium* or other organisms, such as bacterial, viral, mammalian polypeptides. Additional polypeptides may also be included in the compositions, either linked or unlinked to the fusion polypeptide or compositions.

BRIEF DESCRIPTION OF THE DRAWINGS

FIG. 4 shows the nucleotide (SEQ ID NO:50) and amino acid (SEQ ID NO:8) sequence of Ra35 (195 amino acids from the N-terminal portion of MTB32A).

FIG. 5 shows an alignment of the amino acid sequences of MTB72F (SEQ ID NO: 16) and the mutated version MTB72FMutSA (SEQ ID NO: 18).

FIG. 6 shows an alignment of the amino acid sequences of mature (full length) Ra35/MTB32A (SEQ ID NO:4) and the mutated version Ra35FLMutSA (SEQ ID NO:6).

FIG. 7 shows long term survival of guinea pigs vaccinated with Mtb72F formulations.

DESCRIPTION OF THE SPECIFIC EMBODIMENTS

Figure 1:
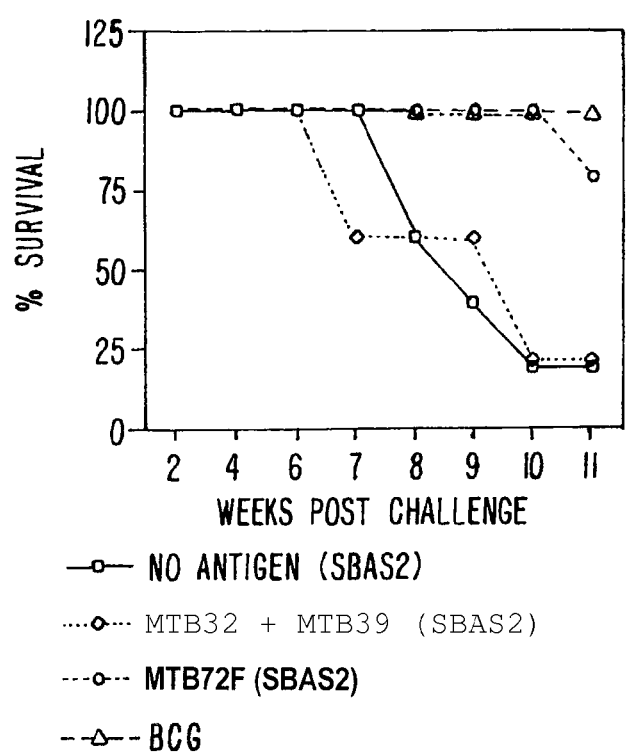
FIG. 1 shows percent survival of Guinea pigs vaccinated with MTB72F polyprotein.

The present invention relates to compositions comprising antigen compositions and fusion polypeptides useful for the diagnosis and treatment of *Mycobacterium* infection, polynucleotides encoding such antigens, and methods for their use. The antigens of the present invention are polypeptides or fusion polypeptides of *Mycobacterium* antigens and immunogenic thereof. More specifically, the compositions of the present invention comprise at least two heterologous polypeptides of a *Mycobacterium* species of the tuberculosis complex, e.g., a species such as *M. tuberculosis, M. bovis*, or *M. africanum*, or a *Mycobacterium* species that is environmental or opportunistic and that causes opportunistic infections such as lung infections in immune compromised hosts (e.g., patients with AIDS), e.g., BCG, *M. avium, M. intracellulare, M. celatum, M. genavense, M. haemophilum, M. kansasii, M. simiae, M. vaccae, M. fortuitum*, and *M. scrofulaceum* (see, e.g., *Harrison's Principles of Internal Medicine*, volume 1, pp. 1004-1014 and 1019-1023 (14$^{th}$ ed., Fauci et al., eds., 1998). The inventors of the present application surprisingly discovered that compositions and fusion proteins comprising at least two heterologous *Mycobacterium* antigens, or immunogenic fragments thereof, where highly antigenic. These compositions, fusion polypeptides, and the nucleic acids that encode them are therefore useful for eliciting protective response in patients, and for diagnostic applications.

The antigens of the present invention may further comprise other components designed to enhance the antigenicity of the antigens or to improve these antigens in other aspects, for example, the isolation of these antigens through addition of a stretch of histidine residues at one end of the antigen. The compositions, fusion polypeptides, and nucleic acids of the invention can comprise additional copies of antigens, or additional heterologous polypeptides from *Mycobacterium* sp., such as MTB8.4 antigen, MTB9.8 antigen, MTB9.9 antigen, MTB40 antigen, MTB41 antigen, 38-1, TbRa3, 38 kD, DPEP, TbH4, DPPD, ESAT-6 antigen, MTB85 complex antigen (e.g., MTB85b), or α-crystalline antigen, and Erd14. The compositions, fusion polypeptides, and nucleic acids of the invention can also comprise additional heterologous polypeptides from other non-Mycobacterium sources. For example, the compositions and fusion proteins of the invention can include polypeptides or nucleic acids encoding polypeptides, wherein the polypeptide enhances expression of the antigen, e.g., NS1, an influenza virus protein, or an immunogenic portion thereof (see, e.g. WO99/40188 and WO93/04175). The nucleic acids of the invention can be engineered based on codon preference in a species of choice, e.g., humans.

The compositions of the invention can be naked DNA, or the compositions, e.g., polypeptides can also comprise adjuvants, e.g., MPL, 3D-MPL, IFA, AS adjuvants such as AS2, AS2', AS2", AS4, AS6, ENHANZYN (Detox), QS21, CWS, TDM, AGP, CPG, Leif, saponin, and saponin mimetics, and derivatives thereof. In addition, the compositions of the invention can comprise BCG or Pvac as an adjuvant.

In one embodiment, the compositions and fusion proteins of the invention are composed of at least two antigens selected from the group consisting of a MTB39 antigen or an immunogenic fragment thereof from a *Mycobacterium* species of the tuberculosis complex, and a MTB32A antigen or an immunogenic fragment thereof from a *Mycobacterium* species of the tuberculosis complex.

In another embodiment, the antigens are selected from the group consisting of a MTB39 antigen or an immunogenic fragment thereof from a *Mycobacterium* species of the tuberculosis complex, and a polypeptide comprising at least 205 amino acids of the N-terminus of a MTB32A antigen from a *Mycobacterium* species of the tuberculosis complex.

In another embodiment, the antigens are selected from the group consisting of a MTB39 antigen or an immunogenic fragment thereof from a *Mycobacterium* species of the tuberculosis complex, a polypeptide comprising at least about 205 amino acids of the N-terminus of a MTB32A antigen from a *Mycobacterium* species of the tuberculosis complex, and a polypeptide comprising at least about 132 amino acids from the C-terminus of MTB32A antigen from a *Mycobacterium* species of the tuberculosis complex.

In the nomenclature of the application, Ra35 refers to the N-terminus of MTB32A (Ra35FL), comprising at least about 195 to 205 amino acids of MTB32A from *M. tuberculosis*, or the corresponding region from another *Mycobacterium* species. Ra12 refers to the C-terminus of MTB32A (Ra35FL), comprising at least about the last 132 amino acids from MTB32A from *M. tuberculosis*, or the corresponding region from another *Mycobacterium* species.

The following provides sequences of some antigens used in the compositions and fusion proteins of the invention:

SEQ ID NO: 1-4: MTB32A (Ra35FL or Ra35 mature), the sequence of which is also disclosed as SEQ ID NO: 17 (cDNA) and SEQ ID NO:79 (protein) in the U.S. patent application Ser. Nos. 08/523,436, 08/523,435, 08/658,800, 08/659,683, 08/818,112, now U.S. Pat. No. 6,290,969, Ser. No. 09/056,556, Now U.S. Pat. No. 6,350,456, and Ser. No. 08/818,111, now U.S. Pat. No. 6,338,852, and in the WO97/09428 and WO97/09429 applications, see also Skeiky et al., *Infection and Immunity* 67:3998-4007 (1999). The term MTB32A also includes MTB32A amino acid sequences in which any one of the three amino acids at the active site triad (His, Asp, Ser), e.g., the serine residue at amino acid position 208 in SEQ ID NO:2 or amino acid position 183 in SEQ ID NO:4, has been changed to another amino acid (e.g., alanine, Ra35FLMutSA, see, e.g., FIG. 6 and SEQ ID NO:6).

SEQ ID NO:5 and 6: Ra35FLMut SA, the mature version of RA35FL in which the serine residue at amino acid position 183 of SEQ ID NO:4 has been changed to an alanine residue.

SEQ ID NO:7 and 8: Ra35, the N-terminus of MTB32A (Ra35FL), comprising at least about 195 amino acids from the N-terminus of MTB32A from *M. tuberculosis*, the nucleotide and amino acid sequence of which is disclosed in FIG. 4 (see also amino acids 33-227 of SEQ ID NO:2 and amino acids 8 to 202 of SEQ ID NO:4). The term Ra35 (N-term) also includes Ra35 amino acid sequences in which any one of the three amino acids at the active site triad (i.e., His, Asp, or Ser) has been changed as described above.

SEQ ID NO:9 and 10: MTBRa12, the C-terminus of MTB32A (Ra35FL), comprising at least about 132 amino acids from the C-terminus of MTB32A from *M. tuberculosis* (see, e.g., amino acids 224 to 355 of SEQ ID NO:2 and amino acids 199 to 330 of SEQ ID NO:4), the sequence of which is disclosed as SEQ ID NO:4 (DNA) and SEQ ID NO:66 (predicted amino acid sequence) in the U.S. patent application Ser. No. 09/072,967, now U.S. Pat. No. 6,592,877.

SEQ ID NO: 11, 12, 13, and 14: MTB39 (TbH9), the sequence of which is disclosed as SEQ ID NO: 106 (cDNA full length) and SEQ ID NO: 107 (protein full length) in the U.S. patent application Ser. No. 08/658,800, Ser. No. 08/659,683, Ser. No. 08/818,112, now U.S. Pat. No. 6,290,969, and Ser. No. 08/818,111, now U.S. Pat. No. 6,338,852, and in the WO97/09428 and WO97/09429 applications. The sequence is also disclosed as SEQ ID NO:33 (DNA) and SEQ ID NO:91 (amino acid) in U.S. patent application Ser. No. 09/056,556, now U.S. Pat. No. 6,350,456.

The following provides sequences of some fusion proteins of the invention

SEQ ID NO:15 and 16: MTB72F (Ra12-TbH9-Ra35), the sequence of which is disclosed as SEQ ID NO: 1 (DNA) and SEQ ID NO:2 (protein) in the U.S. patent application Ser. No. 09/223,040, and in the PCT/US99/07717 application. The term MTB372F also includes MTB72F amino acid sequences in which any one of the three amino acids at the active site triad in Ra35FL (i.e., His, Asp, or Ser), has been changed as described above (see, e.g., MTB72FMutSA (SEQ ID NO:18), FIG. 5).

SEQ ID NO:17 and 18: MTB72FMutSA (Ra12-TbH9-Ra35MutSA), wherein, in the Ra35 component of the fusion protein, the serine at position 710 has been changed to an alanine.

SEQ ID NO:19 and 20: TbH9-Ra35 (MTB59F), the sequence of which is disclosed as SEQ ID NO:23 (cDNA) and SEQ ID NO:24 (protein) in the U.S. patent application Ser. No. 09/287,849, now U.S. Pat. No. 6,627,198, and in the PCT/US99/07717 application.

The following provides sequences of some additional antigens used in the compositions and fusion proteins of the invention:

SEQ ID NO: 21 and 22: MTB8.4 (DPV), the sequence of which is disclosed as SEQ ID NO: 101 (cDNA) and SEQ ID NO: 102 (protein) in the U.S. patent application Ser. Nos. 08/658,800, 08/659,683, 08/818,112, now U.S. Pat. No. 6,290,969, and Ser. No. 08/818,111, now U.S. Pat. No. 6,338,852, and in the WO97/09428 and WO97/09429 applications.

SEQ ID NO:23 and 24: MTB9.8 (MSL), the sequence of which is disclosed as SEQ ID NO: 12 (DNA), SEQ ID NO: 109 (predicted amino acid sequence) and SEQ ID NO: 110 to 124 (peptides) in the U.S. patent application Ser. Nos. 08/859,381, 08/858,998, 09/073,009, now U.S. Pat. No. 6,555,653, and Ser. No. 09/073,010, now U.S. Pat. No. 6,613,881, and in the PCT/US98/10407 and PCT/US98/10514 applications.

SEQ ID NO:25, 26, and 27: MTB9.9A (MTI, also known as MTI-A), the sequence of which is disclosed as SEQ ID NO:3 and SEQ ID NO:4 (DNA) and SEQ ID NO:29 and SEQ ID NO:51 to 66 (ORF peptide for MTI) in the U.S. patent application Ser. Nos. 08/859,381, 08/858,998, 09/073,009, now U.S. Pat. No. 6,555,653, and Ser. No. 09/073,010, now U.S. Pat. No. 6,613,881, and in the PCT/US98/10407 and PCT/US98/10514 applications. Two other MTI variants also exist, called MTI-B and MTI-C.

SEQ ID NO:28 and 29: MTB40 (HTCC#1), the sequence of which is disclosed as SEQ ID NO: 137 (cDNA) and 138 (predicted amino acid sequence) in the U.S. patent applications No. 09/073,009, now U.S. Pat. No. 6,555,653, and Ser. No. 09/073,010, now U.S. Pat. No. 6,613,881, and in the PCT/US98/10407 and PCT/US98/10514 applications.

SEQ ID NO:30 and 31: MTB41 (MTCC#2), the sequence of which is disclosed as SEQ ID NO: 140 (cDNA) and SEQ ID NO: 142 (predicted amino acid sequence) in the U.S. patent application Ser. No. 09/073,009, now U.S. Pat. No. 6,555,653, and Ser. No. 09/073,010, now U.S. Pat. No. 6,613,881, and in the PCT/US98/10407 and PCT/US98/10514 applications.

SEQ ID NO:32 and 33: ESAT-6, the sequence of which is disclosed as SEQ ID NO: 103 (DNA) and SEQ ID NO: 104 (predicted amino acid sequence) in the U.S. patent application Ser. No. 09/072,967, now U.S. Pat. No. 6,592,877. The sequence of ESAT-6 is also disclosed in U.S. Pat. No. 5,955,077.

SEQ ID NO:34 and 35: Tb38-1 or 38-1 (MTb11), the sequence of which is disclosed in SEQ ID NO:46 (DNA) and SEQ ID NO:88 (predicted amino acid) in the U.S. patent application Ser. No. 09/072,967, now U.S. Pat. No. 6,592,877; Ser. Nos. 08/523,436; 08/523,435; 08/818,112, now U.S. Pat. No. 6,290,969; and Ser. No. 08/818,111, now U.S. Pat. No. 6,338,852; and in the WO97/09428 and WO97/09429 applications.

SEQ ID NO:36 and 37: TbRa3, the sequence of which is disclosed in SEQ ID NO: 15 (DNA) and SEQ ID NO:77 (predicted amino acid sequence) of WO 97/09428 and WO97/09429 applications.

SEQ ID NO:38 and 39: 38 kD, the sequence of which is disclosed in SEQ ID NO: 154 (DNA) and SEQ ID NO: 155 (predicted amino acid sequence) in the U.S. patent application Ser. No. 09/072,967, now U.S. Pat. No. 6,592,877. 38 kD has two alternative forms, with and without the N-terminal cysteine residue.

SEQ ID NO:40 and 41: DPEP, the sequence of which is disclosed in SEQ ID NO:52 (DNA) and SEQ ID NO:53 (predicted amino acid sequence) in the WO97/09428 and WO97/09429 publications.

SEQ ID NO:42 and 43: TbH4, the sequence of which is disclosed as SEQ ID NO:43 (DNA) and SEQ ID NO:81 (predicted amino acid sequence) in WO97/09428 and WO97/09429 publications.

SEQ ID NO:44 and 45: DPPD, the sequence of which is disclosed in SEQ ID NO:240 (DNA) and SEQ ID NO:241 (predicted amino acid sequence) in U.S. Ser. No. 09/072,967, now U.S. Pat. No. 6,592,877, and in the PCT/US99/03268 and PCT/US99/03265 applications. The secreted form of DPPD is shown herein in FIG. 12 of PCT/US00/28095.

MTb82 (MTb867), the sequence of which is disclosed in FIGS. 8 (DNA) and 9 (amino acid) of PCT/US00/2809.

Erd14 (MTb16), the cDNA and amino acids sequences of which are disclosed in Verbon et al., *J. Bacteriology* 174: 1352-1359 (1992).

α-crystalline antigen, the sequence of which is disclosed in Verbon et al., *J. Bact.* 174:1352-1359 (1992);

85 complex antigen, e.g., 85b antigen, the sequence of which is disclosed in Content et al, *Infect. & Immunol.* 59:3205-3212 (1991).

The following provides sequences of some additional fusion proteins used in the compositions and fusion proteins of the invention:

SEQ ID NO:46 and 47: DPV-MTI-MSL (MTb31F), the sequence of which is disclosed as SEQ ID NO:18 (cDNA) and in SEQ ID NO:19 (protein) in the U.S. patent application Ser. No. 09/287,849, now U.S. Pat. No. 6,627,198, and in the PCT/US99/07717 application.

SEQ ID NO:48 and 49: DPV-MTI-MSL-MTCC#2 (MTb71F), the sequence of which is disclosed in SEQ ID NO: 15 (nucleic acid) and SEQ ID NO: 16 (protein) in the U.S. patent application Ser. No. 09/287,849, now U.S. Pat. No. 6,627,198, and in the PCT/US99/07717 application.

Each of the above sequences is also disclosed in Cole et al. *Nature* 393:537 (1998) and can be found at, e.g., sanger.ac.uk and pasteur.fr/mycdb/.

The above sequences are disclosed in U.S. patent application Ser. Nos. 08/523,435, 08/523,436, 08/658,800, 08/659,683, 08/818,111, now U.S. Pat. No. 6,338,852, Ser. No. 08/818,112, now U.S. Pat. No. 6,290,969, Ser. Nos. 08/942,341, 08/942,578, 08/858,998, 08/859,381, 09/056,556, now U.S. Pat. No. 6,350,456, Ser. No. 09/072,596, now U.S. Pat. No. 6,458,366, Ser. No. 09/072,967, now U.S. Pat. No. 6,592,877, Ser. No. 09/073,009, now U.S. Pat. No. 6,555,653, Ser. No. 09/073,010, now U.S. Pat. No. 6,613,881, Ser. No. 09/223,040, now U.S. Pat. No. 6,544,522, Ser. No. 09/287,849, now U.S. Pat. No. 6,627,198, Ser. No. 09/597,796; and in PCT patent applications PCT/US00/28095; PCT/US98/10407, PCT/US98/10514, PCT/US99/03265, PCT/US99/03268, PCT/US99/07717, WO97/09428 and WO97/09429, WO98/16645, WO98/16646, each of which is herein incorporated by reference.

The antigens described herein include polymorphic variants and conservatively modified variations, as well as inter-strain and interspecies *Mycobacterium* homologs. In addition, the antigens described herein include subsequences or truncated sequences. The fusion proteins may also contain additional polypeptides, optionally heterologous peptides from *Mycobacterium* or other sources. These antigens may be modified, for example, by adding linker peptide sequences as described below. These linker peptides may be inserted between one or more polypeptides which make up each of the fusion proteins.

DEFINITIONS

"Fusion polypeptide" or "fusion protein" refers to a protein having at least two heterologous *Mycobacterium* sp. polypeptides covalently linked, either directly or via an amino acid linker. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order. This term also refers to conservatively modified variants, polymorphic variants, alleles, mutants, subsequences, interspecies homologs, and immunogenic fragments of the antigens that make up the fusion protein. *Mycobacterium tuberculosis* antigens are described in Cole et al., *Nature* 393:537 (1998), which discloses the entire *Mycobacterium tuberculosis* genome. The complete sequence of *Mycobacterium tuberculosis* can also be found at websites sanger.ac.uk and pasteur.fr/mycdb/ (MycDB). Antigens from other *Mycobacterium* species that correspond to *M. tuberculosis* antigens can be identified, e.g., using sequence comparison algorithms, as described herein, or other methods known to those of skill in the art, e.g., hybridization assays and antibody binding assays. Fusion proteins of the invention can also comprise additional copies of a component antigen or immunogenic fragment thereof.

A polynucleotide sequence comprising a fusion protein of the invention hybridizes under stringent conditions to at least two nucleotide sequences, each encoding an antigen polypeptide selected from the group consisting of MTB39 or an immunogenic fragment thereof and MTB32A or an immunogenic fragment thereof. The polynucleotide sequences encoding the individual antigens of the fusion polypeptide therefore include conservatively modified variants, polymorphic variants, alleles, mutants, subsequences, immunogenic fragments, and interspecies homologs of MTB39 and MTB32A. The polynucleotide sequence encoding the individual polypeptides of the fusion protein can be in any order.

In some embodiments, the individual polypeptides of the fusion protein are in order (N- to C-terminus) from large to small. Large antigens are approximately 30 to 150 kD in size, medium antigens are approximately 10 to 30 kD in size, and small antigens are approximately less than 10 kD in size. The sequence encoding the individual polypeptide may be as small as, e.g., an immunogenic fragment such as an individual CTL epitope encoding about 8 to 9 amino acids, or, e.g., an HTL or B cell epitope. The fragment may also include multiple epitopes. The immunogenic fragment may also represent a larger part of the antigen sequence, e.g., about 50% or more of MTB39 and MTB32A, e.g., the N- and C-terminal portions of MTB32A. Preferred immunogenic fragments of MTB32A include Ra12, Ra35, and Ra35MutSA.

A fusion polypeptide of the invention specifically binds to antibodies raised against at least two antigen polypeptides, wherein each antigen polypeptide is selected from the group consisting of MTB39 or an immunogenic portion or fragment thereof and MTB32A or an immunogenic portion thereof. The antibodies can be polyclonal or monoclonal. Optionally, the fusion polypeptide specifically binds to antibodies raised against the fusion junction of the antigens, which antibodies do not bind to the antigens individually, i.e., when they are not part of a fusion protein. The fusion polypeptides optionally comprise additional polypeptides, e.g., three, four, five, six, or more polypeptides, up to about 25 polypeptides, optionally heterologous polypeptides or repeated homologous polypeptides, fused to the at least two heterologous antigens. The additional polypeptides of the fusion protein are optionally derived from *Mycobacterium* as well as other sources, such as other bacterial, viral, or invertebrate, vertebrate, or mammalian sources. The individual polypeptides of the fusion protein can be in any order. As described herein, the fusion protein can also be linked to other molecules, including additional polypeptides. The compositions of the invention can also comprise additional polypeptides that are unlinked to the fusion proteins of the invention. These additional polypeptides may be heterologous or homologous polypeptides.

The term "fused" refers to the covalent linkage between two polypeptides in a fusion protein. The polypeptides are typically joined via a peptide bond, either directly to each other or via an amino acid linker. Optionally, the peptides can be joined via non-peptide covalent linkages known to those of skill in the art.

"FL" refers to full-length, i.e., a polypeptide that is the same length as the wild-type polypeptide.

The term "immunogenic fragment thereof" refers to a polypeptide comprising an epitope that is recognized by cytotoxic T lymphocytes, helper T lymphocytes or B cells. Preferred immunogenic fragments of, e.g., MTB32A, are RA35, Ra35MutSA, or Ra12.

The term "*Mycobacterium* species of the tuberculosis complex" includes those species traditionally considered as causing the disease tuberculosis, as well as *Mycobacterium* environmental and opportunistic species that cause tuberculosis and lung disease in immune compromised patients, such as patients with AIDS, e.g., *M. tuberculosis, M. bovis*, or *M. africanum*, BCG, *M. avium, M. intracellulare, M. celatum, M. genavense, M. haemophilum, M. kansasii, M. simiae, M. vaccae, M. fortuitum*, and *M. scrofulaceum* (see, e.g., *Harrison's Principles of Internal Medicine*, volume 1, pp. 1004-1014 and 1019-1023 (14th ed., Fauci et al., eds., 1998).

An adjuvant refers to the components in a vaccine or therapeutic composition that increase the specific immune response to the antigen (see, e.g., Edelman, *AIDS Res. Hum Retroviruses* 8:1409-1411 (1992)). Adjuvants induce immune responses of the Th1-type and Th-2 type response. Th1-type cytokines (e.g., IFN-γ, IL-2, and IL-12) tend to favor the induction of cell-mediated immune response to an administered antigen, while Th-2 type cytokines (e.g., IL-4, IL-5, Il-6, IL-10 and TNF-β) tend to favor the induction of humoral immune responses.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of monoclonal or polyclonal antibodies, any technique known in the art can be used (see, e.g., Kohler & Milstein, *Nature* 256:495-497 (1975); Kozbor et al., *Immu-* nology Today 4:72 (1983); Cole et al, pp. 77-96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al, *Nature* 348:552-554 (1990); Marks et al., *Biotechnology* 10:779-783 (1992)).

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to fusion proteins can be selected to obtain only those polyclonal antibodies that are specifically immunoreactive with fusion protein and not with individual components of the fusion proteins. This selection may be achieved by subtracting out antibodies that cross-react with the individual antigens. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

Polynucleotides may comprise a native sequence (i.e., an endogenous sequence that encodes an individual antigen or a portion thereof) or may comprise a variant of such a sequence. Polynucleotide variants may contain one or more substitutions, additions, deletions and/or insertions such that the biological activity of the encoded fusion polypeptide is not diminished, relative to a fusion polypeptide comprising native antigens. Variants preferably exhibit at least about 70% identity, more preferably at least about 80% identity and most preferably at least about 90% identity to a polynucleotide sequence that encodes a native polypeptide or a portion thereof.

The terms "identical" or percent "identity," in the context of two or more nucleic acids or polypeptide sequences, refer to two or more sequences or subsequences that are the same or have a specified percentage of amino acid residues or nucleotides that are the same (i.e., 70% identity, optionally 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 25 to about 50 amino acids or nucleotides in length, or optionally over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 25 to 500, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984).

Another example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information website ncbi.nlm.nih.gov/-). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Polynucleotide Compositions

As used herein, the terms "DNA segment" and "polynucleotide" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the DNA segments of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

The terms "isolated," "purified," or "biologically pure" therefore refer to material that is substantially or essentially free from components that normally accompany it as found in its native state. Of course, this refers to the DNA segment as originally isolated, and does not exclude other isolated proteins, genes, or coding regions later added to the composition by the hand of man. Purity and homogeneity are typically determined using analytical chemistry techniques such as polyacrylamide gel electrophoresis or high performance liquid chromatography. A protein that is the predominant species present in a preparation is substantially purified. An isolated nucleic acid is separated from other open reading frames that flank the gene and encode proteins other than the gene.

As will be recognized by the skilled artisan, polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a *Mycobacterium* antigen or a portion thereof) or may comprise a variant, or a biological or antigenic functional equivalent of such a sequence. Polynucleotide variants may contain one or more substitutions, additions, deletions and/or insertions, as further described below, preferably such that the immunogenicity of the encoded polypeptide is not diminished, relative to a native tumor protein. The effect on the immunogenicity of the encoded polypeptide may generally be assessed as described herein. The term "variants" also encompasses homologous genes of xenogenic origin.

In additional embodiments, the present invention provides isolated polynucleotides and polypeptides comprising various lengths of contiguous stretches of sequence identical to or complementary to one or more of the sequences disclosed herein. For example, polynucleotides are provided by this invention that comprise at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative DNA segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention, for example polynucleotides that are optimized for human and/or primate codon selection. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotide Identification and Characterization

Polynucleotides may be identified, prepared and/or manipulated using any of a variety of well established techniques. For example, a polynucleotide may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using a Synteni microarray (Palo Alto, Calif.) according to the manufacturer's instructions (and essentially as described by Schena et al., *Proc. Natl. Acad. Sci. USA* 93:10614-10619 (1996) and Heller et al., *Proc. Natl. Acad. Sci. USA* 94:2150-2155 (1997)). Alternatively, polynucleotides may be amplified from cDNA prepared from cells expressing the proteins described herein, such as *M. tuberculosis* cells. Such polynucleotides may be amplified via polymerase chain reaction (PCR). For this approach, sequence-specific primers may be designed based on the sequences provided herein, and may be purchased or synthesized.

An amplified portion of a polynucleotide of the present invention may be used to isolate a full length gene from a suitable library (e.g., a *M. tuberculosis* cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual* (1989)). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22-30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186 (1988)), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1: 111-19 (1991)) and walking PCR (Parker et al., *Nucl. Acids. Res.* 19:3055-60 (1991)). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

Polynucleotide Expression in Host Cells

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al., *Nucl. Acids Res. Symp. Ser*. pp. 215-223 (1980), Horn et al., *Nucl. Acids Res. Symp. Ser*. pp. 225-232 (1980)). Alternatively, the protein itself may be produced using chemical methods to synthesize the amino acid sequence of a polypeptide, or a portion thereof. For example, peptide synthesis can be performed using various solid-phase techniques (Roberge et al., *Science* 269:202-204 (1995)) and automated synthesis may be achieved, for example, using the ABI 431A Peptide Synthesizer (Perkin Elmer, Palo Alto, Calif.).

A newly synthesized peptide may be substantially purified by preparative high performance liquid chromatography (e.g., Creighton, *Proteins, Structures and Molecular Principles* (1983)) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., *Molecular Cloning, A Laboratory Manual* (1989), and Ausubel et al., *Current Protocols in Molecular Biology* (1989).

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke &Schuster, *J. Biol. Chem.* 264:5503-5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al., *Methods Enzymol.* 153:516-544 (1987).

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, *EMBO J.* 6:307-311 (1987)). Alternatively, plant promoters such as the small subunit of RUBISCO or heat shock promoters may be used (Coruzzi et al., *EMBO J.* 3:1671-1680 (1984); Broglie et al., *Science* 224:838-843 (1984); and Winter et al, *Results Probl. Cell Differ.* 17:85-105 (1991)). These constructs can be introduced into plant cells by direct DNA transformation or pathogen-mediated transfection. Such techniques are described in a number of generally available reviews (see, e.g., Hobbs in *McGraw Hill Yearbook of Science and Technology* pp. 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia larvae* in which the polypeptide of interest may be expressed (Engelhard et al., *Proc. Natl. Acad. Sci. U.S.A.* 91: 3224-3227 (1994)).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, *Proc. Natl. Acad. Sci. U.S.A.* 81:3655-3659 (1984)). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf. et al., *Results Probl. Cell Differ.* 20:125-162 (1994)).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., *Cell* 11:223-32 (1977)) and adenine phosphoribosyltransferase (Lowy et al., *Cell* 22:817-23 (1990)) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler et al., *Proc. Natl. Acad. Sci. U.S.A.* 77:3567-70 (1980)); npt, which confers resistance to the aminoglycosides, neomycin and G-418 (Colbere-Garapin et al., *J. Mol. Biol.* 150:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman & Mulligan, *Proc. Natl. Acad. Sci. U.S.A.* 85:8047-51 (1988)). Recently, the use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes et al., *Methods Mol. Biol.* 55:121-131 (1995)).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells which contain and express a desired polynucleotide sequence may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton et al., *Serological Methods, a Laboratory Manual* (1990) and Maddox et al., *J. Exp. Med.* 158:1211-1216 (1983).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath et al., *Prot. Exp. Purif.* 3:263-281 (1992) while the enterokinase cleavage site provides a means for purifying the desired polypeptide from the fusion protein. A discussion of vectors which contain fusion proteins is provided in Kroll et al., *DNA Cell Biol.* 12:441-453 (1993)).

In addition to recombinant production methods, polypeptides of the invention, and fragments thereof, may be produced by direct peptide synthesis using solid-phase techniques (Merrifield, *J. Am. Chem. Soc.* 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

In Vivo Polynucleotide Delivery Techniques

In additional embodiments, genetic constructs comprising one or more of the polynucleotides of the invention are introduced into cells in vivo. This may be achieved using any of a variety or well known approaches, several of which are outlined below for the purpose of illustration.

1. Adenovirus

One of the preferred methods for in vivo delivery of one or more nucleic acid sequences involves the use of an adenovirus expression vector. "Adenovirus expression vector" is meant to include those constructs containing adenovirus sequences sufficient to (a) support packaging of the construct and (b) to express a polynucleotide that has been cloned therein in a sense or antisense orientation. Of course, in the context of an antisense construct, expression does not require that the gene product be synthesized.

The expression vector comprises a genetically engineered form of an adenovirus. Knowledge of the genetic organization of adenovirus, a 36 kb, linear, double-stranded DNA virus, allows substitution of large pieces of adenoviral DNA with foreign sequences up to 7 kb (Grunhaus A, et al., *Virology*,1994 May 1;200(2):535-46). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, *Radiother Oncol.* 1990 November;19(3):197-218. The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., *Adv Cancer Res.* 1977;25:1-51. Since the E3 region is dispensable from the adenovirus genome (Jones & Shenk, *Cell.* 1978 January;13(1):181-8.), the current adenovirus vectors, with the help of 293 cells, carry foreign DNA in either the El, the D3 or both regions (Prevec et al. *J Acquir Immune Defic Syndr.* 1991;4(6):568-76). In nature, adenovirus can package approximately 105% of the wild-type genome (Ghosh-Choudhury et al., *Biochem Biophys Res Commun.* 1987 September 30;147(3):964-73), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, *Science.* 1993 May 14;260(5110):926-32).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the currently preferred helper cell line is 293.

Recently, Griffiths and Racher (*Cytotechnology.* 1994;15 (1-3):3-9) disclosed improved methods for culturing 293 cells and propagating adenovirus. In one format, natural cell aggregates are grown by inoculating individual cells into 1liter siliconized spinner flasks (Techne, Cambridge, UK) containing 100-200 ml of medium. Following stifling at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlemneyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain a conditional replication-defective adenovirus vector for use in the present invention, since Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (*EMBO J.* 1986 September;5(9):2377-85) or in the E4 region where a helper cell line or helper virus complements the E4 defect.

Adenovirus is easy to grow and manipulate and exhibits broad host range in vitro and in vivo. This group of viruses can be obtained in high titers, e.g., 10.sup.9-10.sup.11 plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch RB et al., *Am Rev Respir Dis.* 1963 September;88:*SUPPL* 394-403; Top et al., *J Infect Dis.* 1971 August;124(2):155-60), demonstrating their safety and therapeutic potential as in vivo gene transfer vectors.

Adenovirus vectors have been used in eukaryotic gene expression (Levrero et al., *Gene.* 1991 May 30;101(2):195-202; Gomez-Foix et al., *J Biol Chem.* 1992 December 15;267 (35):25129-34) and vaccine development (Grunhaus & Horwitz, *Virology,*1994 May 1;200(2):535-46; Prevec et al. *J Acquir Immune Defic Syndr.* 1991;4(6):568-76). Recently, animal studies suggested that recombinant adenovirus could be used for gene therapy (Rosenfeld et al., *Science.* 1991 April 19;252(5004):431-4; Stratford-Perricaudet et al., Hum Gene Ther. 1990 Fall;1(3):241-56; Rich et al. *Hum Gene Ther.* 1993 August;4(4):461-76). Studies in administering recombinant adenovirus to different tissues include trachea instillation (Rosenfeld et al., 1991, supra; Rosenfeld et al., *Cell.* 1992 January 10;68(1):143-55), muscle injection (Ragot *Nature.* 1993 February 18;361(6413):647-50), peripheral intravenous injections (Herz & Gerard, *Proc Natl Acad Sci USA.* 1993 April 1;90(7):2812-6) and stereotactic inoculation into the brain (Le Gal La Salle et al., *Gene Ther.* 1994;1 Suppl 1:S52).

2. Retroviruses

The retroviruses are a group of single-stranded RNA viruses characterized by an ability to convert their RNA to double-stranded DNA in infected cells by a process of reverse-transcription (Coffin, *J Med Virol.* 1990 May;31(1): 43-9). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990, supra).

In order to construct a retroviral vector, a nucleic acid encoding one or more oligonucleotide or polynucleotide sequences of interest is inserted into the viral genome in the place of certain viral sequences to produce a virus that is replication-defective. In order to produce virions, a packaging cell line containing the gag, pol, and env genes but without the LTR and packaging components is constructed (Mann et al., *Cell.* 1983May;33(1):153-9). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas & Rubenstein, *Biotechnology* 1988;10:493-513; Temin HM, *Cell Biophys.* 1986 December;9(1-2):9-16; Mann et al., 1983, supra). The media containing the recombinant retroviruses is then collected, optionally concentrated, and used for gene transfer. Retroviral vectors are able to infect a broad variety of cell types. However, integration and stable expression require the division of host cells (Paskind et al., *Virology.* 1975 September; 67(1):242-8).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., *Proc Natl Acad Sci USA.* 1989 December;86(23):9079-83). Using antibodies against major histocompatibility complex class I and class II antigens, they demonstrated the infection of a variety of human cells that bore those surface antigens with an ecotropic virus in vitro (Roux et al., 1989, supra).

3. Adeno-Associated Viruses

AAV (Ridgeway, 1988; Hermonat & Muzycska, *Proc Natl Acad Sci USA*. 1984October;81(20):6466-70) is a parvovirus, discovered as a contamination of adenoviral stocks. It is a ubiquitous virus (antibodies are present in 85% of the U.S. human population) that has not been linked to any disease. It is also classified as a dependovirus, because its replications is dependent on the presence of a helper virus, such as adenovirus. Five serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter (Muzyczka & McLaughlin, *J. Virol.* 1988 June;62(6):1963-73).

The AAV DNA is approximately 4.7 kilobases long. It contains two open reading frames and is flanked by two ITRs. There are two major genes in the AAV genome: rep and cap. The rep gene codes for proteins responsible for viral replications, whereas cap codes for capsid protein VP1-3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three viral promoters have been identified and named p5, p19, and p40, according to their map position. Transcription from p5 and p19 results in production of rep proteins, and transcription from p40 produces the capsid proteins (Hermonat & Muzyczka, 1984, supra).

There are several factors that prompted researchers to study the possibility of using rAAV as an expression vector One is that the requirements for delivering a gene to integrate into the host chromosome are surprisingly few. It is necessary to have the 145-bp ITRs, which are only 6% of the AAV genome. This leaves room in the vector to assemble a 4.5-kb DNA insertion. While this carrying capacity may prevent the AAV from delivering large genes, it is amply suited for delivering the antisense constructs of the present invention.

AAV is also a good choice of delivery vehicles due to its safety. There is a relatively complicated rescue mechanism: not only wild type adenovirus but also AAV genes are required to mobilize rAAV. Likewise, AAV is not pathogenic and not associated with any disease. The removal of viral coding sequences minimizes immune reactions to viral gene expression, and therefore, rAAV does not evoke an inflammatory response.

4. Other Viral Vectors as Expression Constructs

Other viral vectors may be employed as expression constructs in the present invention for the delivery of oligonucleotide or polynucleotide sequences to a host cell. Vectors derived from viruses such as vaccinia virus (Ridgeway, *Biotechnology* 1988;10:467-92; Coupar et al., *Gene.* 1988 August 15;68(1):1-10), lentiviruses, polio viruses and herpes viruses may be employed. They offer several attractive features for various mammalian cells (Friedmann, *Mol Biol Med.* 1989 April;6(2):117-25; Ridgeway, 1988, supra; Coupar et al., 1988, supra; Summers J, Smith PM, and Horwich AL, *J Virol.* 1990 June;64(6):2819-24).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al, *J Virol.* 1990February;64(2):642-50). This suggested that large portions of the genome could be replaced with foreign genetic material. The hepatotropism and persistence (integration) were particularly attractive properties for liver-directed gene transfer. Chang et al. (*Hepatology,* 14:124A, 1991) introduced the chloramphenicol acetyltransferase (CAT) gene into duck hepatitis B virus genome in the place of the polymerase, surface, and presurface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991, supra).

5. Non-Viral Vectors

In order to effect expression of the oligonucleotide or polynucleotide sequences of the present invention, the expression construct must be delivered into a cell. This delivery may be accomplished in vitro, as in laboratory procedures for transforming cells lines, or in vivo or ex vivo, as in the treatment of certain disease states. As described above, one preferred mechanism for delivery is via viral infection where the expression construct is encapsulated in an infectious viral particle.

Once the expression construct has been delivered into the cell the nucleic acid encoding the desired oligonucleotide or polynucleotide sequences may be positioned and expressed at different sites. In certain embodiments, the nucleic acid encoding the construct may be stably integrated into the genome of the cell. This integration may be in the specific location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In certain embodiments of the invention, the expression construct comprising one or more oligonucleotide or polynucleotide sequences may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (*Proc. Nat. Acad. Sci. USA,* 81:7529-7533, 1984) successfully injected polyomavirus DNA in the form of calcium phosphate precipitates into liver and spleen of adult and newborn mice demonstrating active viral replication and acute infection. Benvenisty & Reshef (*Proc. Nat. Acad. Sci. USA,* 83:9551-9555, 1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., *Nature* 1987 327:70-73). Several devices for accelerating small particles have been developed. One such device relies on a high voltage discharge to generate an electrical current, which in turn provides the motive force (Yang et al., *Proc. Natl. Acad. Sci. USA,* 1990 87:9568-9572). The microprojectiles used have consisted of biologically inert substances such as tungsten or gold beads.

Selected organs including the liver, skin, and muscle tissue of rats and mice have been bombarded in vivo (Yang et al, 1990, supra; Zelenin et al., *FEBS Lett.,* 1991 280:94-96). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

Polypeptide Compositions

The present invention, in other aspects, provides polypeptide compositions. Generally, a polypeptide of the invention will be an isolated polypeptide (or an epitope, variant, or active fragment thereof) derived from a mammalian species. Preferably, the polypeptide is encoded by a polynucleotide sequence disclosed herein or a sequence which hybridizes under moderately stringent conditions to a polynucleotide sequence disclosed herein. Alternatively, the polypeptide may be defined as a polypeptide which comprises a contiguous amino acid sequence from an amino acid sequence disclosed herein, or which polypeptide comprises an entire amino acid sequence disclosed herein.

Immunogenic portions may generally be identified using well known techniques, such as those summarized in Paul, *Fundamental Immunology,* 3rd ed., 243-247 (1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a *Mycobacterium* sp. protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow & Lane, *Antibodies: A Laboratory Manual* (1988). For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, and higher eukaryotic cells, such as mammalian cells and plant cells. Preferably, the host cells employed are *E. coli,* yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Polypeptides of the invention, immunogenic fragments thereof, and other variants having less than about 100 amino acids, and generally less than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149-2146 (1963). Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46 (1985); Murphy et al., *Proc. Natl. Acad. Sci. USA* 83:8258-8262 (1986); U.S. Pat. No. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided. Such proteins comprise a polypeptide as described herein together with an unrelated immunogenic protein. Preferably the immunogenic protein is capable of eliciting a recall response. Examples of such proteins include tetanus, tuberculosis and hepatitis proteins (see, e.g., Stoute et al., *New Engl. J. Med.* 336:86-91 (1997)).

Within preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265-292 (1986)). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795-798 (1992)). Within a preferred embodiment, a repeat portion of LYTA may be incorporated into a fusion protein. A repeat portion is found in the C-terminal region starting at residue 178. A particularly preferred repeat portion incorporates residues 188-305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

T Cells

Immunotherapeutic compositions may also, or alternatively, comprise T cells specific for a *Mycobacterium* antigen. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. No. 5,240,856; 5,215,926; WO 89/06280; WO 91/16116 and WO 92/07243). Alternatively, T cells may be derived from related or unrelated humans, non-human mammals, cell lines or cultures.

T cells may be stimulated with a polypeptide of the invention, polynucleotide encoding such a polypeptide, and/or an antigen presenting cell (APC) that expresses such a polypeptide. Such stimulation is performed under conditions and for a time sufficient to permit the generation of T cells that are specific for the polypeptide. Preferably, the polypeptide or polynucleotide is present within a delivery vehicle, such as a microsphere, to facilitate the generation of specific T cells.

T cells are considered to be specific for a polypeptide of the invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065-1070 (1994)). Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a polypeptide of the invention (100 ng/ml-100 µg/ml, preferably 200 ng/ml-25 µg/ml) for 3-7 days should result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., *Current Protocols in Immunology*, vol. 1 (1998)). T cells that have been activated in response to a polypeptide, polynucleotide or polypeptide-expressing APC may be $CD4^+$ and/or $CD8^+$. Protein-specific T cells may be expanded using standard techniques. Within preferred embodiments, the T cells are derived from a patient, a related donor or an unrelated donor, and are administered to the patient following stimulation and expansion.

For therapeutic purposes, $CD4^+$ or $CD8^+$ T cells that proliferate in response to a polypeptide, polynucleotide or APC can be expanded in number either in vitro or in vivo. Proliferation of such T cells in vitro may be accomplished in a variety of ways. For example, the T cells can be re-exposed to a polypeptide, or a short peptide corresponding to an immunogenic portion of such a polypeptide, with or without the addition of T cell growth factors, such as interleukin-2, and/or stimulator cells that synthesize the polypeptide. Alternatively, one or more T cells that proliferate in the presence of the protein can be expanded in number by cloning. Methods for cloning cells are well known in the art, and include limiting dilution.

Pharmaceutical Compositions

In additional embodiments, the present invention concerns formulation of one or more of the polynucleotide, polypeptide, T-cell and/or antibody compositions disclosed herein in pharmaceutically-acceptable or physiologically-acceptable solutions for administration to a cell or an animal, either alone, or in combination with one or more other modalities of therapy. Such compositions are also useful for diagnostic uses.

It will also be understood that, if desired, the nucleic acid segment, RNA, DNA or PNA compositions that express a polypeptide as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

1. Oral Delivery

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (Mathiowitz et al., *Nature*. 1997 March 27;386 (6623):410; Gupta S K, Hwang et al., *J Clin Pharmacol*. 1998 January;38(1):60-7; U.S. Pat. Nos. 5,641,515; 5,580,579 and 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

2. Injectable Delivery

In certain circumstances it will be desirable to deliver the pharmaceutical compositions disclosed herein parenterally, intravenously, intramuscularly, or even intraperitoneally as described in U.S. Pat. Nos. 5,543,158;5,641,515 and 5,399, 363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington's Pharmaceutical Sciences,* 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

3. Nasal Delivery

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described e.g., in U.S. Pat. Nos. 5,756,353 and 5,804,212 (each specifically incorporated herein by reference in its entirety) Likewise, the delivery of drugs using intranasal microparticle resins (Takenaga et al., *J Control Release.* 1998 ; March 2;52(1-2):81-7) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

4. LIPOSOME-, Nanocapsule-, and Microparticle-Mediated Delivery

In certain embodiments, the inventors contemplate the use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, or a nanoparticle or the like.

Such formulations may be preferred for the introduction of pharmaceutically-acceptable formulations of the nucleic acids or constructs disclosed herein. The formation and use of liposomes is generally known to those of skill in the art (see for example, Couvreur et al., *FEBS Lett.* 1977 December 15;84(2):323-6; Couvreur, *Crit Rev Ther Drug Carrier Syst.* 1988;5(1):1-20; Lasic, *Trends Biotechnol.* 1998 July;16(7): 307-21; which describes the use of liposomes and nanocapsules in the targeted antibiotic therapy for intracellular bacterial infections and diseases). Recently, liposomes were developed with improved serum stability and circulation half-times (Gabizon & Papahadjopoulos, *Proc Natl Acad Sci USA.* 1988 September;85(18):6949-53; Allen and Chonn, *FEBS Lett.* 1987 October 19;223(1):42-6; U.S. Pat. No. 5,741,516, specifically incorporated herein by reference in its entirety). Further, various methods of liposome and liposome like preparations as potential drug carriers have been reviewed (Takakura, Nippon Rinsho, 1998 March;56(3):691-5; Chandran et al., *Indian J Exp Biol.* 1997 August;35(8):801-9; Margalit, *Crit Rev Ther Drug Carrier Syst.* 1995;12(2-3) : 233-61; U.S. Pat. Nos. 5,567,434; 5,552,157; 5,565,213; 5,738,868 and 5,795,587, each specifically incorporated herein by reference in its entirety).

Liposomes have been used successfully with a number of cell types that are normally resistant to transfection by other procedures including T cell suspensions, primary hepatocyte cultures and PC 12 cells (Renneisen et al., *J Biol Chem.* 1990 September 25;265(27):16337-42; Muller et al., *Chem Phys Lipids.* 1990 January;52(2):111-27). In addition, liposomes are free of the DNA length constraints that are typical of viral-based delivery systems. Liposomes have been used effectively to introduce genes, drugs (Heath & Martin, Chem Phys Lipids. 1986 June-July;40(2-4):347-58; Heath et al., Biochim Biophys Acta. 1986 November 6;862(1):72-80; Balazsovits et al., 1989; Cancer Chemother Pharmacol. 1989;23 (2):81-6; Fresta and Puglisi, *Biomaterials.* 1996April;17(8): 751-8), radiotherapeutic agents (Pikul et al., *Arch Surg.* 1987December;122(12):1417-20), enzymes (Imaizumi et al., *Acta Neurochir Suppl (Wien).* 1990;51:236-8; Imaizumi et al., *Stroke.* 1990 September;21(9):1312-7), viruses (Faller & Baltimore, *J Virol.* 1984 January;49(1):269-72), transcription factors and allosteric effectors (Nicolau & Gersonde, *Blut.* 1979 July;39(1):1-7) into a variety of cultured cell lines and animals. In addition, several successful clinical trails examining the effectiveness of liposome-mediated drug delivery have been completed (Lopez-Berestein et al., *J Infect Dis.* 1985 April;151(4):704-10; Lopez-Berestein et al., *Cancer Drug Deliv.* 1985 Summer;2(3):183-9; Coune, *Infection.* 1988 May-June ;16(3):141-7; Sculier et al., *Eur J Cancer Clin Oncol.* 1988 March;24(3):527-38). Furthermore, several studies suggest that the use of liposomes is not associated with autoimmune responses, toxicity or gonadal localization after systemic delivery (Mori & Fukatsu, *Epilepsia.* 1992 November-December;33(6):994-1000).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. *FEBS Lett.* 1977 December 15;84(2):323-6; and Couvreur et al., *Crit Rev Ther Drug Carrier Syst.* 1988;5(1):1-20, the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins, such as cytochrome c, bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity, and surface charge. They may persist in tissues for h or days, depending on their composition, and half lives in the blood range from min to several h. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow, and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for pharmaceutically-acceptable nanocapsule formulations of the compositions of the present invention. Nanocapsules can generally entrap compounds in a stable and reproducible way (Henry-Michelland et al., *J Pharm Pharmacology.* 1987 December;39(12):973-7; Quintanar-Guerrero et al., *Drug Dev Ind Pharm.* 1998 December;24(12):1113-28; Douglas et al., *Crit Rev Ther Drug Carrier Syst.* 1987;3(3):233-61). To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention. Such particles may be are easily made, as described (Couvreur et al., 1980supra and 1988 supra; zur Muhlen et al., *Eur J Pharm Biopharm.* 1998 March 45(2):149-55; Zambaux et al. *J Control Release.* 1998 January 2;50(1-3):31-40; Pinto-Alphandry et al., 1995 *J Drug Target.* 1995;3(2):167-9 and U.S. Pat. No. 5,145,684, specifically incorporated herein by reference in its entirety).

Vaccines

In certain preferred embodiments of the present invention, vaccines are provided. The vaccines will generally comprise one or more pharmaceutical compositions, such as those discussed above, in combination with an immunostimulant. An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes (into which the compound is incorporated; see, e.g., Fullerton, U.S. Pat. No. 4,235,877). Vaccine preparation is generally described in, for example, Powell & Newman, eds., Vaccine Design (the subunit and adjuvant approach) (1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound, within the composition or vaccine.

Illustrative vaccines may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143-198 (1998), and references cited therein. Appropriate nucleic acid expression systems contain the necessary DNA sequences for expression in the patient (such as a suitable promoter and terminating signal). Bacterial delivery systems involve the administration of a bacterium (such as *Bacillus*-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317-321 (1989); Flexner et al., *Ann. N.Y. Acad. Sci.* 569:86-103 (1989); Flexner et al., *Vaccine* 8:17-21 (1990); U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616-627 (1988); Rosenfeld et al., *Science* 252:431-434 (1991); Kolls et al., *Proc. Natl. Acad. Sci. USA* 91:215-219 (1994); Kass-Eisler et al, *Proc. Natl. Acad. Sci. USA* 90:11498-11502 (1993); Guzman et al., *Circulation* 88:2838-2848 (1993); and Guzman et al., *Cir. Res.* 73:1202-1207 (1993). Techniques for incorporating DNA into such expression systems are well known to those of ordinary skill in the art. The DNA may also be "naked," as described, for example, in Ulmer et al., *Science* 259:1745-1749 (1993) and reviewed by Cohen, *Science* 259:1691-1692 (1993). The uptake of naked DNA may be increased by coating the DNA onto biodegradable beads, which are efficiently transported into the cells. It will be apparent that a vaccine may comprise both a polynucleotide and a polypeptide component. Such vaccines may provide for an enhanced immune response.

It will be apparent that a vaccine may contain pharmaceutically acceptable salts of the polynucleotides and polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

While any suitable carrier known to those of ordinary skill in the art may be employed in the vaccine compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252. One may also employ a carrier comprising the particulate-protein complexes described in U.S. Pat. No. 5,928,647, which are capable of inducing a class I-restricted cytotoxic T lymphocyte responses in a host.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

Any of a variety of immunostimulants may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium* species or *Mycobacterium* derived proteins. For example, delipidated, deglycolipidated *M. vaccae* ("pVac") can be used. In another embodiment, BCG is used as an adjuvant. In addition, the vaccine can be administered to a subject previously exposed to BCG. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 and derivatives thereof (SmithKline Beecham, Philadelphia, Pa.); CWS, TDM, Leif, aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann & Coffman, *Ann. Rev. Immunol.* 7:145-173 (1989).

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Corixa Corporation (Seattle, Wash.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352 (1996). Another preferred adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other preferred formulations include more than one saponin in the adjuvant combinations of the present invention, for example combinations of at least two of the following group comprising QS21, QS7, Quil A, β-escin, or digitonin.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol® to increase viscosity, or may be formulated in a dry powder form with a powder excipient such as lactose.

In one preferred embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 as disclosed in WO 00/09159. Preferably the formulation additionally comprises an oil in water emulsion and tocopherol.

Other preferred adjuvants include Montanide ISA 720 (Seppic, France), SAF (Chiron, Calif., United States), ISCOMS (CSL), MF-59 (Chiron), the SBAS series of adjuvants (e.g., SBAS-2, AS2', AS2," SBAS-4, or SBAS6, available from SmithKline Beecham, Rixensart, Belgium), Detox (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 (now U.S. Pat No. 6,113,918) and Ser. No. 09/074,720 (now U.S. Pat. No. 6,355,257), the disclosures of which are incorporated herein by reference in their entireties, and polyoxyethylene ether adjuvants such as those described in WO 99/52549A1.

Other preferred adjuvants include adjuvant molecules of the general formula (I):

wherein, n is 1-50, A is a bond or —C(O)—, R is $C_{1-50}$ alkyl or Phenyl $C_{1-50}$ alkyl.

One embodiment of the present invention consists of a vaccine formulation comprising a polyoxyethylene ether of general formula (I), wherein n is between 1 and 50, preferably 4-24, most preferably 9; the R component is $C_{1-50}$, preferably $C_4$-$C_{20}$ alkyl and most preferably $C_{12}$ alkyl, and A is a bond. The concentration of the polyoxyethylene ethers should be in the range 0.1-20%, preferably from 0.1-10%, and most preferably in the range 0.1-1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index ($12^{th}$ edition: entry 7717). These adjuvant molecules are described in WO 99/52549.

The polyoxyethylene ether according to the general formula (I) above may, if desired, be combined with another adjuvant. For example, a preferred adjuvant combination is preferably with CpG as described in the pending UK patent application GB 9820956.2.

Any vaccine provided herein may be prepared using well known methods that result in a combination of antigen, immune response enhancer and a suitable carrier or excipient. The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g., Coombes et al., *Vaccine* 14:1429-1438 (1996)) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly(lactide-co-glycolide), polyacrylate, latex, starch, cellulose, dextran and the like. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see, e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau & Steinman, *Nature* 392:245-251 (1998)) and have been shown to be effective as a physiological adjuvant for eliciting prophylactic or therapeutic antitumor immunity (see Timmerman & Levy, *Ann. Rev. Med.* 50:507-529 (1999)). In general, dendritic cells may be identified based on their typical shape (stellate in situ, with marked cytoplasmic processes (dendrites) visible in vitro), their ability to take up, process and present antigens with high efficiency and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594-600 (1998)).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding a protein (or portion or other variant thereof) such that the polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and Cell Biology* 75:456-460 (1997). Antigen loading of dendritic cells may be achieved by incubating dendritic cells or progenitor cells with the polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Vaccines and pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a vaccine or pharmaceutical composition may be stored in a freeze-dried condition requiring only the addition of a sterile liquid carrier immediately prior to use.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a protein in a biological sample. Such kits generally comprise at least one oligonucleotide probe or primer, as described above, that hybridizes to a polynucleotide encoding a protein. Such an oligonucleotide may be used, for example, within a PCR or hybridization assay. Additional components that may be present within such kits include a second oligonucleotide and/or a diagnostic reagent or container to facilitate the detection of a polynucleotide encoding a protein of the invention.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example 1

Guinea Pig Vaccination with MTB72F Fusion Protein and Compositions with Individual Antigens Guinea pigs were immunized with adjuvant alone (SBAS1, SBAS2, or ASAS7 plus Al(OH)$_3$), MTB72F fusion protein in adjuvant, or TbH9 plus Ra35 antigen composition.

Methods:
Groups: 1) SBAS1
2) SBAS2
3) SBAS7+Al(OH)3
4) TbH9+Ra35+SBAS1
5) TbH9+Ra35+SBAS2
6) TbH9+Ra35+SBAS7(Al(OH)3)
7) MTB72F in SBAS1
8) MTB72F in SBAS2
9) MTB72F in SBAS7+Al(OH)3
10) PBS
11) BCG
Dosage: 4 µg each of TbH9 and Ra35
8 µg MTB72F
Protocol: 1st immunization, 2nd immunization approximately 3 weeks later, 3rd immunization approximately two and a half weeks later.
Pre-challenge: DTH (delayed type hypersensitivity, used to determine antigenicity; 10 µg antigen)
Challenge: Aerosol with ~30 cfu Erdman strain
Post challenge monitoring: Weight loss
Death (6 months post challenge)
Results:
1. DTH
Positive reaction to the immunizing antigens. Reactions to individual antigens or the fusion protein were comparable. Skin test reactivity to PPD was only seen with the BCG immunized groups
2. Protection: Guinea pigs vaccinated with MTB72F fusion protein afforded protection compared to those immunized with a mixture of antigens (see FIG. 1).

Example 2

Mouse Vaccination with MTB72F Fusion Protein and Compositions with Individual Antigens As described above, mice were immunized with adjuvant alone (SBAS2, SBAS2', SBAS2", or SBAS6), MTB72F fusion protein in adjuvant, MTB72F DNA, MTB59F fusion protein in adjuvant, or TbH9, Ra35 and Ra12 antigen composition.

Figure 2A:
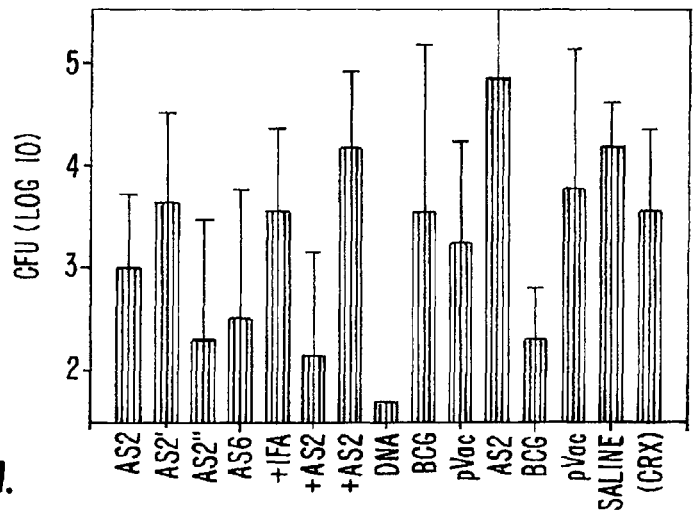
FIG. 2 shows CFUs from spleen cells (FIG. 2A) and lung cells (FIG. 2B) after immunization with MTB72F, MTB59F, MTB72F DNA, or a composition comprising Ra12, TbH9, and Ra35 antigens.
Figure 2B:
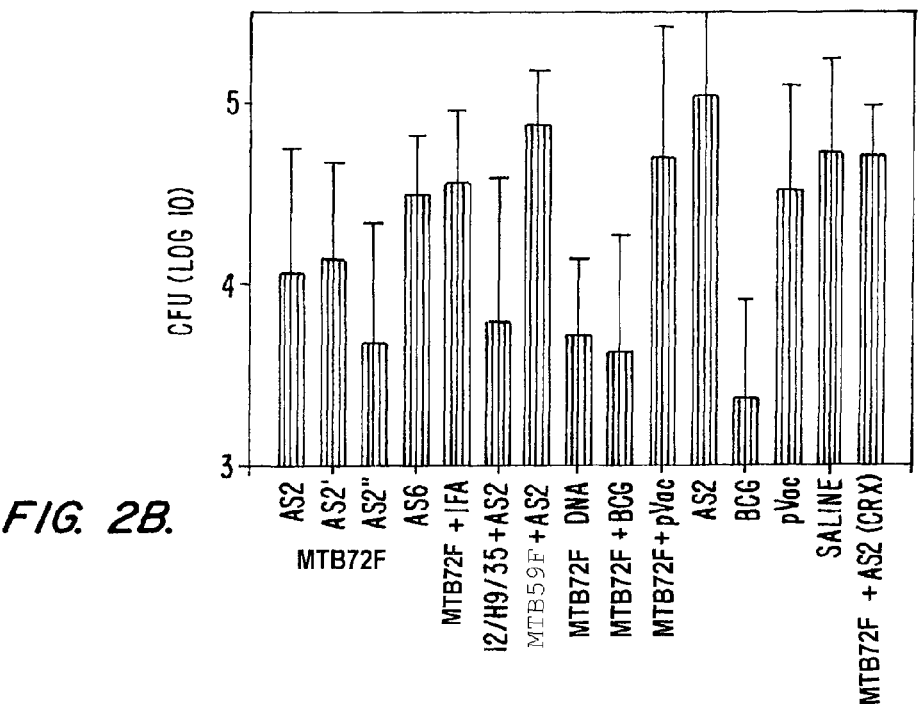
Figure 3:
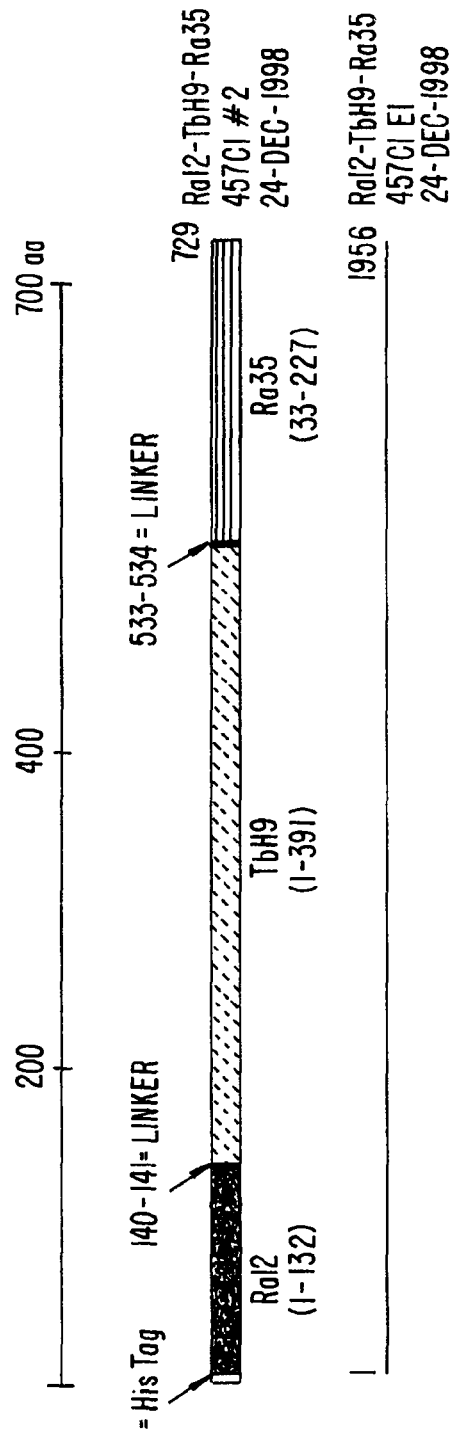
FIG. 3 shows a schematic diagram of MTB72F.

Methods:
Groups:
1) MTB72F+SBAS2
2) MTB72F+SBAS2'
3) MTB72F+SBAS2"
4) MTB72F+SBAS6
5) Ra12+TbH9+Ra35 in SBAS2
6) MTB59F in SBAS2
7) SBAS2
8) MTB72F+delipidated, deglycolipidated *M. vaccae*
9) MTB72F DNA
10) MTB72F+IFA
11) MTB72F+BCG
12) delipidated, deglycolipidated *M. vaccae*
13) BCG
14) Saline
15) MTB72F+SBAS2 (in house formulation)
8 animals per group
Immunization schedule: First immunization, second immunization approximately 3 weeks later; third immunization approximately three weeks later.
Aerosol challenge approximately three months after first does
Spleen or lung cells were isolated and cultured; count CFU of cultures approximately three weeks after plating.
Dose: 8 µg MTB72F, 6.56 µg MTB59F, or 1.52, 4.3, and 2.24 µg, respectively, of Ra12, TbH9, and Ra35, mixed.
Results:
Of the AS adjuvants, AS2"+MTB72F gave the best protection in both the spleen and lung in this set of experiments (see FIGS. 2A and 2B). MTB72F gave ~1 log better protection than MTB59F in both spleen and lung in this set of experiments, indicating that Ra12 provides additional benefit. Mixture of 12/H9/35+AS2 gave a better protection than MTB72F in this experiment. MTB72F DNA gave the best protection in this experiment, particularly in the spleen (>2 log). The protection was comparable in the lung to that seen with MTB72F protein+AS2", in this experiment.

Example 3

Guinea Pig Vaccination with MTB72F Fusion Protein and Compositions with Individual Antigens As described above, guinea pigs were immunized with adjuvant alone (SBAS2, SBAS2', SBAS2", or SBAS6), MTB72F fusion protein in adjuvant, MTB72F DNA, MTB59F fusion protein in adjuvant, or TbH9, Ra35 and Ra12 antigen composition.

Methods:
Groups:
1) MTB72F+SBAS2
2) MTB72F+SBAS2'
3) MTB72F+SBAS2"
4) MTB72F+SBAS6
5) Ra12+TbH9+Ra35 in SBAS2
6) MTB59F in SBAS2
7) SBAS2
8) MTB72F+pvac
9) MTB72F DNA
10) MTB72F+IFA
11) MTB72F+BCG
12) BCG
13) Saline
14) delipidated, deglycolipidated *M. vaccae*
Antigens:
Antigens were formulated on a molar equivalent
5 animals per group
Injection volume per dose is 250 µl (IM) containing

| | |
|---|---|
| MTB72F | 20 µg |
| Ra12, TbH9, Ra35 | 3.8, 10.8, and 5.6 µg |
| MTB59F | 16.4 µg |

Schedule:
1st immunization, 2nd immunization approximately three weeks later, 3rd immunization approximately three weeks later.

Challenge: ~one and one half months after first immunization.

Results:

| ~38 Wks post challenge | | |
| --- | --- | --- |
| Groups | Alive | State |
| G1. MTB72F + AS2 | 1/5 | [losing weight] |
| G2. MTB72F + AS2' | 2/5 | [not gaining weight] |
| G3. MTB72F + AS2" | 3/5 | [looking okay, but no weight gain] |
| G4. MTB72F + AS6 | 2/5 | [both these gaining weight] |
| G5. MTBRa12 + H9 + Ra35 + AS2 | 4/5 | [one maybe a bit peaked, but two gaining] |
| G6. MTB59F + AS2 | 2/5 | [both losing a little] |
| G7. AS2 | 2/5 | [both losing] |
| G8. MTB72F + pVac | 1/5 | [not looking too good] |
| G9. MTB72F DNA | 3/5 | [all holding steady] |
| G10. MTB72F + IFA | 2/5 | [doing okay] |
| G11. MTB72F + BCG | 5/5 | [eating very well] |
| G12. BCG | 4/5 | [doing fine] |
| G13. Saline | all dead | |
| G14. pVac | 2/5 | [not gaining weight] |

By 50 weeks post challenge, while 80% (4/5) of the guinea pigs immunized with BCG+Mtb72F were still alive, only 20% (1/5) of those immunized with BCG alone were alive. At 85 weeks, 4/5 of the guinea pigs immunized with BCG+Mtb72F were still alive and healthy (see FIG. 7).

Example 4

Long Term Protection

As described above, guinea pigs were immunized with adjuvant alone (AS2 or AS2"), MTB72F fusion protein in adjuvant, TbH9, Ra35 and Ra12 antigen composition, or a variety of individual antigens in adjuvant.

Methods

| GROUPS | ANTIGEN DOSE |
| --- | --- |
| 1. AS2" + MTB39 (TbH9) | 20 ug/250 ul (IM) |
| 2. AS2" + MTB8.4 (DPV) | 20 ug |
| 3. AS2" + MTB9.9 (MTI) | 20 ug |
| 4. AS2" + MTB41 (MTCC#2) | 20 ug |
| 5. AS2" + MTB40 (HTCC#1) | 20 ug |
| 6. AS2" + MTB9.8 (MSL) | 20 ug |
| 7. AS2" + MTB72F | 20 ug |
| 8. AS2" + Ra12 + TbH9 + Ra35 (molar equivalent) | 3.8 µg + 10.8 µg + 5.6 µg |
| 9. AS2" + MTB71F + MTB72F + HTCC#1 | 20 µg + 20 µg + 10 µg |
| 10. AS2" + Ra12 | 20 µg |
| 11. BCG | |
| 12. AS2" | |
| 13. AS2 + MTB72F | |
| 14. AS2 + Ra12 + TbH9 + Ra35 | |
| 15. AS2 | |

Example 5

Monkey Vaccination with MTB72F Fusion Protein and Compositions with Individual Antigens As described above, monkeys were immunized with MTB72F fusion protein in SBAS2 adjuvant, or MTB8.4 antigen composition in adjuvant, or a mixture of MTB72F and MTB8.4.

Methods:

Groups

1. Saline
2. BCG
3. MTB8.4/AS2
4. MTB72F/AS2
5. MTB72F/AS2 (one arm)+MTB8.4/AS2 (other arm)

40 µg each antigen

Results:

At 8 weeks post challenge, monkeys immunized with BCG are showing signs of infection Current data for 16 weeks post challenge reveals the following trend:

Groups immunized with MTB72F (4 and 5) are holding on their weights and have low ESR values compared to group 3 (MTB8.4 immunization) (Tables 1 and 2).

TABLE 1

Prophylactic Vaccine Study in Cynomolgus Monkeys with MTB8.4 and MTB72F formulated in AS2 20 Weeks Post Challenge

| Groups | ID | Net weight Change (kg) | Chest X-ray (onset) | Status |
| --- | --- | --- | --- | --- |
| AS2 | 1398K | −24% | Pn, bil, prog (wk 8) | Alive |
| | 4437B | −33% | Pn, bil, prog (wk 4) | Dead |
| | 2959G | −8.30% | Pn, bil, prog (wk 4) | Alive |
| | 605AE | −14.00% | Pn, rt, stable (wk 8) | Alive |
| BCG | 3436A | −15.00% | Neg | Alive |
| | 3642G | Plus 4.5% | Pn, rt, prog (wk 8) | Alive |
| | 1190H | 0% | Neg | Alive |
| | 1051I | −30% | Pn, rt, prog (wk 8) | Dead |
| MTB8.4 | 3665C | −25% | Pn, rt, prog (wk 8) | Dead |
| | 2200F | −18.00% | Pn, rt, stable (wk 8) | Alive |
| | 1654J | −33.00% | Pn, bil, prog (wk 4) | Dead |
| | 4141C | −33% | Pn, bil, prog (wk 4) | Dead |
| MTB72F | 3061C* | Died after IT challenge | | |
| | 1228G | Plus 3.6% | Bron, bil, stable for 3 mo (wk 8) | Alive |
| | 3462E | −2.20% | Neg | Alive |
| | 4254C | Plus 1.21 | Pn, rt, stable for 3 mo (wk 4) | Alive |
| MTB8.4 | 4496A | Plus 7% | Pn, rt, stable for 1 mo (wk 8) | Alive |
| MTB72F | 4422C | −39.00% | Pn, bil, prog (wk 4) | Dead |

TABLE 1-continued

Prophylactic Vaccine Study in Cynomolgus Monkeys with MTB8.4
and MTB72F formulated in AS2 20 Weeks Post Challenge

| Groups | ID | Net weight Change (kg) | Chest X-ray (onset) | Status |
|---|---|---|---|---|
| | 4416A | Plus 11% | Pn, rt, stable for 2 mo (wk 12) | Alive |
| | 2734E | Plus 12.5% | Susp infil rt, stable for 3 mo (wk 8) | Alive |

TABLE 2

Prophylactic Vaccine Study in Cynomolgus Monkeys
with MTB8.4 and MTB72F formulated in AS2

| Groups | ID | Wks Post Challenge ESR | | | | 16 wks Chest X-ray |
|---|---|---|---|---|---|---|
| | | 4 | 8 | 12 | 16 | |
| AS2 | 1398K | 3 | 3 | 10 | 19 | Pn, bil, progrsv |
| | 4437B | 10 | 20 | 3 | | Died |
| | 2959G | 6 | 3 | 3 | 0 | Pn, rt, progrsv |
| | 605AE | 1 | 4 | 7 | 3 | Pn, rt, stable |
| BCG | 3436A | 0 | 8 | 7 | 15 | Neg |
| | 3642G | 0 | 0 | 0 | 0 | Pn, rt, progrsv |
| | 1190H | 1 | 0 | 2 | 0 | Neg |
| | 1051I | 0 | 8 | 22 | 7 | Pn, bil, w/furt progrsn Died |
| MTB8.4 | 3665C | 12 | 30 | 19 | | Died |
| | 2200F | 1 | 7 | 2 | 0 | Pn, rt, progrsv |
| | 1654J | 20 | 8 | 21 | 7 | Pn, bil, w/fur progrsn |
| | 4141C | 13 | 8 | 2 | 15 | Pn, bil, w/fur progrsn |
| MTB72F | 3061C* | Died after IT challenge | | | | |
| | 1228G | 0 | 1 | 20 | 0 | Now stable |
| | 3462E | 0 | 0 | 0 | 0 | Neg |
| | 4254C | 13 | 0 | 0 | 0 | Pn, now stable |
| MTB8.4/ | 4496A | 5 | 1 | 0 | 5 | Pn, rt, w/furt prog |
| MTB72F | 4422C | 10 | 3 | 0 | | Died |
| | 4416A | 6 | 0 | 1 | 0 | Pn, now stable |
| | 2734E | 0 | 0 | 0 | 0 | Susp infil, now stable |

Example 6

BCG Priming Experiment in Monkeys 5 animals per group with four groups immunized with BCG and then rested, then immunized as described above and challenged. The following protocol will be used:

| Groups | # animals | Immunizing Antigen | Antigen Dose |
|---|---|---|---|
| 1. Nothing | 5 | AS2 | |
| 2. BCG | 5 | AS2 | |
| 3. BCG | 5 | MTB72F | 40 ug |
| 4. BCG | 4 | Ra12 + TbH9 + Ra35 | Molar equiv of antigens in MTB72F dose |
| 5. BCG | 4 | MTB72F + MTB71F + MTB40 | 40 ug MTB72F 40 ug MTB72F 20 ug MTB40 |

All antigens in formulated in AS2
Groups 4 and 5 have four animals each. Two of the BCG immunized monkeys died

| Groups | # animals | Immunizing Antigen | Antigens for T cell proliferation and cytokine production assays |
|---|---|---|---|
| 1. Nothing | 5 | AS2 | PHA, PPD, MTB72F, MTB71F, HTCC#1, DPV, MTCC#2, Ra12, TbH9, Ra35, MSL, MTI |
| 2. BCG | 5 | AS2 | PHA, PPD, MTB72F, MTB71F, HTCC#1, DPV, MTCC#2, Ra12, TbH9, Ra35, MSL, MTI |
| 3. BCG | 5 | MTB72F | PHA, PPD, MTB72F, Ra12, TbH9, Ra35 |
| 4. BCG | 4 | Ra12 + TbH9 + Ra35 | PHA, PPD, MTB72F, Ra12, TbH9, Ra35 |
| 5. BCG | 4 | MTB72F + MTB71F + MTB40 | PHA, PPD, MTB72F, MTB71F, HTCC#1, DPV, MTCC-2, Ra12, TbH9, Ra35, MSL, MTI |

Example 7

Construction of Ra35MutSA and MTB72FMutSA

Expression of MTB72F typically results in some breakdown products. In addition, the expression of the full-length sequences of the mature or full length form of Ra35 (Mtb32A) in E. coli has been difficult. The expressed product was only visible after immunoblotting with a polyclonal rabbit anti-Ra35 Ab indicative of low levels of protein expression. Even then, multiple specific species (bands) were detected indicative of auto-catalytic breakdown (degradation) of the recombinant antigen. This was presumed to be due to the expression of Ra35FL in E. coli as a biologically active form.

It has been previously shown that it was possible to express Ra35FL as two overlapping halves comprising the N-terminal (Ra35N-term, called Ra35) and C-term halves (Ra35C-term called Ra12). To enhance and stabilize the expression of the whole Ra35 molecule, a single point mutation was introduced at one of the residues within the active-site triad (substitution of Ser to Ala; see FIG. 6). This mutagenized form of Mtb32A can now be easily expressed at high levels in a stable form. In addition, to stabilize expression of MTB72F, a single nucleotide substitution (T to G, resulting in a Ser to Ala change at position 710 of the fusion polypeptide) was incorporated in the sequence of MTB72F at nucleotide position 2128 (see FIG. 5).

This stabilization is also readily accomplished by mutagenizing any one, any two, or all three of the three residues comprising the active site triad in Ra35FL, Ra35, or Mtb72F or other fusion proteins comprising Ra35 (His, Asp, or Ser). Mutagenesis can be performed using any technique known to one of skill in the art.

Example 8

Immunization of Mice with Ra35FLMutSA-TbH9 and MTB72FMutSA

Eight mice per group were immunized with the compositions listed below, which include the adjuvant AS2A. The mice were then challenged with Mycobacterium tuberculosis, and survival of the mice was measured.

| Group | Concentration of protein or DNA |
|---|---|
| 1. MTB72f protein | 1.5 mg/ml |
| 2. MTB72f DNA | 1.2 mg/ml |
| 3. MTB72f-85b protein | 0.6 mg/ml |
| 4. MTB72f-85b DNA | 1.1 mg/ml |
| 5. MTB72f-MTI protein | 1.3 mg/ml |
| 6. MTB72f-MTI DNA | 1.1 mg/ml |
| 7. MTB72f MutSA protein | 1.7 mg/ml |
| 8. MTB3AMutSA-TbH9 protein | 2.4 mg/ml |
| 9. BCG | |
| 10. AS2 | |
| 11. vector alone | 1.5 mg/ml |
| 12. saline | |

What is claimed is:

1. A polynucleotide comprising a nucleotide sequence encoding a fusion polypeptide, said fusion polypeptide comprising a first amino acid sequence having at least 95% sequence identity to SEQ ID NO: 14 and a second amino acid sequence having at least 95% sequence identity to SEQ ID NO:8.

2. The polynucleotide of claim 1, wherein the encoded fusion polypeptide further comprises a third amino acid sequence having at least 95% sequence identity to SEQ ID NO:10.

3. The polynucleotide of claim 1, wherein the encoded fusion polypeptide comprises an amino acid_sequence having at least 95% sequence identity to SEQ ID NO:20.

4. The polynucleotide of claim 1, wherein the encoded fusion polypeptide comprises an amino acid sequence having at least 95% sequence identity to SEQ ID NO:16.

5. The polynucleotide of claim 3, wherein the encoded fusion polypeptide consists of an amino acid sequence having at least 95% sequence identity to SEQ ID NO:20.

6. The polynucleotide of claim 4, wherein the encoded fusion polypeptide consists of an amino acid sequence having at least 95% sequence identity to SEQ ID NO: 16.

7. The polynucleotide of claim 1, wherein the encoded fusion polypeptide comprises the amino acid sequence of SEQ ID NO: 14 and the amino acid sequence of SEQ ID NO:8.

8. The polynucleotide of claim 7, wherein the encoded fusion polypeptide further comprises the amino acid sequence of SEQ ID NO: 10.

9. The polynucleotide of claim 1, wherein the encoded fusion polypeptide further comprises a 6 X histidine tag.

10. The polynucleotide of claim 1, wherein the encoded fusion polypeptide comprises SEQ ID NO:20.

11. The polynucleotide of claim 10, wherein the encoded fusion polypeptide consists of SEQ ID NO:20.

12. The polynucleotide of claim 11, wherein the encoded fusion polypeptide consists of SEQ ID NO:16.

13. A recombinant expression construct comprising the polynucleotide of claim 1.

14. The expression construct of claim 13, which is a viral vector.

15. The expression construct of claim 13, the polynucleotide comprising a nucleotide encoding a fusion polypeptide having at least 95% sequence identity to SEQ ID NO:20.

16. The expression construct of claim 13, the polynucleotide comprising a nucleotide encoding a fusion polypeptide having at least 95% sequence identity to SEQ ID NO:16.

17. The expression construct of claim 13, wherein the encoded fusion polypeptide consists of an amino acid sequence having at least 95% identity to SEQ ID NO:20.

18. The expression construct of claim 13, wherein the encoded fusion polypeptide consists of an amino acid sequence having at least 95% identity to SEQ ID NO:16.

19. A composition comprising the polynucleotide of claim 1 and a pharmaceutically acceptable carrier.

20. The composition of claim 19, wherein the encoded fusion polypeptide has at least 95% sequence identity to SEQ ID NO:20.

21. The composition of claim 19, wherein the encoded fusion polypeptide has at least 95% sequence identity to SEQ ID NO: 16.

22. The composition of claim 19, further comprising an adjuvant.

23. The composition of claim 20, further comprising an adjuvant.

24. The composition of claim 21, further comprising an adjuvant.

25. The composition of claim 19, wherein the encoded fusion polypeptide comprises an amino acid sequence having at least 95% sequence identity to SEQ ID NO:20.

26. The composition of claim 19, wherein the encoded fusion polypeptide comprises an amino acid sequence having at least 95% sequence identity to SEQ ID NO:16.

27. The composition of claim 26, further comprising an adjuvant.

28. The composition of claim 25, further comprising an adjuvant.

29. A method of recombinantly making a fusion protein, the method comprising the step of expressing the polynucleotide of claim 1 in a host cell.

30. The method of claim 29, wherein the fusion protein comprises an amino acid sequence having at least 95% sequence identity to SEQ ID NO:20.

31. The method of claim 29, wherein the fusion protein comprises an amino acid sequence having at least 95% sequence identity to SEQ ID NO:16.

32. The method of claim 29, wherein the fusion protein consists of an amino acid sequence having at least 95% sequence identity to SEQ ID NO:20.

33. The method of claim 29, wherein the fusion protein consists of an amino acid sequence having at least 95% sequence identity to SEQ ID NO: 16.

34. An isolated host cell transfected with an expression vector comprising a polynucleotide comprising a nucleotide sequence encoding a fusion polypeptide, said fusion polypeptide comprising a first amino acid sequence having at least 95% sequence identity to SEQ ID NO:14 and a second amino acid sequence having at least 95% sequence identity to SEQ ID NO:8.

35. The host cell of claim 34, wherein the encoded fusion polypeptide further comprises a third amino acid sequence having at least 95% sequence identity to SEQ ID NO:10.

36. The host cell of claim 34, wherein the encoded fusion polypeptide has at least 95% sequence identity to SEQ ID NO:20.

37. The host cell of claim 34, wherein the encoded fusion polypeptide has at least 95% sequence identity to SEQ ID NO:16.

38. The host cell of claim 34, wherein the encoded fusion polypeptide comprises the amino acid sequence of SEQ ID NO: 14 and the amino acid sequence of SEQ ID NO:8.

39. The host cell of claim 37, wherein the encoded fusion polypeptide further comprises the amino acid sequence of SEQ ID NO: 10.

40. The host cell of claim 34, wherein the encoded fusion polypeptide comprises SEQ ID NO:20.

41. The host cell of claim 40, wherein the encoded fusion polypeptide consists of SEQ ID NO:20.

42. The host cell of claim 34, wherein the encoded fusion polypeptide comprises a sequence having at least 95% sequence identity to SEQ ID NO:20.

43. The host cell of claim 34, wherein the encoded fusion polypeptide comprises a sequence having at least 95% sequence identity to SEQ ID NO:16.

44. The host cell of claim 34, wherein the host cell is a *Bacillus*-Calmette-Guerrin.

45. The host cell of claim 36, wherein the host cell is a *Bacillus*-Calmette-Guerrin.

46. The host cell of claim 37, wherein the host cell is a *Bacillus*-Calmette-Guerrin.

47. The host cell of claim 43, wherein the host cell is a *Bacillus*-Calmette-Guerrin.

48. The host cell of claim 43, wherein the host cell is a *Bacillus*-Calmette-Guerrin.

* * * * *

SEQUENCE LISTING

```
<160> NUMBER OF SEQ ID NOS: 50

<210> SEQ ID NO 1
<211> LENGTH: 1872
<212> TYPE: DNA
<213> ORGANISM: Mycobacterium tuberculosis
<220> FEATURE:
<223> OTHER INFORMATION: MTB32A (Ra35FL)
<220> FEATURE:
<221> NAME/KEY: modified_base
<222> LOCATION: (1)..(1872)
<223> OTHER INFORMATION: n = g, a, c or t

<400> SEQUENCE: 1
gactacgttg gtgtagaaaa atcctgccgc ccggacccttt aaggctggga caatttctga      60
tagctacccc gacacaggag gttacgggat gagcaattcg cgccgccgct cactcaggtg     120
gtcatggttg ctgagcgtgc tggctgccgt cgggctgggc ctggccacgg cgccggccca     180
ggcggccccg ccggccttgt cgcaggaccg gttcgccgac ttccccgcgc tgcccctcga     240
cccgtccgcg atggtcgccc aagtggcgcc acaggtggtc aacatcaaca ccaaactggg     300
ctacaacaac gccgtgggcg ccgggaccgg catcgtcatc gatcccaacg gtgtcgtgct     360
gaccaacaac cacgtgatcg cgggcgccac cgacatcaat gcgttcagcg tcggctccgg     420
ccaaacctac ggcgtcgatg tggtcgggta tgaccgcacc caggatgtcg cggtgctgca     480
gctgcgcggt gccggtggcc tgccgtcggc ggcgatcggt ggcggcgtcg cggttggtga     540
gcccgtcgtc gcgatgggca acagcggtgg gcagggcgga acgcccgtg cggtgcctgg     600 cagggtggtc gcgctcggcc aaaccgtgca ggcgtcggat tcgctgaccg gtgccgaaga     660
gacattgaac gggttgatcc agttcgatgc cgcaatccag cccggtgatt cgggcgggcc     720
cgtcgtcaac ggcctaggac aggtggtcgg tatgaacacg ccgcgtccg ataacttcca     780 gctgtcccag ggtgggcagg gattcgccat tccgatcggg caggcgatgg cgatcgcgg     840 ccaaatccga tcggtgggg ggtcacccac cgttcatatc gggcctaccg ccttcctcgg     900
cttgggtgtt gtcgacaaca acggcaacgg cgcacgagtc caacgcgtgg tcggaagcgc     960
tccggcggca agtctcggca tctccaccgg cgacgtgatc accgcggtcg acggcgctcc    1020
gatcaactcg gccaccgcga tggcggacgc gcttaacggg catcatcccg tgacgtcat    1080 ctcggtgaac tggcaaacca agtcgggcgg cacgcgtaca gggaacgtga cattggccga    1140
gggacccccg gcctgatttg tcgcggatac caccgccgg ccggccaatt ggattggcgc    1200
cagccgtgat tgccgcgtga gccccccgagt tccgtctccc gtgcgcgtgg cattgtggaa    1260
```

```
gcaatgaacg aggcagaaca cagcgttgag caccctcccg tgcagggcag ttacgtcgaa    1320
ggcggtgtgg tcgagcatcc ggatgccaag gacttcggca gcgccgccgc cctgcccgcc    1380
gatccgacct ggtttaagca cgccgtcttc tacgaggtgc tggtccgggc gttcttcgac    1440
gccagcgcgg acggttccgn cgatctgcgt ggactcatcg atcgcctcga ctacctgcag    1500
tggcttggca tcgactgcat ctgttgccgc cgttcctacg actcaccgct gcgcgacggc    1560
ggttacgaca ttcgcgactt ctacaaggtg ctgcccgaat cggcaccgt cgacgatttc    1620 gtcgccctgg tcgacaccgc tcaccggcga ggtatccgca tcatcaccga cctggtgatg    1680
aatcacacct cggagtcgca cccctggttt caggagtccc gccgcgaccc agacggaccg    1740
tacggtgact attacgtgtg gagcgacacc agcgagcgct acaccgacgc ccggatcatc    1800
ttcgtcgaca ccgaagagtc gaactggtca ttcgatcctg tccgccgaca gttnctactg    1860
gcaccgattc tt                                                        1872
```

<210> SEQ ID NO 2
<211> LENGTH: 355
<212> TYPE: PRT
<213> ORGANISM: Mycobacterium tuberculosis
<220> FEATURE:
<223> OTHER INFORMATION: MTB32A (Ra35FL)

<400> SEQUENCE: 2

```
Met Ser Asn Ser Arg Arg Arg Ser Leu Arg Trp Ser Trp Leu Leu Ser
  1               5                  10                  15

Val Leu Ala Ala Val Gly Leu Gly Leu Ala Thr Ala Pro Ala Gln Ala
                 20                  25                  30

Ala Pro Pro Ala Leu Ser Gln Asp Arg Phe Ala Asp Phe Pro Ala Leu
             35                  40                  45

Pro Leu Asp Pro Ser Ala Met Val Ala Gln Val Ala Pro Gln Val Val
         50                  55                  60

Asn Ile Asn Thr Lys Leu Gly Tyr Asn Asn Ala Val Gly Ala Gly Thr
 65                  70                  75                  80

Gly Ile Val Ile Asp Pro Asn Gly Val Val Leu Thr Asn Asn His Val
                 85                  90                  95

Ile Ala Gly Ala Thr Asp Ile Asn Ala Phe Ser Val Gly Ser Gly Gln
            100                 105                 110

Thr Tyr Gly Val Asp Val Val Gly Tyr Asp Arg Thr Gln Asp Val Ala
        115                 120                 125

Val Leu Gln Leu Arg Gly Ala Gly Gly Leu Pro Ser Ala Ala Ile Gly
    130                 135                 140

Gly Gly Val Ala Val Gly Glu Pro Val Val Ala Met Gly Asn Ser Gly
145                 150                 155                 160

Gly Gln Gly Gly Thr Pro Arg Ala Val Pro Gly Arg Val Val Ala Leu
                165                 170                 175

Gly Gln Thr Val Gln Ala Ser Asp Ser Leu Thr Gly Ala Glu Glu Thr
            180                 185                 190

Leu Asn Gly Leu Ile Gln Phe Asp Ala Ala Ile Gln Pro Gly Asp Ser
        195                 200                 205

Gly Gly Pro Val Val Asn Gly Leu Gly Gln Val Val Gly Met Asn Thr
    210                 215                 220

Ala Ala Ser Asp Asn Phe Gln Leu Ser Gln Gly Gly Gln Gly Phe Ala
225                 230                 235                 240

Ile Pro Ile Gly Gln Ala Met Ala Ile Ala Gly Gln Ile Arg Ser Gly
                245                 250                 255
```

```
Gly Gly Ser Pro Thr Val His Ile Gly Pro Thr Ala Phe Leu Gly Leu
            260                 265                 270

Gly Val Val Asp Asn Asn Gly Asn Gly Ala Arg Val Gln Arg Val Val
            275                 280                 285

Gly Ser Ala Pro Ala Ala Ser Leu Gly Ile Ser Thr Gly Asp Val Ile
            290                 295                 300

Thr Ala Val Asp Gly Ala Pro Ile Asn Ser Ala Thr Ala Met Ala Asp
305                 310                 315                 320

Ala Leu Asn Gly His His Pro Gly Asp Val Ile Ser Val Asn Trp Gln
                325                 330                 335

Thr Lys Ser Gly Gly Thr Arg Thr Gly Asn Val Thr Leu Ala Glu Gly
            340                 345                 350

Pro Pro Ala
        355

<210> SEQ ID NO 3
<211> LENGTH: 1002
<212> TYPE: DNA
<213> ORGANISM: Mycobacterium tuberculosis
<220> FEATURE:
<223> OTHER INFORMATION: MTB32A (Ra35 mature)

<400> SEQUENCE: 3
catatgcatc accatcacca tcacgccccg ccggccttgt cgcaggaccg gttcgccgac      60
ttccccgcgc tgcccctcga cccgtccgcg atggtcgccc aagtgggggcc acaggtggtc    120 aacatcaaca ccaaactggg ctacaacaac gccgtgggcg ccgggaccgg catcgtcatc    180
gatcccaacg gtgtcgtgct gaccaacaac cacgtgatcg cgggcgccac cgacatcaat    240
gcgttcagcg tcggctccgg ccaaacctac ggcgtcgatg tggtcgggta tgaccgcacc    300
caggatgtcg cggtgctgca gctgcgcggt gccggtggcc tgccgtcggc ggcgatcggt    360
ggcggcgtcg cggttggtga gcccgtcgtc gcgatgggca acagcggtgg gcagggcgga    420
acgccccgtg cggtgcctgg cagggtggtc gcgctcggcc aaaccgtgca ggcgtcggat    480
tcgctgaccg gtgccgaaga gacattgaac gggttgatcc agttcgatgc gcgatccag    540 cccggtgagg cgggcgggcc gtcgtcaac ggcctaggac aggtggtcgg tatgaacacg    600
gccgcgtccg ataacttcca gctgtcccag ggtgggcagg gattcgccat tccgatcggg    660
caggcgatgg cgatcgcggg ccagatccga tcgggtgggg ggtcacccac cgttcatatc    720
gggcctaccg ccttcctcgg cttgggtgtt gtcgacaaca acggcaacgg cgcacgagtc    780
caacgcgtgg tcgggagcgc tccggcggca agtctcggca tctccaccgg cgacgtgatc    840
accgcggtcg acggcgctcc gatcaactcg gccaccgcga tggcggacgc gcttaacggg    900
catcatcccg gtgacgtcat ctcggtgacc tggcaaacca gtcgggcgg cacgcgtaca    960 gggaacgtga cattggccga gggaccccg gcctgagaat tc                       1002

<210> SEQ ID NO 4
<211> LENGTH: 330
<212> TYPE: PRT
<213> ORGANISM: Mycobacterium tuberculosis
<220> FEATURE:
<223> OTHER INFORMATION: MTB32A (Ra35 mature)

<400> SEQUENCE: 4

Met His His His His His Ala Pro Pro Ala Leu Ser Gln Asp Arg
  1               5                  10                  15

Phe Ala Asp Phe Pro Ala Leu Pro Leu Asp Pro Ser Ala Met Val Ala
            20                  25                  30
```

```
Gln Val Gly Pro Gln Val Val Asn Ile Asn Thr Lys Leu Gly Tyr Asn
            35                  40                  45

Asn Ala Val Gly Ala Gly Thr Gly Ile Val Ile Asp Pro Asn Gly Val
        50                  55                  60

Val Leu Thr Asn Asn His Val Ile Ala Gly Thr Asp Ile Asn Ala
    65                  70                  75                  80

Phe Ser Val Gly Ser Gly Gln Thr Tyr Gly Val Asp Val Val Gly Tyr
                85                  90                  95

Asp Arg Thr Gln Asp Val Ala Val Leu Gln Leu Arg Gly Ala Gly Gly
                    100                 105                 110

Leu Pro Ser Ala Ala Ile Gly Gly Val Ala Val Gly Glu Pro Val
            115                 120                 125

Val Ala Met Gly Asn Ser Gly Gly Gln Gly Gly Thr Pro Arg Ala Val
    130                 135                 140

Pro Gly Arg Val Val Ala Leu Gly Gln Thr Val Gln Ala Ser Asp Ser
145                 150                 155                 160

Leu Thr Gly Ala Glu Glu Thr Leu Asn Gly Leu Ile Gln Phe Asp Ala
                165                 170                 175

Ala Ile Gln Pro Gly Asp Ser Gly Pro Val Val Asn Gly Leu Gly
            180                 185                 190

Gln Val Val Gly Met Asn Thr Ala Ala Ser Asp Asn Phe Gln Leu Ser
        195                 200                 205

Gln Gly Gly Gln Gly Phe Ala Ile Pro Ile Gly Gln Ala Met Ala Ile
    210                 215                 220

Ala Gly Gln Ile Arg Ser Gly Gly Ser Pro Thr Val His Ile Gly
225                 230                 235                 240

Pro Thr Ala Phe Leu Gly Leu Gly Val Val Asp Asn Asn Gly Asn Gly
                245                 250                 255

Ala Arg Val Gln Arg Val Val Gly Ser Ala Pro Ala Ala Ser Leu Gly
            260                 265                 270

Ile Ser Thr Gly Asp Val Ile Thr Ala Val Asp Gly Ala Pro Ile Asn
        275                 280                 285

Ser Ala Thr Ala Met Ala Asp Ala Leu Asn Gly His His Pro Gly Asp
    290                 295                 300

Val Ile Ser Val Thr Trp Gln Thr Lys Ser Gly Gly Thr Arg Thr Gly
305                 310                 315                 320

Asn Val Thr Leu Ala Glu Gly Pro Pro Ala
                325                 330

<210> SEQ ID NO 5
<211> LENGTH: 1002
<212> TYPE: DNA
<213> ORGANISM: Artificial Sequence
<220> FEATURE:
<223> OTHER INFORMATION: Description of Artificial Sequence:Ra35FLMutSA

<400> SEQUENCE: 5
catatgcatc accatcacca tcacgccccg ccggccttgt cgcaggaccg gttcgccgac      60
ttccccgcgc tgcccctcga cccgtccgcg atggtcgccc aagtggggcc acaggtggtc     120
aacatcaaca ccaaactggg ctacaacaac gccgtgggcg ccgggaccgg catcgtcatc     180
gatcccaacg gtgtcgtgct gaccaacaac cacgtgatcg cgggcgccac cgacatcaat     240
gcgttcagcg tcggctccgg ccaaacctac ggcgtcgatg tggtcgggta tgaccgcacc     300
caggatgtcg cggtgctgca gctgcgcggt gccggtggcc tgccgtcggc ggcgatcggt     360
```

-continued

```
ggcggcgtcg cggttggtga gcccgtcgtc gcgatgggca acagcggtgg gcagggcgga      420
acgccccgtg cggtgcctgg cagggtggtc gcgctcggcc aaaccgtgca ggcgtcggat      480
tcgctgaccg gtgccgaaga gacattgaac gggttgatcc agttcgatgc cgcgatccag      540
cccggtgatg cgggcgggcc cgtcgtcaac ggcctaggac aggtggtcgg tatgaacacg      600
gccgcgtccg ataacttcca gctgtcccag ggtgggcagg gattcgccat tccgatcggg      660
caggcgatgg cgatcgcggg ccagatccga tcggtggggg ggtcacccac cgttcatatc      720
gggcctaccg ccttcctcgg cttgggtgtt gtcgacaaca acggcaacgg cgcacgagtc      780
caacgcgtgg tcgggagcgc tccggcggca agtctcggca tctccaccgg cgacgtgatc      840
accgcggtcg acggcgctcc gatcaactcg gccaccgcga tggcggacgc gcttaacggg      900
catcatcccg gtgacgtcat ctcggtgacc tggcaaacca gtcgggcgg cacgcgtaca       960 gggaacgtga cattggccga gggaccccg gcctgagaat tc                         1002
```

<210> SEQ ID NO 6
<211> LENGTH: 330
<212> TYPE: PRT
<213> ORGANISM: Artificial Sequence
<220> FEATURE:
<223> OTHER INFORMATION: Description of Artificial Sequence:Ra35FLMutSA

<400> SEQUENCE: 6

```
Met His His His His His His Ala Pro Pro Ala Leu Ser Gln Asp Arg
  1               5                  10                  15

Phe Ala Asp Phe Pro Ala Leu Pro Leu Asp Pro Ser Ala Met Val Ala
                 20                  25                  30

Gln Val Gly Pro Gln Val Val Asn Ile Asn Thr Lys Leu Gly Tyr Asn
             35                  40                  45

Asn Ala Val Gly Ala Gly Thr Gly Ile Val Ile Asp Pro Asn Gly Val
         50                  55                  60

Val Leu Thr Asn Asn His Val Ile Ala Gly Ala Thr Asp Ile Asn Ala
 65                  70                  75                  80

Phe Ser Val Gly Ser Gly Gln Thr Tyr Gly Val Asp Val Val Gly Tyr
                 85                  90                  95

Asp Arg Thr Gln Asp Val Ala Val Leu Gln Leu Arg Gly Ala Gly Gly
            100                 105                 110

Leu Pro Ser Ala Ala Ile Gly Gly Gly Val Ala Val Gly Glu Pro Val
        115                 120                 125

Val Ala Met Gly Asn Ser Gly Gly Gln Gly Gly Thr Pro Arg Ala Val
    130                 135                 140

Pro Gly Arg Val Val Ala Leu Gly Gln Thr Val Gln Ala Ser Asp Ser
145                 150                 155                 160

Leu Thr Gly Ala Glu Glu Thr Leu Asn Gly Leu Ile Gln Phe Asp Ala
                165                 170                 175

Ala Ile Gln Pro Gly Asp Ala Gly Gly Pro Val Asn Gly Leu Gly
            180                 185                 190

Gln Val Val Gly Met Asn Thr Ala Ala Ser Asp Asn Phe Gln Leu Ser
        195                 200                 205

Gln Gly Gly Gln Gly Phe Ala Ile Pro Ile Gly Gln Ala Met Ala Ile
    210                 215                 220

Ala Gly Gln Ile Arg Ser Gly Gly Ser Pro Thr Val His Ile Gly
225                 230                 235                 240

Pro Thr Ala Phe Leu Gly Leu Gly Val Val Asp Asn Asn Gly Asn Gly
                245                 250                 255
```

```
Ala Arg Val Gln Arg Val Val Gly Ser Ala Pro Ala Ala Ser Leu Gly
            260                 265                 270

Ile Ser Thr Gly Asp Val Ile Thr Ala Val Asp Gly Ala Pro Ile Asn
        275                 280                 285

Ser Ala Thr Ala Met Ala Asp Ala Leu Asn Gly His His Pro Gly Asp
    290                 295                 300

Val Ile Ser Val Thr Trp Gln Thr Lys Ser Gly Thr Arg Thr Gly
305                 310                 315                 320

Asn Val Thr Leu Ala Glu Gly Pro Pro Ala
                325                 330
```

<210> SEQ ID NO 7
<211> LENGTH: 585
<212> TYPE: DNA
<213> ORGANISM: Mycobacterium tuberculosis
<220> FEATURE:
<223> OTHER INFORMATION: Ra35 N-terminus of MTB32A (Ra35FL)

<400> SEQUENCE: 7

```
gccccgccgg ccttgtcgca ggaccggttc gccgacttcc ccgcgctgcc cctcgacccg      60
tccgcgatgg tcgcccaagt gggggccaca ggtggtcaaca tcaacaccaa actgggctac    120
aacaacgccg tgggcgccgg gaccggcatc gtcatcgatc ccaacggtgt cgtgctgacc    180
aacaaccacg tgatcgcggg cgccaccgac atcaatgcgt tcagcgtcgg ctccggccaa    240
acctacggcg tcgatgtggt cgggtatgac cgcacccagg atgtcgcggt gctgcagctg    300
cgcggtgccg gtggcctgcc gtcggcggcg atcggtggcg gcgtcgcggt tggtgagccc    360
gtcgtcgcga tgggcaacag cggtgggcag ggcggaacgc cccgtgcggt gcctggcagg    420
gtggtcgcgc tcgccaaac cgtgcaggcg tcggattcgc tgaccggtgc cgaagagaca    480
ttgaacgggt tgatccagtt cgatgccgcg atccagcccg tgaggcggg cgggcccgtc    540
gtcaacggcc taggacaggt ggtcggtatg aacacggccg cgtcc                    585
```

<210> SEQ ID NO 8
<211> LENGTH: 195
<212> TYPE: PRT
<213> ORGANISM: Mycobacterium tuberculosis
<220> FEATURE:
<223> OTHER INFORMATION: Ra35 N-terminus of MTB32A (Ra35FL)

<400> SEQUENCE: 8

```
Ala Pro Pro Ala Leu Ser Gln Asp Arg Phe Ala Asp Phe Pro Ala Leu
  1               5                  10                  15

Pro Leu Asp Pro Ser Ala Met Val Ala Gln Val Gly Pro Gln Val Val
                20                  25                  30

Asn Ile Asn Thr Lys Leu Gly Tyr Asn Asn Ala Val Gly Ala Gly Thr
            35                  40                  45

Gly Ile Val Ile Asp Pro Asn Gly Val Val Leu Thr Asn Asn His Val
        50                  55                  60

Ile Ala Gly Ala Thr Asp Ile Asn Ala Phe Ser Val Gly Ser Gly Gln
 65                  70                  75                  80

Thr Tyr Gly Val Asp Val Val Gly Tyr Asp Arg Thr Gln Asp Val Ala
                85                  90                  95

Val Leu Gln Leu Arg Gly Ala Gly Gly Leu Pro Ser Ala Ala Ile Gly
                100                 105                 110

Gly Gly Val Ala Val Gly Glu Pro Val Ala Met Gly Asn Ser Gly
            115                 120                 125

Gly Gln Gly Gly Thr Pro Arg Ala Val Pro Gly Arg Val Val Ala Leu
```

```
                        130                 135                 140
Gly Gln Thr Val Gln Ala Ser Asp Ser Leu Thr Gly Ala Glu Glu Thr
145                 150                 155                 160

Leu Asn Gly Leu Ile Gln Phe Asp Ala Ala Ile Gln Pro Gly Asp Ser
                165                 170                 175

Gly Gly Pro Val Val Asn Gly Leu Gly Gln Val Val Gly Met Asn Thr
                180                 185                 190

Ala Ala Ser
        195

<210> SEQ ID NO 9
<211> LENGTH: 447
<212> TYPE: DNA
<213> ORGANISM: Mycobacterium tuberculosis
<220> FEATURE:
<223> OTHER INFORMATION: Ra12 or MTBRa12 C-terminus of MTB32A (Ra35FL)

<400> SEQUENCE: 9
cggtatgaac acggccgcgt ccgataactt ccagctgtcc cagggtgggc agggattcgc      60
cattccgatc gggcaggcga tggcgatcgc gggccagatc cgatcgggtg ggggtcacc     120 caccgttcat atcgggccta ccgccttcct cggcttgggt gttgtcgaca caacggcaa     180 cggcgcacga gtccaacgcg tggtcgggag cgctccggcg gcaagtctcg gcatctccac     240
cggcgacgtg atcaccgcgg tcgacggcgc tccgatcaac tcggccaccg cgatggcgga     300
cgcgcttaac gggcatcatc ccggtgacgt catctcggtg aactggcaaa ccaagtcggg     360
cggcacgcgt acagggaacg tgacattggc cgagggaccc ccggcctgat ttcgtcgygg     420
ataccacccg ccggccggcc aattgga                                         447

<210> SEQ ID NO 10
<211> LENGTH: 132
<212> TYPE: PRT
<213> ORGANISM: Mycobacterium tuberculosis
<220> FEATURE:
<223> OTHER INFORMATION: Ra 12 or MTBRa12 C-terminus of MTB32A (Ra35FL)

<400> SEQUENCE: 10

Thr Ala Ala Ser Asp Asn Phe Gln Leu Ser Gln Gly Gly Gln Gly Phe
1               5                  10                  15

Ala Ile Pro Ile Gly Gln Ala Met Ala Ile Ala Gly Gln Ile Arg Ser
                20                  25                  30

Gly Gly Gly Ser Pro Thr Val His Ile Gly Pro Thr Ala Phe Leu Gly
            35                  40                  45

Leu Gly Val Val Asp Asn Asn Gly Asn Gly Ala Arg Val Gln Arg Val
        50                  55                  60

Val Gly Ser Ala Pro Ala Ala Ser Leu Gly Ile Ser Thr Gly Asp Val
65                  70                  75                  80

Ile Thr Ala Val Asp Gly Ala Pro Ile Asn Ser Ala Thr Ala Met Ala
                85                  90                  95

Asp Ala Leu Asn Gly His His Pro Gly Asp Val Ile Ser Val Asn Trp
                100                 105                 110

Gln Thr Lys Ser Gly Gly Thr Arg Thr Gly Asn Val Thr Leu Ala Glu
            115                 120                 125

Gly Pro Pro Ala
        130

<210> SEQ ID NO 11
<211> LENGTH: 851
```

```
<212> TYPE: DNA
<213> ORGANISM: Mycobacterium tuberculosis
<220> FEATURE:
<223> OTHER INFORMATION: MTB39 (TbH9)
<220> FEATURE:
<221> NAME/KEY: modified_base
<222> LOCATION: (767)
<223> OTHER INFORMATION: n = g, a, c or t

<400> SEQUENCE: 11
ctgcaggtgg gcgtggatga gcgtcaccgc ggggcaggcc gagctgaccg ccgcccaggt      60
ccgggttgct gcggcggcct acgagacggc gtatgggctg acggtgcccc cgccggtgat    120
cgccgagaac cgtgctgaac tgatgattct gatagcgacc aacctcttgg ggcaaaacac    180
cccggcgatc gcggtcaacg aggccgaata cggcgagatg tgggcccaag acgccgccgc    240
gatgtttggc tacgccgcgg cgacggcgac ggcgacgggc acgttgctgc cgttcgagga    300
ggcgccggag atgaccagcg cgggtgggct cctcgagcag gccgccgcgg tcgaggaggc    360
ctccgacacc gccgcggcga accagttgat gaacaatgtg ccccaggcgc tgaaacagtt    420
ggcccagccc acgcagggca ccacgccttc ttccaagctg ggtggcctgt ggaagacggt    480
ctcgccgcat cggtcgccga tcagcaacat ggtgtcgatg ccaacaacc acatgtcgat     540
gaccaactcg ggtgtgtcga tgaccaacac cttgagctcg atgttgaagg ctttgctcc     600
ggcggcggcc gcccaggccg tgcaaaccgc ggcgcaaaac ggggtccggg cgatgagctc    660
gctgggcagc tcgctgggtt cttcgggtct gggcggtggg gtggccgcca acttgggtcg    720
ggcggcctcg gtacggtatg gtcaccggga tggcggaaaa tatgcanagt ctggtcggcg    780
gaacggtggt ccggcgtaag gtttaccccc gttttctgga tgcggtgaac ttcgtcaacg    840
gaaacagtta c                                                        851

<210> SEQ ID NO 12
<211> LENGTH: 263
<212> TYPE: PRT
<213> ORGANISM: Mycobacterium tuberculosis
<220> FEATURE:
<223> OTHER INFORMATION: MTB39 (TbH9)
<220> FEATURE:
<221> NAME/KEY: MOD_RES
<222> LOCATION: (254)
<223> OTHER INFORMATION: Xaa = any amino acid

<400> SEQUENCE: 12

Val Ala Trp Met Ser Val Thr Ala Gly Gln Ala Glu Leu Thr Ala Ala
  1               5                  10                  15

Gln Val Arg Val Ala Ala Ala Ala Tyr Glu Thr Ala Tyr Gly Leu Thr
                 20                  25                  30

Val Pro Pro Val Ile Ala Glu Asn Arg Ala Glu Leu Met Ile Leu
             35                  40                  45

Ile Ala Thr Asn Leu Leu Gly Gln Asn Thr Pro Ala Ile Ala Val Asn
     50                  55                  60

Glu Ala Glu Tyr Gly Glu Met Trp Ala Gln Asp Ala Ala Ala Met Phe
 65                  70                  75                  80

Gly Tyr Ala Ala Ala Thr Ala Thr Ala Thr Ala Thr Leu Leu Pro Phe
                 85                  90                  95

Glu Glu Ala Pro Glu Met Thr Ser Ala Gly Gly Leu Leu Glu Gln Ala
            100                 105                 110

Ala Ala Val Glu Glu Ala Ser Asp Thr Ala Ala Ala Asn Gln Leu Met
        115                 120                 125

Asn Asn Val Pro Gln Ala Leu Lys Gln Leu Ala Gln Pro Thr Gln Gly
```

```
                    130                 135                 140
Thr Thr Pro Ser Ser Lys Leu Gly Gly Leu Trp Lys Thr Val Ser Pro
145                 150                 155                 160

His Arg Ser Pro Ile Ser Asn Met Val Ser Met Ala Asn Asn His Met
                165                 170                 175

Ser Met Thr Asn Ser Gly Val Ser Met Thr Asn Thr Leu Ser Ser Met
            180                 185                 190

Leu Lys Gly Phe Ala Pro Ala Ala Ala Ala Gln Ala Val Gln Thr Ala
        195                 200                 205

Ala Gln Asn Gly Val Arg Ala Met Ser Ser Leu Gly Ser Ser Leu Gly
    210                 215                 220

Ser Ser Gly Leu Gly Gly Gly Val Ala Ala Asn Leu Gly Arg Ala Ala
225                 230                 235                 240

Ser Val Arg Tyr Gly His Arg Asp Gly Gly Lys Tyr Ala Xaa Ser Gly
                245                 250                 255

Arg Arg Asn Gly Gly Pro Ala
            260

<210> SEQ ID NO 13
<211> LENGTH: 3058
<212> TYPE: DNA
<213> ORGANISM: Mycobacterium tuberculosis
<220> FEATURE:
<223> OTHER INFORMATION: MTB39 (TbH9FL)

<400> SEQUENCE: 13
gatcgtaccc gtgcgagtgc tcgggccgtt tgaggatgga gtgcacgtgt ctttcgtgat      60
ggcataccca gagatgttgg cggcggcggc tgacaccctg cagagcatcg gtgctaccac     120
tgtggctagc aatgccgctg cggcggcccc gacgactggg gtggtgcccc cgctgccga     180 tgaggtgtcg gcgctgactg cggcgcactt cgccgcacat gcggcgatgt atcagtccgt     240
gagcgctcgg gctgctgcga ttcatgacca gttcgtggcc acccttgcca gcagcgccag     300
ctcgtatgcg gccactgaag tcgccaatgc ggcggcggcc agctaagcca ggaacagtcg     360
gcacgagaaa ccacgagaaa tagggacacg taatggtgga tttcggggcg ttaccaccgg     420
agatcaactc cgcgaggatg tacgccggcc cgggttcggc ctcgctggtg gccgcggctc     480
agatgtggga cagcgtggcg agtgacctgt tttcggccgc gtcggcgttt cagtcggtgg     540
tctggggtct gacggtgggg tcgtggatag gttcgtcggc gggtctgatg gtggcggcgg     600
cctcgccgta tgtggcgtgg atgagcgtca ccgcggggca ggccgagctg accgccgccc     660
aggtccgggt tgctgcggcg gcctacgaga cggcgtatgg gctgacggtg ccccgccgg     720 tgatcgccga gaaccgtgct gaactgatga ttctgatagc gaccaacctc ttggggcaaa     780
acaccccggc gatcgcggtc aacgaggccg aatacggcga gatgtgggcc caagacgccg     840
ccgcgatgtt tggctacgcc gcggcgacgg cgacggcgac ggcgacgttg ctgccgttcg     900
aggaggcgcc ggagatgacc agcgcgggtg ggctcctcga gcaggccgcc gcggtcgagg     960
aggcctccga caccgccgcg gcgaaccagt tgatgaacaa tgtgccccag cgctgcaac    1020 agctggccca gcccacgcag ggcaccacgc cttcttccaa gctgggtggc ctgtggaaga    1080
cggtctcgcc gcatcggtcg ccgatcagca acatggtgtc gatggccaac aaccacatgt    1140
cgatgaccaa ctcgggtgtg tcgatgacca acaccttgag ctcgatgttg aagggctttg    1200
ctccggcggc ggccgcccag gccgtgcaaa ccgcggcgca aaacgggtc cgggcgatga    1260 gctcgctggg cagctcgctg ggttcttcgg gtctgggcgg tggggtggcc gccaacttgg    1320
```

```
gtcgggcggc tcggtcggt tcgttgtcgg tgccgcaggc ctgggccgcg gccaaccagg    1380
cagtcacccc ggcggcgcgg gcgctgccgc tgaccagcct gaccagcgcc gcggaaagag    1440
ggcccgggca gatgctgggc gggctgccgg tggggcagat gggcgccagg gccggtggtg    1500
ggctcagtgg tgtgctgcgt gttccgccgc gaccctatgt gatgccgcat tctccggcgg    1560
ccggctagga gaggggcgc agactgtcgt tatttgacca gtgatcggcg gtctcggtgt    1620
ttccgcggcc ggctatgaca acagtcaatg tgcatgacaa gttacaggta ttaggtccag    1680
gttcaacaag gagacaggca acatggcctc acgttttatg acggatccgc acgcgatgcg    1740
ggacatggcg ggccgttttg aggtgcacgc ccagacggtg gaggacgagg ctcgccggat    1800
gtgggcgtcc gcgcaaaaca tttccggtgc gggctggagt ggcatggccg aggcgacctc    1860
gctagacacc atggcccaga tgaatcaggc gtttcgcaac atcgtgaaca tgctgcacgg    1920
ggtgcgtgac gggctggttc gcgacgccaa caactacgag cagcaagagc aggcctccca    1980
gcagatcctc agcagctaac gtcagccgct gcagcacaat acttttacaa gcgaaggaga    2040
acaggttcga tgaccatcaa ctatcaattc ggggatgtcg acgctcacgg cgccatgatc    2100
cgcgctcagg ccgggttgct ggaggccgag catcaggcca tcattcgtga tgtgttgacc    2160
gcgagtgact tttggggcgg cgccggttcg gcggcctgcc aggggttcat acccagttg    2220 ggccgtaact tccaggtgat ctacgagcag gccaacgccc acgggcagaa ggtgcaggct    2280
gccggcaaca acatggcgca aaccgacagc gccgtcggct ccagctgggc ctgacaccag    2340
gccaaggcca gggacgtggt gtacgagtga agttcctcgc gtgatccttc gggtggcagt    2400
ctaagtggtc agtgctgggg tgttggtggt ttgctgcttg gcgggttctt cggtgctggt    2460
cagtgctgct cgggctcggg tgaggacctc gaggcccagg tagcgccgtc cttcgatcca    2520
ttcgtcgtgt tgttcggcga ggacggctcc gacgaggcgg atgatcgagg gcggtcggg    2580 gaagatgccc acgacgtcgg ttcggcgtcg tacctctcgg ttgaggcgtt cctgggggtt    2640
gttggaccag atttggcgcc agatctgctt ggggaaggcg gtgaacgcca gcaggtcggt    2700
gcgggcggtg tcgaggtgct cggccaccgc ggggagtttg tcggtcagag cgtcgagtac    2760
ccgatcatat tgggcaacaa ctgattcggc gtcgggctgg tcgtagatgg agtgcagcag    2820
ggtgcgcacc cacggccagg agggcttcgg ggtggctgcc atcagattgg ctgcgtagtg    2880
ggttctgcag cgctgccagg ccgctgcggg cagggtggcg ccgatcgcgg ccaccaggcc    2940
ggcgtgggcg tcgctggtga ccagcgcgac cccggacagg ccgcgggcga ccaggtcgcg    3000
gaagaacgcc agccagccgg ccccgtcctc ggcggaggtg acctggatgc ccaggatc     3058
```

<210> SEQ ID NO 14
<211> LENGTH: 391
<212> TYPE: PRT
<213> ORGANISM: Mycobacterium tuberculosis
<220> FEATURE:
<223> OTHER INFORMATION: MTB39 (TbH9FL)

<400> SEQUENCE: 14

```
Met Val Asp Phe Gly Ala Leu Pro Pro Glu Ile Asn Ser Ala Arg Met
 1               5                  10                  15

Tyr Ala Gly Pro Gly Ser Ala Ser Leu Val Ala Ala Ala Gln Met Trp
             20                  25                  30

Asp Ser Val Ala Ser Asp Leu Phe Ser Ala Ala Ser Ala Phe Gln Ser
         35                  40                  45

Val Val Trp Gly Leu Thr Val Gly Ser Trp Ile Gly Ser Ser Ala Gly
     50                  55                  60
```

```
Leu Met Val Ala Ala Ser Pro Tyr Val Trp Met Ser Val Thr
 65                  70                  75                  80

Ala Gly Gln Ala Glu Leu Thr Ala Ala Gln Val Arg Val Ala Ala
             85                  90                  95

Ala Tyr Glu Thr Ala Tyr Gly Leu Thr Val Pro Pro Val Ile Ala
            100                 105                 110

Glu Asn Arg Ala Glu Leu Met Ile Leu Ile Ala Thr Asn Leu Leu Gly
            115                 120                 125

Gln Asn Thr Pro Ala Ile Ala Val Asn Glu Ala Glu Tyr Gly Glu Met
            130                 135                 140

Trp Ala Gln Asp Ala Ala Ala Met Phe Gly Tyr Ala Ala Ala Thr Ala
145                 150                 155                 160

Thr Ala Thr Ala Thr Leu Leu Pro Phe Glu Glu Ala Pro Glu Met Thr
                    165                 170                 175

Ser Ala Gly Gly Leu Leu Glu Gln Ala Ala Ala Val Glu Glu Ala Ser
                    180                 185                 190

Asp Thr Ala Ala Ala Asn Gln Leu Met Asn Asn Val Pro Gln Ala Leu
                    195                 200                 205

Gln Gln Leu Ala Gln Pro Thr Gln Gly Thr Thr Pro Ser Ser Lys Leu
210                 215                 220

Gly Gly Leu Trp Lys Thr Val Ser Pro His Arg Ser Pro Ile Ser Asn
225                 230                 235                 240

Met Val Ser Met Ala Asn Asn His Met Ser Met Thr Asn Ser Gly Val
                    245                 250                 255

Ser Met Thr Asn Thr Leu Ser Ser Met Leu Lys Gly Phe Ala Pro Ala
                    260                 265                 270

Ala Ala Ala Gln Ala Val Gln Thr Ala Ala Gln Asn Gly Val Arg Ala
                    275                 280                 285

Met Ser Ser Leu Gly Ser Ser Leu Gly Ser Ser Gly Leu Gly Gly Gly
                    290                 295                 300

Val Ala Ala Asn Leu Gly Arg Ala Ala Ser Val Gly Ser Leu Ser Val
305                 310                 315                 320

Pro Gln Ala Trp Ala Ala Ala Asn Gln Ala Val Thr Pro Ala Ala Arg
                    325                 330                 335

Ala Leu Pro Leu Thr Ser Leu Thr Ser Ala Ala Glu Arg Gly Pro Gly
                    340                 345                 350

Gln Met Leu Gly Gly Leu Pro Val Gly Gln Met Gly Ala Arg Ala Gly
                    355                 360                 365

Gly Gly Leu Ser Gly Val Leu Arg Val Pro Pro Arg Pro Tyr Val Met
                    370                 375                 380

Pro His Ser Pro Ala Ala Gly
385                 390

<210> SEQ ID NO 15
<211> LENGTH: 2287
<212> TYPE: DNA
<213> ORGANISM: Artificial Sequence
<220> FEATURE:
<223> OTHER INFORMATION: Description of Artificial Sequence:tri-fusion
      protein MTB72F (Ra12-TbH9-Ra35 or MTB32-MTB39
      fusion)
<220> FEATURE:
<221> NAME/KEY: CDS
<222> LOCATION: (42)..(2231)
<223> OTHER INFORMATION: MTB72F
<220> FEATURE:
<221> NAME/KEY: modified_base
<222> LOCATION: (30)
<223> OTHER INFORMATION: n = g, a, c or t
```

-continued

```
<220> FEATURE:
<221> NAME/KEY: modified_base
<222> LOCATION: (33)
<223> OTHER INFORMATION: n = g, a, c or t
<220> FEATURE:
<221> NAME/KEY: modified_base
<222> LOCATION: (2270)
<223> OTHER INFORMATION: n = g, a, c or t

<400> SEQUENCE: 15
tctagaaata attttgttta ctttaagaan ganatataca t atg cat cac cat cac          56
                                              Met His His His His
                                              1               5 cat cac acg gcc gcg tcc gat aac ttc cag ctg tcc cag ggt ggg cag           104
His His Thr Ala Ala Ser Asp Asn Phe Gln Leu Ser Gln Gly Gly Gln
             10                  15                  20 gga ttc gcc att ccg atc ggg cag gcg atg gcg atc gcg ggc cag atc          152
Gly Phe Ala Ile Pro Ile Gly Gln Ala Met Ala Ile Ala Gly Gln Ile
             25                  30                  35 cga tcg ggt ggg ggg tca ccc acc gtt cat atc ggg cct acc gcc ttc          200
Arg Ser Gly Gly Gly Ser Pro Thr Val His Ile Gly Pro Thr Ala Phe
        40                  45                  50 ctc ggc ttg ggt gtt gtc gac aac aac ggc aac ggc gca cga gtc caa          248
Leu Gly Leu Gly Val Val Asp Asn Asn Gly Asn Gly Ala Arg Val Gln
55                  60                  65 cgc gtg gtc ggg agc gct ccg gcg gca agt ctc ggc atc tcc acc ggc          296
Arg Val Val Gly Ser Ala Pro Ala Ala Ser Leu Gly Ile Ser Thr Gly
70                  75                  80                  85 gac gtg atc acc gcg gtc gac ggc gct ccg atc aac tcg gcc acc gcg          344
Asp Val Ile Thr Ala Val Asp Gly Ala Pro Ile Asn Ser Ala Thr Ala
             90                  95                 100 atg gcg gac gcg ctt aac ggg cat cat ccc ggt gac gtc atc tcg gtg          392
Met Ala Asp Ala Leu Asn Gly His His Pro Gly Asp Val Ile Ser Val
            105                 110                 115 acc tgg caa acc aag tcg ggc ggc acg cgt aca ggg aac gtg aca ttg          440
Thr Trp Gln Thr Lys Ser Gly Gly Thr Arg Thr Gly Asn Val Thr Leu
        120                 125                 130 gcc gag gga ccc ccg gcc gaa ttc atg gtg gat ttc ggg gcg tta cca          488
Ala Glu Gly Pro Pro Ala Glu Phe Met Val Asp Phe Gly Ala Leu Pro
135                 140                 145 ccg gag atc aac tcc gcg agg atg tac gcc ggc ccg ggt tcg gcc tcg          536
Pro Glu Ile Asn Ser Ala Arg Met Tyr Ala Gly Pro Gly Ser Ala Ser
150                 155                 160                 165 ctg gtg gcc gcg gct cag atg tgg gac agc gtg gcg agt gac ctg ttt          584
Leu Val Ala Ala Ala Gln Met Trp Asp Ser Val Ala Ser Asp Leu Phe
            170                 175                 180 tcg gcc gcg tcg gcg ttt cag tcg gtg gtc tgg ggt ctg acg gtg ggg          632
Ser Ala Ala Ser Ala Phe Gln Ser Val Val Trp Gly Leu Thr Val Gly
            185                 190                 195 tcg tgg ata ggt tcg tcg gcg ggt ctg atg gtg gcg gcg tcg ccg              680
Ser Trp Ile Gly Ser Ser Ala Gly Leu Met Val Ala Ala Ser Pro
        200                 205                 210 tat gtg gcg tgg atg agc gtc acc gcg ggg cag gcc gag ctg acc gcc          728
Tyr Val Ala Trp Met Ser Val Thr Ala Gly Gln Ala Glu Leu Thr Ala
215                 220                 225 gcc cag gtc cgg gtt gct gcg gcg gcc tac gag acg gcg tat ggg ctg          776
Ala Gln Val Arg Val Ala Ala Ala Ala Tyr Glu Thr Ala Tyr Gly Leu
230                 235                 240                 245 acg gtg ccc ccg ccg gtg atc gcc gag aac cgt gct gaa ctg atg att          824
Thr Val Pro Pro Pro Val Ile Ala Glu Asn Arg Ala Glu Leu Met Ile
            250                 255                 260 ctg ata gcg acc aac ctc ttg ggg caa aac acc ccg gcg atc gcg gtc          872
```

```
                                                          -continued

Leu Ile Ala Thr Asn Leu Leu Gly Gln Asn Thr Pro Ala Ile Ala Val
            265                 270                 275 aac gag gcc gaa tac ggc gag atg tgg gcc caa gac gcc gcc gcg atg    920
Asn Glu Ala Glu Tyr Gly Glu Met Trp Ala Gln Asp Ala Ala Ala Met
                280                 285                 290 ttt ggc tac gcc gcg gcg acg gcg acg gcg acg ttg ctg ccg            968
Phe Gly Tyr Ala Ala Ala Thr Ala Thr Ala Thr Leu Leu Pro
    295                 300                 305 ttc gag gag gcg ccg gag atg acc agc gcg ggt ggg ctc ctc gag cag   1016
Phe Glu Glu Ala Pro Glu Met Thr Ser Ala Gly Gly Leu Leu Glu Gln
310                 315                 320                 325 gcc gcc gcg gtc gag gag gcc tcc gac acc gcg gcg aac cag ttg       1064
Ala Ala Ala Val Glu Glu Ala Ser Asp Thr Ala Ala Asn Gln Leu
                330                 335                 340 atg aac aat gtg ccc cag gcg ctg caa cag ctg gcc cag ccc acg cag   1112
Met Asn Asn Val Pro Gln Ala Leu Gln Gln Leu Ala Gln Pro Thr Gln
                345                 350                 355 ggc acc acg cct tct tcc aag ctg ggt ggc ctg tgg aag acg gtc tcg   1160
Gly Thr Thr Pro Ser Ser Lys Leu Gly Gly Leu Trp Lys Thr Val Ser
            360                 365                 370 ccg cat cgg tcg ccg atc agc aac atg gtg tcg atg gcc aac aac cac   1208
Pro His Arg Ser Pro Ile Ser Asn Met Val Ser Met Ala Asn Asn His
    375                 380                 385 atg tcg atg acc aac tcg ggt gtg tcg atg acc aac acc ttg agc tcg   1256
Met Ser Met Thr Asn Ser Gly Val Ser Met Thr Asn Thr Leu Ser Ser
390                 395                 400                 405 atg ttg aag ggc ttt gct ccg gcg gcg gcc gcc cag gcc gtg caa acc   1304
Met Leu Lys Gly Phe Ala Pro Ala Ala Ala Ala Gln Ala Val Gln Thr
                410                 415                 420 gcg gcg caa aac ggg gtc cgg gcg atg agc tcg ctg ggc agc tcg ctg   1352
Ala Ala Gln Asn Gly Val Arg Ala Met Ser Ser Leu Gly Ser Ser Leu
            425                 430                 435 ggt tct tcg ggt ctg ggc ggt ggg gtg gcc gcc aac ttg ggt cgg gcg   1400
Gly Ser Ser Gly Leu Gly Gly Gly Val Ala Ala Asn Leu Gly Arg Ala
        440                 445                 450 gcc tcg gtc ggt tcg ttg tcg gtg ccg cag gcc tgg gcc gcg gcc aac   1448
Ala Ser Val Gly Ser Leu Ser Val Pro Gln Ala Trp Ala Ala Ala Asn
455                 460                 465 cag gca gtc acc ccg gcg gcg cgg gcg ctg ccg ctg acc agc ctg acc   1496
Gln Ala Val Thr Pro Ala Ala Arg Ala Leu Pro Leu Thr Ser Leu Thr
470                 475                 480                 485 agc gcc gcg gaa aga ggg ccc ggg cag atg ctg ggc ggg ctg ccg gtg   1544
Ser Ala Ala Glu Arg Gly Pro Gly Gln Met Leu Gly Gly Leu Pro Val
                490                 495                 500 ggg cag atg ggc gcc agg gcc ggt ggt ggg ctc agt ggt gtg ctg cgt   1592
Gly Gln Met Gly Ala Arg Ala Gly Gly Gly Leu Ser Gly Val Leu Arg
            505                 510                 515 gtt ccg ccg cga ccc tat gtg atg ccg cat tct ccg gca gcc ggc gat   1640
Val Pro Pro Arg Pro Tyr Val Met Pro His Ser Pro Ala Ala Gly Asp
        520                 525                 530 atc gcc ccg ccg gcc ttg tcg cag gac cgg ttc gcc gac ttc ccc gcg   1688
Ile Ala Pro Pro Ala Leu Ser Gln Asp Arg Phe Ala Asp Phe Pro Ala
535                 540                 545 ctg ccc ctc gac ccg tcc gcg atg gtc gcc caa gtg ggg cca cag gtg   1736
Leu Pro Leu Asp Pro Ser Ala Met Val Ala Gln Val Gly Pro Gln Val
550                 555                 560                 565 gtc aac atc aac acc aaa ctg ggc tac aac aac gcc gtg ggc gcc ggg   1784
Val Asn Ile Asn Thr Lys Leu Gly Tyr Asn Asn Ala Val Gly Ala Gly
                570                 575                 580 acc ggc atc gtc atc gat ccc aac ggt gtc gtg ctg acc aac aac cac   1832
Thr Gly Ile Val Ile Asp Pro Asn Gly Val Val Leu Thr Asn Asn His
```

```
Thr Gly Ile Val Ile Asp Pro Asn Gly Val Val Leu Thr Asn Asn His
            585                 590                 595 gtg atc gcg ggc gcc acc gac atc aat gcg ttc agc gtc ggc tcc ggc      1880
Val Ile Ala Gly Ala Thr Asp Ile Asn Ala Phe Ser Val Gly Ser Gly
        600                 605                 610 caa acc tac ggc gtc gat gtg gtc ggg tat gac cgc acc cag gat gtc      1928
Gln Thr Tyr Gly Val Asp Val Val Gly Tyr Asp Arg Thr Gln Asp Val
        615                 620                 625 gcg gtg ctg cag ctg cgc ggt gcc ggt ggc ctg ccg tcg gcg gcg atc      1976
Ala Val Leu Gln Leu Arg Gly Ala Gly Gly Leu Pro Ser Ala Ala Ile
630             635                 640                 645 ggt ggc ggc gtc gcg gtt ggt gag ccc gtc gtc gcg atg ggc aac agc      2024
Gly Gly Gly Val Ala Val Gly Glu Pro Val Val Ala Met Gly Asn Ser
        650                 655                 660 ggt ggg cag ggc gga acg ccc cgt gcg gtg cct ggc agg gtg gtc gcg      2072
Gly Gly Gln Gly Gly Thr Pro Arg Ala Val Pro Gly Arg Val Val Ala
        665                 670                 675 ctc ggc caa acc gtg cag gcg tcg gat tcg ctg acc ggt gcc gaa gag      2120
Leu Gly Gln Thr Val Gln Ala Ser Asp Ser Leu Thr Gly Ala Glu Glu
        680                 685                 690 aca ttg aac ggg ttg atc cag ttc gat gcc gcg atc cag ccc ggt gat      2168
Thr Leu Asn Gly Leu Ile Gln Phe Asp Ala Ala Ile Gln Pro Gly Asp
695                 700                 705 tcg ggc ggg ccc gtc gtc aac ggc cta gga cag gtg gtc ggt atg aac      2216
Ser Gly Gly Pro Val Val Asn Gly Leu Gly Gln Val Val Gly Met Asn
710                 715                 720                 725 acg gcc gcg tcc tag gatatccatc acactggcgg ccgctcgagc agatccggnt      2271
Thr Ala Ala Ser gtaacaaagc ccgaaa                                                    2287

<210> SEQ ID NO 16
<211> LENGTH: 729
<212> TYPE: PRT
<213> ORGANISM: Artificial Sequence
<220> FEATURE:
<223> OTHER INFORMATION: Description of Artificial Sequence:tri-fusion
      protein MTB72F (Ra12-TbH9-Ra35 or MTB32-MTB39
      fusion)

<400> SEQUENCE: 16

Met His His His His His Thr Ala Ala Ser Asp Asn Phe Gln Leu
1               5                   10                  15

Ser Gln Gly Gly Gln Gly Phe Ala Ile Pro Ile Gly Gln Ala Met Ala
                20                  25                  30

Ile Ala Gly Gln Ile Arg Ser Gly Gly Gly Ser Pro Thr Val His Ile
            35                  40                  45

Gly Pro Thr Ala Phe Leu Gly Leu Gly Val Val Asp Asn Asn Gly Asn
        50                  55                  60

Gly Ala Arg Val Gln Arg Val Val Gly Ser Ala Pro Ala Ala Ser Leu
65                  70                  75                  80

Gly Ile Ser Thr Gly Asp Val Ile Thr Ala Val Asp Gly Ala Pro Ile
                85                  90                  95

Asn Ser Ala Thr Ala Met Ala Asp Ala Leu Asn Gly His His Pro Gly
                100                 105                 110

Asp Val Ile Ser Val Thr Trp Gln Thr Lys Ser Gly Gly Thr Arg Thr
            115                 120                 125

Gly Asn Val Thr Leu Ala Glu Gly Pro Pro Ala Glu Phe Met Val Asp
        130                 135                 140

Phe Gly Ala Leu Pro Pro Glu Ile Asn Ser Ala Arg Met Tyr Ala Gly
```

```
                  145                 150                 155                 160
Pro Gly Ser Ala Ser Leu Val Ala Ala Ala Gln Met Trp Asp Ser Val
                165                 170                 175

Ala Ser Asp Leu Phe Ser Ala Ser Ala Phe Gln Ser Val Val Trp
            180                 185                 190

Gly Leu Thr Val Gly Ser Trp Ile Gly Ser Ser Ala Gly Leu Met Val
            195                 200                 205

Ala Ala Ala Ser Pro Tyr Val Ala Trp Met Ser Val Thr Ala Gly Gln
            210                 215                 220

Ala Glu Leu Thr Ala Ala Gln Val Arg Val Ala Ala Ala Ala Tyr Glu
225                 230                 235                 240

Thr Ala Tyr Gly Leu Thr Val Pro Pro Val Ile Ala Glu Asn Arg
                245                 250                 255

Ala Glu Leu Met Ile Leu Ile Ala Thr Asn Leu Leu Gly Gln Asn Thr
                260                 265                 270

Pro Ala Ile Ala Val Asn Glu Ala Glu Tyr Gly Glu Met Trp Ala Gln
                275                 280                 285

Asp Ala Ala Ala Met Phe Gly Tyr Ala Ala Ala Thr Ala Thr Ala Thr
290                 295                 300

Ala Thr Leu Leu Pro Phe Glu Ala Pro Glu Met Thr Ser Ala Gly
305                 310                 315                 320

Gly Leu Leu Glu Gln Ala Ala Val Glu Glu Ala Ser Asp Thr Ala
                325                 330                 335

Ala Ala Asn Gln Leu Met Asn Asn Val Pro Gln Ala Leu Gln Gln Leu
                340                 345                 350

Ala Gln Pro Thr Gln Gly Thr Thr Pro Ser Ser Lys Leu Gly Gly Leu
                355                 360                 365

Trp Lys Thr Val Ser Pro His Arg Ser Pro Ile Ser Asn Met Val Ser
                370                 375                 380

Met Ala Asn Asn His Met Ser Met Thr Asn Ser Gly Val Ser Met Thr
385                 390                 395                 400

Asn Thr Leu Ser Ser Met Leu Lys Gly Phe Ala Pro Ala Ala Ala
                405                 410                 415

Gln Ala Val Gln Thr Ala Ala Gln Asn Gly Val Arg Ala Met Ser Ser
                420                 425                 430

Leu Gly Ser Ser Leu Gly Ser Ser Gly Leu Gly Gly Val Ala Ala
                435                 440                 445

Asn Leu Gly Arg Ala Ala Ser Val Gly Ser Leu Ser Val Pro Gln Ala
                450                 455                 460

Trp Ala Ala Ala Asn Gln Ala Val Thr Pro Ala Ala Arg Ala Leu Pro
465                 470                 475                 480

Leu Thr Ser Leu Thr Ser Ala Ala Glu Arg Gly Pro Gly Gln Met Leu
                485                 490                 495

Gly Gly Leu Pro Val Gly Gln Met Gly Ala Arg Ala Gly Gly Leu
                500                 505                 510

Ser Gly Val Leu Arg Val Pro Pro Arg Pro Tyr Val Met Pro His Ser
                515                 520                 525

Pro Ala Ala Gly Asp Ile Ala Pro Pro Ala Leu Ser Gln Asp Arg Phe
                530                 535                 540

Ala Asp Phe Pro Ala Leu Pro Leu Asp Pro Ser Ala Met Val Ala Gln
545                 550                 555                 560

Val Gly Pro Gln Val Val Asn Ile Asn Thr Lys Leu Gly Tyr Asn Asn
                565                 570                 575
```

```
Ala Val Gly Ala Gly Thr Gly Ile Val Ile Asp Pro Asn Gly Val Val
            580                 585                 590
Leu Thr Asn Asn His Val Ile Ala Gly Ala Thr Asp Ile Asn Ala Phe
        595                 600                 605
Ser Val Gly Ser Gly Gln Thr Tyr Gly Val Asp Val Val Gly Tyr Asp
    610                 615                 620
Arg Thr Gln Asp Val Ala Val Leu Gln Leu Arg Gly Ala Gly Leu
625                 630                 635                 640
Pro Ser Ala Ala Ile Gly Gly Val Ala Val Gly Glu Pro Val Val
                645                 650                 655
Ala Met Gly Asn Ser Gly Gly Gln Gly Gly Thr Pro Arg Ala Val Pro
            660                 665                 670
Gly Arg Val Val Ala Leu Gly Gln Thr Val Gln Ala Ser Asp Ser Leu
        675                 680                 685
Thr Gly Ala Glu Glu Thr Leu Asn Gly Leu Ile Gln Phe Asp Ala Ala
    690                 695                 700
Ile Gln Pro Gly Asp Ser Gly Gly Pro Val Val Asn Gly Leu Gly Gln
705                 710                 715                 720
Val Val Gly Met Asn Thr Ala Ala Ser
                725

<210> SEQ ID NO 17
<211> LENGTH: 2190
<212> TYPE: DNA
<213> ORGANISM: Artificial Sequence
<220> FEATURE:
<223> OTHER INFORMATION: Description of Artificial Sequence:MTB72FMutSA
      (Ra12-TbHp-Ra35MutSA) cDNA

<400> SEQUENCE: 17
atgcatcacc atcaccatca cacggccgcg tccgataact tccagctgtc ccagggtggg      60
cagggattcg ccattccgat cgggcaggcg atggcgatcg cgggccagat ccgatcgggt     120 gggggtcac ccaccgttca tatcgggcct accgccttcc tcggcttggg tgttgtcgac     180
aacaacggca acggcgcacg agtccaacgc gtggtcggga cgctccggc ggcaagtctc     240 ggcatctcca ccggcgacgt gatcaccgcg gtcgacggcg ctccgatcaa ctcggccacc     300
gcgatggcgg acgcgcttaa cgggcatcat cccggtgacg tcatctcggt gacctggcaa     360
accaagtcgg gcggcacgcg tacagggaac gtgacattgg ccgagggacc ccggccgaa      420 ttcatggtgg atttcggggc gttaccaccg gagatcaact ccgcgaggat gtacgccggc     480
ccgggttcgg cctcgctggt ggccgcggct cagatgtggg acagcgtggc gagtgacctg     540
ttttcggccg cgtcggcgtt tcagtcggtg gtctggggtc tgacggtggg gtcgtggata     600
ggttcgtcgg cgggtctgat ggtggcggcg gcctcgccgt atgtggcgtg gatgagcgtc     660 accgcgggc aggccgagct gaccgccgcc caggtccggg ttgctgcggc ggcctacgag     720
acggcgtatg gctgacggt gccccgccg gtgatcgccg agaaccgtgc tgaactgatg     780
attctgatag cgaccaacct cttggggcaa acaccccgg cgatcgcggt caacgaggcc     840
gaatacggcg agatgtgggc ccaagacgcc gccgcgatgt ttggctacgc cgcggcgacg     900
gcgacggcga cggcgacgtt gctgccgttc gaggaggcgc cggagatgac cagcgcgggt     960
gggctcctcg agcaggccgc cgcggtcgag gaggcctccg acaccgccgc ggcgaaccag    1020
ttgatgaaca atgtgcccca ggcgctgcaa cagctggccc agcccacgca gggcaccacg    1080
ccttcttcca gctgggtgg cctgtggaag acggtctcgc cgcatcggtc gccgatcagc    1140
aacatggtgt cgatggccaa caaccacatg tcgatgacca actcgggtgt gtcgatgacc    1200
```

```
aacaccttga gctcgatgtt gaagggcttt gctccggcgg cggccgccca ggccgtgcaa      1260
accgcggcgc aaaacggggt ccgggcgatg agctcgctgg gcagctcgct gggttcttcg      1320
ggtctgggcg gtggggtggc cgccaacttg gtcggcgg cctcggtcgg ttcgttgtcg       1380
gtgccgcagg cctgggccgc ggccaaccag gcagtcaccc cggcggcgcg ggcgctgccg      1440
ctgaccagcc tgaccagcgc cgcggaaaga gggcccgggc agatgctggg cgggctgccg      1500
gtggggcaga tgggcgccag ggccggtggt gggctcagtg gtgtgctgcg tgttccgccg      1560 cgacccatg tgatgccgca ttctccggca gccggcgata tcgccccgcc ggccttgtcg      1620
caggaccggt tcgccgactt ccccgcgctg ccctcgacc cgtccgcgat ggtcgcccaa      1680
gtggggccac aggtggtcaa catcaacacc aaactgggct acaacaacgc cgtgggcgcc      1740
gggaccggca tcgtcatcga tcccaacggt gtcgtgctga ccaacaacca cgtgatcgcg      1800
ggcgccaccg acatcaatgc gttcagcgtc ggctccggcc aaacctacgg cgtcgatgtg      1860
gtcgggtatg accgcaccca ggatgtcgcg gtgctgcagc tgcgcggtgc cggtggcctg      1920
ccgtcggcgg cgatcggtgg cggcgtcgcg gttggtgagc ccgtcgtcgc gatgggcaac      1980
agcggtgggc agggcggaac gccccgtgcg gtgcctggca gggtggtcgc gctcggccaa      2040
accgtgcagg cgtcggattc gctgaccggt gccgaagaga cattgaacgg gttgatccag      2100
ttcgatgccg cgatccagcc cggtgatgcg ggcgggcccg tcgtcaacgg cctaggacag      2160
gtggtcggta tgaacacggc cgcgtcctag                                      2190
```

<210> SEQ ID NO 18
<211> LENGTH: 729
<212> TYPE: PRT
<213> ORGANISM: Artificial Sequence
<220> FEATURE:
<223> OTHER INFORMATION: Description of Artificial Sequence:MTB72FMutSA
      (Ra12-TbHp-Ra35MutSA)

<400> SEQUENCE: 18

```
Met His His His His His His Thr Ala Ala Ser

-continued

```
                180                 185                 190
Gly Leu Thr Val Gly Ser Trp Ile Gly Ser Ser Ala Gly Leu Met Val
            195                 200                 205
Ala Ala Ala Ser Pro Tyr Val Ala Trp Met Ser Val Thr Ala Gly Gln
        210                 215                 220
Ala Glu Leu Thr Ala Ala Gln Val Arg Val Ala Ala Ala Tyr Glu
225                 230                 235                 240
Thr Ala Tyr Gly Leu Thr Val Pro Pro Val Ile Ala Glu Asn Arg
                245                 250                 255
Ala Glu Leu Met Ile Leu Ile Ala Thr Asn Leu Leu Gly Gln Asn Thr
            260                 265                 270
Pro Ala Ile Ala Val Asn Glu Ala Glu Tyr Gly Glu Met Trp Ala Gln
        275                 280                 285
Asp Ala Ala Met Phe Gly Tyr Ala Ala Ala Thr Ala Thr Ala Thr
    290                 295                 300
Ala Thr Leu Leu Pro Phe Glu Glu Ala Pro Glu Met Thr Ser Ala Gly
305                 310                 315                 320
Gly Leu Leu Glu Gln Ala Ala Ala Val Glu Glu Ala Ser Asp Thr Ala
                325                 330                 335
Ala Ala Asn Gln Leu Met Asn Asn Val Pro Gln Ala Leu Gln Gln Leu
            340                 345                 350
Ala Gln Pro Thr Gln Gly Thr Thr Pro Ser Ser Lys Leu Gly Gly Leu
        355                 360                 365
Trp Lys Thr Val Ser Pro His Arg Ser Pro Ile Ser Asn Met Val Ser
    370                 375                 380
Met Ala Asn Asn His Met Ser Met Thr Asn Ser Gly Val Ser Met Thr
385                 390                 395                 400
Asn Thr Leu Ser Ser Met Leu Lys Gly Phe Ala Pro Ala Ala Ala
                405                 410                 415
Gln Ala Val Gln Thr Ala Ala Gln Asn Gly Val Arg Ala Met Ser Ser
            420                 425                 430
Leu Gly Ser Ser Leu Gly Ser Ser Gly Leu Gly Gly Val Ala Ala
        435                 440                 445
Asn Leu Gly Arg Ala Ala Ser Val Gly Ser Leu Ser Val Pro Gln Ala
    450                 455                 460
Trp Ala Ala Ala Asn Gln Ala Val Thr Pro Ala Ala Arg Ala Leu Pro
465                 470                 475                 480
Leu Thr Ser Leu Thr Ser Ala Ala Glu Arg Gly Pro Gly Gln Met Leu
                485                 490                 495
Gly Gly Leu Pro Val Gly Gln Met Gly Ala Arg Ala Gly Gly Leu
            500                 505                 510
Ser Gly Val Leu Arg Val Pro Pro Arg Pro Tyr Val Met Pro His Ser
        515                 520                 525
Pro Ala Ala Gly Asp Ile Ala Pro Pro Ala Leu Ser Gln Asp Arg Phe
    530                 535                 540
Ala Asp Phe Pro Ala Leu Pro Leu Asp Pro Ser Ala Met Val Ala Gln
545                 550                 555                 560
Val Gly Pro Gln Val Val Asn Ile Asn Thr Lys Leu Gly Tyr Asn Asn
                565                 570                 575
Ala Val Gly Ala Gly Thr Gly Ile Val Ile Asp Pro Asn Gly Val Val
            580                 585                 590
Leu Thr Asn Asn His Val Ile Ala Gly Ala Thr Asp Ile Asn Ala Phe
        595                 600                 605
```

```
Ser Val Gly Ser Gly Gln Thr Tyr Gly Val Asp Val Gly Tyr Asp
    610                 615                 620

Arg Thr Gln Asp Val Ala Val Leu Gln Leu Arg Gly Ala Gly Leu
625                 630                 635                 640

Pro Ser Ala Ala Ile Gly Gly Val Ala Val Gly Glu Pro Val Val
                645                 650                 655

Ala Met Gly Asn Ser Gly Gly Gln Gly Gly Thr Pro Arg Ala Val Pro
            660                 665                 670

Gly Arg Val Val Ala Leu Gly Gln Thr Val Gln Ala Ser Asp Ser Leu
                675                 680                 685

Thr Gly Ala Glu Glu Thr Leu Asn Gly Leu Ile Gln Phe Asp Ala Ala
            690                 695                 700

Ile Gln Pro Gly Asp Ala Gly Gly Pro Val Val Asn Gly Leu Gly Gln
705                 710                 715                 720

Val Val Gly Met Asn Thr Ala Ala Ser
                725
```

```
<210> SEQ ID NO 19
<211> LENGTH: 1797
<212> TYPE: DNA
<213> ORGANISM: Artificial Sequence
<220> FEATURE:
<223> OTHER INFORMATION: Description of Artificial Sequence:bi-fusion
      protein TbH9-Ra35 (designated MTB59F)
<220> FEATURE:
<221> NAME/KEY: CDS
<222> LOCATION: (1)..(1791)
<223> OTHER INFORMATION: MTB59F

<400> SEQUENCE: 19 cat atg cat cac cat cac cat cac atg gtg gat ttc ggg gcg tta cca        48
His Met His His His His His His Met Val Asp Phe Gly Ala Leu Pro
 1               5                  10                  15 ccg gag atc aac tcc gcg agg atg tac gcc ggc ccg ggt tcg gcc tcg        96
Pro Glu Ile Asn Ser Ala Arg Met Tyr Ala Gly Pro Gly Ser Ala Ser
                20                  25                  30 ctg gtg gcc gcg gct cag atg tgg gac agc gtg gcg agt gac ctg ttt       144
Leu Val Ala Ala Ala Gln Met Trp Asp Ser Val Ala Ser Asp Leu Phe
            35                  40                  45 tcg gcc gcg tcg gcg ttt cag tcg gtg gtc tgg ggt ctg acg gtg ggg       192
Ser Ala Ala Ser Ala Phe Gln Ser Val Val Trp Gly Leu Thr Val Gly
        50                  55                  60 tcg tgg ata ggt tcg tcg gcg ggt ctg atg gtg gcg gcg gcc tcg ccg       240
Ser Trp Ile Gly Ser Ser Ala Gly Leu Met Val Ala Ala Ala Ser Pro
 65                  70                  75                  80 tat gtg gcg tgg atg agc gtc acc gcg ggg cag gcc gag ctg acc gcc       288
Tyr Val Ala Trp Met Ser Val Thr Ala Gly Gln Ala Glu Leu Thr Ala
                85                  90                  95 gcc cag gtc cgg gtt gct gcg gcg gcc tac gag acg gcg tat ggg ctg       336
Ala Gln Val Arg Val Ala Ala Ala Ala Tyr Glu Thr Ala Tyr Gly Leu
                100                 105                 110 acg gtg ccc ccg ccg gtg atc gcc gag aac cgt gct gaa ctg atg att       384
Thr Val Pro Pro Pro Val Ile Ala Glu Asn Arg Ala Glu Leu Met Ile
            115                 120                 125 ctg ata gcg acc aac ctc ttg ggg caa aac acc ccg gcg atc gcg gtc       432
Leu Ile Ala Thr Asn Leu Leu Gly Gln Asn Thr Pro Ala Ile Ala Val
        130                 135                 140 aac gag gcc gaa tac ggc gag atg tgg gcc caa gac gcc gcc gcg atg       480
Asn Glu Ala Glu Tyr Gly Glu Met Trp Ala Gln Asp Ala Ala Ala Met
145                 150                 155                 160 ttt ggc tac gcc gcg gcg acg gcg acg gcg acg gcg acg ttg ctg ccg       528
```

```
                Phe Gly Tyr Ala Ala Ala Thr Ala Thr Ala Thr Leu Leu Pro
                                165                 170                 175 ttc gag gag gcg ccg gag atg acc agc gcg ggt ggg ctc ctc gag cag          576
Phe Glu Glu Ala Pro Glu Met Thr Ser Ala Gly Gly Leu Leu Glu Gln
                180                 185                 190 gcc gcc gcg gtc gag gag gcc tcc gac acc gcg gcg aac cag ttg              624
Ala Ala Ala Val Glu Glu Ala Ser Asp Thr Ala Ala Asn Gln Leu
            195                 200                 205 atg aac aat gtg ccc cag gcg ctg caa cag ctg gcc cag ccc acg cag          672
Met Asn Asn Val Pro Gln Ala Leu Gln Gln Leu Ala Gln Pro Thr Gln
    210                 215                 220 ggc acc acg cct tct tcc aag ctg ggt ggc ctg tgg aag acg gtc tcg          720
Gly Thr Thr Pro Ser Ser Lys Leu Gly Gly Leu Trp Lys Thr Val Ser
225                 230                 235                 240 ccg cat cgg tcg ccg atc agc aac atg gtg tcg atg gcc aac aac cac          768
Pro His Arg Ser Pro Ile Ser Asn Met Val Ser Met Ala Asn Asn His
                245                 250                 255 atg tcg atg acc aac tcg ggt gtg tcg atg acc aac acc ttg agc tcg          816
Met Ser Met Thr Asn Ser Gly Val Ser Met Thr Asn Thr Leu Ser Ser
                260                 265                 270 atg ttg aag ggc ttt gct ccg gcg gcg gcc gcc cag gcc gtg caa acc          864
Met Leu Lys Gly Phe Ala Pro Ala Ala Ala Ala Gln Ala Val Gln Thr
            275                 280                 285 gcg gcg caa aac ggg gtc cgg gcg atg agc tcg ctg ggc agc tcg ctg          912
Ala Ala Gln Asn Gly Val Arg Ala Met Ser Ser Leu Gly Ser Ser Leu
        290                 295                 300 ggt tct tcg ggt ctg ggc ggt ggg gtg gcc gcc aac ttg ggt cgg gcg          960
Gly Ser Ser Gly Leu Gly Gly Gly Val Ala Ala Asn Leu Gly Arg Ala
305                 310                 315                 320 gcc tcg gtc ggt tcg ttg tcg gtg ccg cag gcc tgg gcc gcg gcc aac         1008
Ala Ser Val Gly Ser Leu Ser Val Pro Gln Ala Trp Ala Ala Ala Asn
                325                 330                 335 cag gca gtc acc ccg gcg gcg cgg gcg ctg ccg ctg acc agc ctg acc         1056
Gln Ala Val Thr Pro Ala Ala Arg Ala Leu Pro Leu Thr Ser Leu Thr
                340                 345                 350 agc gcc gcg gaa aga ggg ccc ggg cag atg ctg ggc ggg ctg ccg gtg         1104
Ser Ala Ala Glu Arg Gly Pro Gly Gln Met Leu Gly Gly Leu Pro Val
            355                 360                 365 ggg cag atg ggc gcc agg gcc ggt ggt ggg ctc agt ggt gtg ctg cgt         1152
Gly Gln Met Gly Ala Arg Ala Gly Gly Gly Leu Ser Gly Val Leu Arg
        370                 375                 380 gtt ccg ccg cga ccc tat gtg atg ccg cat tct ccg gca gcc ggc gat         1200
Val Pro Pro Arg Pro Tyr Val Met Pro His Ser Pro Ala Ala Gly Asp
385                 390                 395                 400 atc gcc ccg ccg gcc ttg tcg cag gac cgg ttc gcc gac ttc ccc gcg         1248
Ile Ala Pro Pro Ala Leu Ser Gln Asp Arg Phe Ala Asp Phe Pro Ala
                405                 410                 415 ctg ccc ctc gac ccg tcc gcg atg gtc gcc caa gtg ggg cca cag gtg         1296
Leu Pro Leu Asp Pro Ser Ala Met Val Ala Gln Val Gly Pro Gln Val
                420                 425                 430 gtc aac atc aac acc aaa ctg ggc tac aac aac gcc gtg ggc gcc ggg         1344
Val Asn Ile Asn Thr Lys Leu Gly Tyr Asn Asn Ala Val Gly Ala Gly
            435                 440                 445 acc ggc atc gtc atc gat ccc aac ggt gtc gtg ctg acc aac aac cac         1392
Thr Gly Ile Val Ile Asp Pro Asn Gly Val Val Leu Thr Asn Asn His
        450                 455                 460 gtg atc gcg ggc gcc acc gac atc aat gcg ttc agc gtc ggc tcc ggc         1440
Val Ile Ala Gly Ala Thr Asp Ile Asn Ala Phe Ser Val Gly Ser Gly
465                 470                 475                 480 caa acc tac ggc gtc gat gtg gtc ggg tat gac cgc acc cag gat gtc         1488
```

```
                gcg  gtg  ctg  cag  ctg  cgc  ggt  gcc  ggt  ggc  ctg  ccg  tcg  gcg  gcg  atc    1536
                Ala  Val  Leu  Gln  Leu  Arg  Gly  Ala  Gly  Gly  Leu  Pro  Ser  Ala  Ala  Ile
                          500                      505                      510 ggt  ggc  ggc  gtc  gcg  gtt  ggt  gag  ccc  gtc  gtc  gcg  atg  ggc  aac  agc    1584
                Gly  Gly  Gly  Val  Ala  Val  Gly  Glu  Pro  Val  Val  Ala  Met  Gly  Asn  Ser
                               515                      520                      525 ggt  ggg  cag  ggc  gga  acg  ccc  cgt  gcg  gtg  cct  ggc  agg  gtg  gtc  gcg    1632
                Gly  Gly  Gln  Gly  Gly  Thr  Pro  Arg  Ala  Val  Pro  Gly  Arg  Val  Val  Ala
                     530                      535                      540 ctc  ggc  caa  acc  gtg  cag  gcg  tcg  gat  tcg  ctg  acc  ggt  gcc  gaa  gag    1680
                Leu  Gly  Gln  Thr  Val  Gln  Ala  Ser  Asp  Ser  Leu  Thr  Gly  Ala  Glu  Glu
                545                      550                      555                      560 aca  ttg  aac  ggg  ttg  atc  cag  ttc  gat  gcc  gcg  atc  cag  ccc  ggt  gat    1728
                Thr  Leu  Asn  Gly  Leu  Ile  Gln  Phe  Asp  Ala  Ala  Ile  Gln  Pro  Gly  Asp
                               565                      570                      575 tcg  ggc  ggg  ccc  gtc  gtc  aac  ggc  cta  gga  cag  gtg  gtc  ggt  atg  aac    1776
                Ser  Gly  Gly  Pro  Val  Val  Asn  Gly  Leu  Gly  Gln  Val  Val  Gly  Met  Asn
                          580                      585                      590 acg  gcc  gcg  tcc  tag  gatatc                                                   1797
                Thr  Ala  Ala  Ser
                          595

<210> SEQ ID NO 20
<211> LENGTH: 596
<212> TYPE: PRT
<213> ORGANISM: Artificial Sequence
<220> FEATURE:
<223> OTHER INFORMATION: Description of Artificial Sequence:bi-fusion
      protein TbH9-Ra35 (designated MTB59F)

<400> SEQUENCE: 20

His  Met  His  His  His  His  His  Met  Val  Asp  Phe  Gly  Ala  Leu  Pro
  1                5                       10                      15

Pro  Glu  Ile  Asn  Ser  Ala  Arg  Met  Tyr  Ala  Gly  Pro  Gly  Ser  Ala  Ser
               20                      25                      30

Leu  Val  Ala  Ala  Gln  Met  Trp  Asp  Ser  Val  Ala  Ser  Asp  Leu  Phe
          35                      40                      45

Ser  Ala  Ala  Ser  Ala  Phe  Gln  Ser  Val  Val  Trp  Gly  Leu  Thr  Val  Gly
     50                      55                      60

Ser  Trp  Ile  Gly  Ser  Ser  Ala  Gly  Leu  Met  Val  Ala  Ala  Ser  Pro
 65                      70                      75                      80

Tyr  Val  Ala  Trp  Met  Ser  Val  Thr  Ala  Gly  Gln  Ala  Glu  Leu  Thr  Ala
                    85                      90                      95

Ala  Gln  Val  Arg  Val  Ala  Ala  Ala  Tyr  Glu  Thr  Ala  Tyr  Gly  Leu
               100                     105                     110

Thr  Val  Pro  Pro  Pro  Val  Ile  Ala  Glu  Asn  Arg  Ala  Glu  Leu  Met  Ile
          115                     120                     125

Leu  Ile  Ala  Thr  Asn  Leu  Leu  Gly  Gln  Asn  Thr  Pro  Ala  Ile  Ala  Val
     130                     135                     140

Asn  Glu  Ala  Glu  Tyr  Gly  Glu  Met  Trp  Ala  Gln  Asp  Ala  Ala  Met
145                     150                     155                     160

Phe  Gly  Tyr  Ala  Ala  Ala  Thr  Ala  Thr  Ala  Thr  Leu  Leu  Pro
               165                     170                     175

Phe  Glu  Glu  Ala  Pro  Glu  Met  Thr  Ser  Ala  Gly  Gly  Leu  Leu  Glu  Gln
          180                     185                     190

Ala  Ala  Ala  Val  Glu  Glu  Ala  Ser  Asp  Thr  Ala  Ala  Ala  Asn  Gln  Leu
     195                     200                     205
```

-continued

Met Asn Val Pro Gln Ala Leu Gln Gln Leu Ala Gln Pro Thr Gln
    210                 215                 220

Gly Thr Thr Pro Ser Ser Lys Leu Gly Gly Leu Trp Lys Thr Val Ser
225                 230                 235                 240

Pro His Arg Ser Pro Ile Ser Asn Met Val Ser Met Ala Asn Asn His
                245                 250                 255

Met Ser Met Thr Asn Ser Gly Val Ser Met Thr Asn Thr Leu Ser Ser
            260                 265                 270

Met Leu Lys Gly Phe Ala Pro Ala Ala Ala Gln Ala Val Gln Thr
        275                 280                 285

Ala Ala Gln Asn Gly Val Arg Ala Met Ser Ser Leu Gly Ser Ser Leu
    290                 295                 300

Gly Ser Ser Gly Leu Gly Gly Val Ala Ala Asn Leu Gly Arg Ala
305                 310                 315                 320

Ala Ser Val Gly Ser Leu Ser Val Pro Gln Ala Trp Ala Ala Ala Asn
                325                 330                 335

Gln Ala Val Thr Pro Ala Ala Arg Ala Leu Pro Leu Thr Ser Leu Thr
            340                 345                 350

Ser Ala Ala Glu Arg Gly Pro Gly Gln Met Leu Gly Gly Leu Pro Val
        355                 360                 365

Gly Gln Met Gly Ala Arg Ala Gly Gly Leu Ser Gly Val Leu Arg
370                 375                 380

Val Pro Pro Arg Pro Tyr Val Met Pro His Ser Pro Ala Ala Gly Asp
385                 390                 395                 400

Ile Ala Pro Pro Ala Leu Ser Gln Asp Arg Phe Ala Asp Phe Pro Ala
                405                 410                 415

Leu Pro Leu Asp Pro Ser Ala Met Val Ala Gln Val Gly Pro Gln Val
            420                 425                 430

Val Asn Ile Asn Thr Lys Leu Gly Tyr Asn Asn Ala Val Gly Ala Gly
        435                 440                 445

Thr Gly Ile Val Ile Asp Pro Asn Gly Val Val Leu Thr Asn Asn His
450                 455                 460

Val Ile Ala Gly Ala Thr Asp Ile Asn Ala Phe Ser Val Gly Ser Gly
465                 470                 475                 480

Gln Thr Tyr Gly Val Asp Val Val Gly Tyr Asp Arg Thr Gln Asp Val
                485                 490                 495

Ala Val Leu Gln Leu Arg Gly Ala Gly Gly Leu Pro Ser Ala Ala Ile
            500                 505                 510

Gly Gly Gly Val Ala Val Gly Glu Pro Val Val Ala Met Gly Asn Ser
        515                 520                 525

Gly Gly Gln Gly Gly Thr Pro Arg Ala Val Pro Gly Arg Val Val Ala
530                 535                 540

Leu Gly Gln Thr Val Gln Ala Ser Asp Ser Leu Thr Gly Ala Glu Glu
545                 550                 555                 560

Thr Leu Asn Gly Leu Ile Gln Phe Asp Ala Ala Ile Gln Pro Gly Asp
                565                 570                 575

Ser Gly Gly Pro Val Val Asn Gly Leu Gly Gln Val Val Gly Met Asn
            580                 585                 590

Thr Ala Ala Ser
        595

<210> SEQ ID NO 21
<211> LENGTH: 500
<212> TYPE: DNA

<213> ORGANISM: Mycobacterium tuberculosis
<220> FEATURE:
<223> OTHER INFORMATION: MTB8.4 (DPV) cDNA

<400> SEQUENCE: 21
cgtggcaatg tcgttgaccg tcggggccgg ggtcgcctcc gcagatcccg tggacgcggt 60
cattaacacc acctgcaatt acgggcaggt agtagctgcg ctcaacgcga cggatccggg 120
ggctgccgca cagttcaacg cctcaccggt ggcgcagtcc tatttgcgca atttcctcgc 180
cgcaccgcca cctcagcgcg ctgccatggc cgcgcaattg caagctgtgc cgggggcggc 240
acagtacatc ggccttgtcg agtcggttgc cggctcctgc aacaactatt aagcccatgc 300
gggccccatc ccgcgacccg gcatcgtcgc cggggctagg ccagattgcc ccgctcctca 360
acgggccgca tcccgcgacc cggcatcgtc gccggggcta ggccagattg ccccgctcct 420
caacgggccg catctcgtgc cgaattcctg cagcccgggg gatccactag ttctagagcg 480
gccgccaccg cggtggagct 500

<210> SEQ ID NO 22
<211> LENGTH: 96
<212> TYPE: PRT
<213> ORGANISM: Mycobacterium tuberculosis
<220> FEATURE:
<223> OTHER INFORMATION: MTB8.4 (DPV)

<400> SEQUENCE: 22

Val Ala Met Ser Leu Thr Val Gly Ala Gly Val Ala Ser Ala Asp Pro
1 5 10 15

Val Asp Ala Val Ile Asn Thr Thr Cys Asn Tyr Gly Gln Val Val Ala
20 25 30

Ala Leu Asn Ala Thr Asp Pro Gly Ala Ala Ala Gln Phe Asn Ala Ser
35 40 45

Pro Val Ala Gln Ser Tyr Leu Arg Asn Phe Leu Ala Ala Pro Pro Pro
50 55 60

Gln Arg Ala Ala Met Ala Ala Gln Leu Gln Ala Val Pro Gly Ala Ala
65 70 75 80

Gln Tyr Ile Gly Leu Val Glu Ser Val Ala Gly Ser Cys Asn Asn Tyr
85 90 95

<210> SEQ ID NO 23
<211> LENGTH: 585
<212> TYPE: DNA
<213> ORGANISM: Mycobacterium tuberculosis
<220> FEATURE:
<223> OTHER INFORMATION: MTB9.8 (MSL)

<400> SEQUENCE: 23
tggattccga tagcggtttc ggcccctcga cgggcgacca cggcgcgcag gcctccgaac 60 gggggccgg gacgctggga ttcgccggga ccgcaaccaa agaacgccgg gtccgggcgg 120
tcgggctgac cgcactggcc ggtgatgagt tcggcaacgg cccccggatg ccgatggtgc 180
cggggacctg ggagcagggc agcaacgagc ccgaggcgcc cgacggatcg gggagagggg 240
gaggcgacgg cttaccgcac gacagcaagt aaccgaattc cgaatcacgt ggacccgtac 300
gggtcgaaag gagagatgtt atgagccttt tggatgctca tatcccacag ttggtggcct 360
cccagtcggc gtttgccgcc aaggcggggc tgatgcggca cacgatcggt caggccgagc 420
aggcggcgat gtcggctcag gcgtttcacc agggggagtc gtcggcggcg tttcaggccg 480
cccatgcccg gtttgtggcg gcggccgcca aagtcaacac cttgttggat gtcgcgcagg 540

```
cgaatctggg tgaggccgcc ggtacctatg tggccgccga tgctg              585
```

<210> SEQ ID NO 24
<211> LENGTH: 97
<212> TYPE: PRT
<213> ORGANISM: Mycobacterium tuberculosis
<220> FEATURE:
<223> OTHER INFORMATION: MTB9.8 (MSL)

<400> SEQUENCE: 24

```
Met Ser Leu Leu Asp Ala His Ile Pro Gln Leu Val Ala Ser Gln Ser
 1               5                  10                  15

Ala Phe Ala Ala Lys Ala Gly Leu Met Arg His Thr Ile Gly Gln Ala
             20                  25                  30

Glu Gln Ala Ala Met Ser Ala Gln Ala Phe His Gln Gly Glu Ser Ser
         35                  40                  45

Ala Ala Phe Gln Ala Ala His Ala Arg Phe Val Ala Ala Ala Ala Lys
     50                  55                  60

Val Asn Thr Leu Leu Asp Val Ala Gln Ala Asn Leu Gly Glu Ala Ala
 65                  70                  75                  80

Gly Thr Tyr Val Ala Ala Asp Ala Ala Ala Ser Thr Tyr Thr Gly
                 85                  90                  95

Phe
```

<210> SEQ ID NO 25
<211> LENGTH: 1742
<212> TYPE: DNA
<213> ORGANISM: Mycobacterium tuberculosis
<220> FEATURE:
<223> OTHER INFORMATION: MTB9.9A (MTI, also known as MTI-A)
<220> FEATURE:
<221> NAME/KEY: modified_base
<222> LOCATION: (1)..(1742)
<223> OTHER INFORMATION: n = g, a, c or t

<400> SEQUENCE: 25

```
ccgctctctt tcaacgtcat aagttcggtg ggccagtcgg ccgcgcgtgc atatggcacc    60
aataacgcgt gtcccatgga tacccggacc gcacgacggg agagcggatc agcgcagccg   120
gtgccgaaca ctaccgcgtc cacgctcagc cctgccgcgt tgcggaagat cgagcccagg   180
ttctcatggt cgttaacgcc ttccaacact gcgacggtgc gcgccccggc gaccacctga   240
gcaacgctcg gctccggcac ccggcgcgcg gctgccaaca ccccacgatt gagatggaag   300
ccgatcaccc gtgccatgac atcagccgac gctcgatagt acggcgcgcc gacaccggcc   360
agatcatcct tgagctcggc cagccggcgg tcggtgccga acagcgccag cggcgtgaac   420
cgtgaggcca gcatgcgctg caccaccagc acaccctcgg cgatcaccaa cgccttgccg   480
gtcggcagat cggacncacn gtcgatgctg ttcaggtcac ggaaatcgtc gagccgtggg   540
tcgtcgggat cgcagacgtc ctgaacatcg aggccgtcgg ggtgctgggc acaacggcct   600
tcggtcacgg gctttcgtcg accagagcca gcatcagatc ggcggcgctg cgcaggatgt   660
cacgctcgct gcggttcagc gtcgcgagcc gctcagccag ccactcttgc agagagccgt   720
tgctgggatt aattgggaga ggaagacagc atgtcgttcg tgaccacaca gccggaagcc   780
ctggcagctg cggcggcgaa cctacagggt attggcacga caatgaacgc cagaacgcg   840 gccgcggctg ctccaaccac cggagtagtg cccgcagccg ccgatgaagt atcagcgctg   900
accgcggctc agtttgctgc gcacgcgcag atgtaccaaa cggtcagcgc ccaggccgcg   960
gccattcacg aaatgttcgt gaacacgctg gtggccagtt ctggctcata cgcggccacc  1020
```

```
gaggcggcca acgcagccgc tgccggctga acgggctcgc acgaacctgc tgaaggagag    1080
ggggaacatc cggagttctc gggtcagggg ttgcgccagc gcccagccga ttcagntatc    1140
ggcgtccata acagcagacg atctaggcat tcagtactaa ggagacaggc aacatggcct    1200
cacgttttat gacggatccg catgcgatgc gggacatggc gggccgtttt gaggtgcacg    1260
cccagacggt ggaggacgag gctcgccgga tgtgggcgtc cgcgcaaaac atttccggtg    1320
cgggctggag tggcatggcc gaggcgacct cgctagacac catgacctag atgaatcagg    1380
cgtttcgcaa catcgtgaac atgctgcacg gggtgcgtga cgggctggtt cgcgacgcca    1440
acaantacga acagcaagag caggcctccc agcagatcct gagcagntag cgccgaaagc    1500
cacagctgng tacgntttct cacattagga gaacaccaat atgacgatta attaccagtt    1560
cggggacgtc gacgctcatg cgccatgat ccgcgctcag gcggcgtcgc ttgaggcgga    1620
gcatcaggcc atcgttcgtg atgtgttggc gcgggtgac ttttggggcg gcgccggttc    1680
ggtggcttgc caggagttca ttacccagtt gggccgtaac ttccaggtga tctacgagca    1740
gg                                                                  1742

<210> SEQ ID NO 26
<211> LENGTH: 2836
<212> TYPE: DNA
<213> ORGANISM: Mycobacterium tuberculosis
<220> FEATURE:
<223> OTHER INFORMATION: MTB9.9A (MTI also known as MTI-A)
<220> FEATURE:
<221> NAME/KEY: modified_base
<222> LOCATION: (104)
<223> OTHER INFORMATION: n = g, a, c or t

<400> SEQUENCE: 26
gttgattccg ttcgcggcgc cgccgaagac caccaactcc gctggggtgg tcgcacaggc     60
ggttgcgtcg gtcagctggc cgaatcccaa tgattggtgg ctcngtgcgg ttgctgggct    120
cgattacccc cacggaaagg acgacgatcg ttcgtttgct cggtcagtcg tacttggcga    180
cgggcatggc gcggttttctt acctcgatcg cacagcagct gaccttcggc ccagggggca    240
caacggctgg ctccggcgga gcctggtacc caacgccaca attcgccggc ctgggtgcag    300
gcccggcggt gtcggcgagt ttggcgcggg cggagccggt cgggaggttg tcggtgccgc    360
caagttgggc cgtcgcggct ccggccttcg cggagaagcc tgaggcgggc acgccgatgt    420
ccgtcatcgg cgaagcgtcc agctgcggtc agggaggcct gcttcgaggc ataccgctgg    480
cgagagcggg gcggcgtaca ggcgccttcg ctcaccgata cggttccgc cacagcgtga    540 ttacccggtc tccgtcggcg ggatagcttt cgatccggtc tgcgcggccg ccggaaatgc    600
tgcagatagc gatcgaccgc gccggtcggt aaacgccgca cacggcacta tcaatgcgca    660
cggcgggcgt tgatgccaaa ttgaccgtcc cgacggggct ttatctgcgg caagatttca    720
tccccagccc ggtcggtggg ccgataaata cgctggtcag cgcgactctt ccggctgaat    780
tcgatgctct gggcgcccgc tcgacgccga gtatctcgag tgggccgcaa acccggtcaa    840
acgctgttac tgtggcgtta ccacaggtga atttgcggtg ccaactggtg aacacttgcg    900
aacgggtggc atcgaaatca acttgttgcg ttgcagtgat ctactctctt gcagagagcc    960
gttgctggga ttaattggga gaggaagaca gcatgtcgtt cgtgaccaca cagccggaag   1020
ccctggcagc tgcggcggcg aacctacagg gtattggcac gacaatgaac gcccagaacg   1080
cggccgcggc tgctccaacc accggagtag tgcccgcagc cgccgatgaa gtatcagcgc   1140
tgaccgcggc tcagtttgct gcgcacgcgc agatgtacca aacggtcagc gcccaggccg   1200
```

-continued

```
cggccattca cgaaatgttc gtgaacacgc tggtggccag ttctggctca tacgcggcca   1260
ccgaggcggc caacgcagcc gctgccggct gaacgggctc gcacgaacct gctgaaggag   1320
agggggaaca tccggagttc tcgggtcagg ggttgcgcca gcgcccagcc gattcagcta   1380
tcggcgtcca taacagcaga cgatctaggc attcagtact aaggagacag gcaacatggc   1440
ctcacgtttt atgacggatc cgcatgcgat gcgggacatg gcgggccgtt ttgaggtgca   1500
cgcccagacg gtggaggacg aggctcgccg gatgtgggcg tccgcgcaaa acatttccgg   1560
tgcgggctgg agtggcatgg ccgaggcgac ctcgctagac accatgacct agatgaatca   1620
ggcgtttcgc aacatcgtga acatgctgca cggggtgcgt gacgggctgg ttcgcgacgc   1680
caacaactac gaacagcaag agcaggcctc ccagcagatc ctgagcagct agcgccgaaa   1740
gccacagctg cgtacgcttt ctcacattag gagaacacca atatgacgat taattaccag   1800
ttcggggacg tcgacgctca tggcgccatg atccgcgctc aggcggcgtc gcttgaggcg   1860
gagcatcagg ccatcgttcg tgatgtgttg gccgcgggtg acttttgggg cggcgccggt   1920
tcggtggctt gccaggagtt cattacccag ttgggccgta acttccaggt gatctacgag   1980
caggccaacg cccacgggca gaaggtgcag gctgccggca acaacatggc gcaaaccgac   2040
agcgccgtcg gctccagctg ggcctaaaac tgaacttcag tcgcggcagc acaccaacca   2100
gccggtgtgc tgctgtgtcc tgcagttaac tagcactcga ccgctgaggt agcgatggat   2160
caacagagta cccgcaccga catcaccgtc aacgtcgacg gcttctggat gcttcaggcg   2220
ctactggata tccgccacgt tgcgcctgag ttacgttgcc ggccgtacgt ctccaccgat   2280
tccaatgact ggctaaacga gcacccgggg atggcggtca tgcgcgagca gggcattgtc   2340
gtcaacgacg cggtcaacga acaggtcgct gcccggatga aggtgcttgc cgcacctgat   2400
cttgaagtcg tcgccctgct gtcacgcggc aagttgctgt acggggtcat agacgacgag   2460
aaccagccgc cgggttcgcg tgacatccct gacaatgagt tccgggtggt gttggcccgg   2520
cgaggccagc actgggtgtc ggcggtacgg gttggcaatg acatcaccgt cgatgacgtg   2580
acggtctcgg atagcgcctc gatcgccgca ctggtaatgg acggtctgga gtcgattcac   2640
cacgccgacc cagccgcgat caacgcggtc aacgtgccaa tggaggagat ctcgtgccga   2700
attcggcacg aggcacgagg cggtgtcggt gacgacggga tcgatcacga tcatcgaccg   2760
gccgggatcc ttggcgatct cgttgagcac gacccgggcc cgcgggaagc tctgcgacat   2820
ccatgggttc ttcccg                                                   2836
```

```

<210> SEQ ID NO 27
<211> LENGTH: 94
<212> TYPE: PRT
<213> ORGANISM: Mycobacterium tuberculosis
<220> FEATURE:
<223> OTHER INFORMATION: MTB9.9A (MTI, also known as MTI-A) ORF peptide

<400> SEQUENCE: 27

Met Thr Ile Asn Tyr Gln Phe Gly Asp Val Asp Ala His Gly Ala Met
  1               5                  10                  15

Ile Arg Ala Leu Ala Gly Leu Leu Glu Ala Glu His Gln Ala Ile Ile
             20                  25                  30

Ser Asp Val Leu Thr Ala Ser Asp Phe Trp Gly Gly Ala Gly Ser Ala
         35                  40                  45

Ala Cys Gln Gly Phe Ile Thr Gln Leu Gly Arg Asn Phe Gln Val Ile
     50                  55                  60

Tyr Glu Gln Ala Asn Ala His Gly Gln Lys Val Gln Ala Ala Gly Asn
 65                  70                  75                  80
```

-continued

Asn Met Ala Gln Thr Asp Ser Ala Val Gly Ser Ser Trp Ala
            85                  90

<210> SEQ ID NO 28
<211> LENGTH: 1200
<212> TYPE: DNA
<213> ORGANISM: Mycobacterium tuberculosis
<220> FEATURE:
<223> OTHER INFORMATION: MTB40 (HTCC#1) cDNA

<400> SEQUENCE: 28

```
caggcatgag cagagcgttc atcatcgatc caacgatcag tgccattgac ggcttgtacg      60
accttctggg gattggaata cccaaccaag ggggtatcct ttactcctca ctagagtact     120
tcgaaaaagc cctggaggag ctggcagcag cgtttccggg tgatggctgg ttaggttcgg     180
ccgcggacaa atacgccggc aaaaaccgca accacgtgaa tttttccag gaactggcag      240
acctcgatcg tcagctcatc agcctgatcc acgaccaggc caacgcggtc cagacgaccc     300
gcgacatcct ggagggcgcc aagaaaggtc tcgagttcgt gcgcccggtg gctgtggacc     360
tgacctacat cccggtcgtc gggcacgccc tatcggccgc cttccaggcg ccgttttgcg     420
cgggcgcgat ggccgtagtg ggcggcgcgc ttgcctactt ggtcgtgaaa acgctgatca     480
acgcgactca actcctcaaa ttgcttgcca aattggcgga gttggtcgcg ccgccattg      540
cggacatcat ttcggatgtg gcggacatca tcaagggcac cctcggagaa gtgtgggagt     600
tcatcacaaa cgcgctcaac ggcctgaaag agctttggga caagctcacg gggtgggtga     660
ccggactgtt ctctcgaggg tggtcgaacc tggagtcctt ctttgcgggc gtccccggct     720
tgaccggcgc gaccagcggc ttgtcgcaag tgactggctt gttcggtgcg gccggtctgt     780
ccgcatcgtc gggcttggct cacgcggata gcctggcgag ctcagccagc ttgcccgccc     840
tggccggcat tggggcggg tccggttttg ggggcttgcc gagcctggct caggtccatg      900
ccgcctcaac tcgcaggcg ctacggcccc gagctgatgg cccggtcggc gccgctgccg      960
agcaggtcgg cggcagtcg cagctggtct ccgcgcaggg ttcccaaggt atgggcggac     1020
ccgtaggcat gggcggcatg caccctctt cgggggcgtc gaaagggacg acgacgaaga     1080
agtactcgga aggcgcggcg gcgggcactg aagacgccga gcgcgcgcca gtcgaagctg     1140
acgcgggcgg tgggcaaaag gtgctggtac gaaacgtcgt ctaacggcat ggcgagccaa     1200
```

<210> SEQ ID NO 29
<211> LENGTH: 392
<212> TYPE: PRT
<213> ORGANISM: Mycobacterium tuberculosis
<220> FEATURE:
<223> OTHER INFORMATION: MTB40 (HTCC#1)

<400> SEQUENCE: 29

Met Ser Arg Ala Phe Ile Ile Asp Pro Thr Ile Ser Ala Ile Asp Gly
 1               5                  10                  15

Leu Tyr Asp Leu Leu Gly Ile Gly Ile Pro Asn Gln Gly Gly Ile Leu
                20                  25                  30

Tyr Ser Ser Leu Glu Tyr Phe Glu Lys Ala Leu Glu Glu Leu Ala Ala
            35                  40                  45

Ala Phe Pro Gly Asp Gly Trp Leu Gly Ser Ala Ala Asp Lys Tyr Ala
        50                  55                  60

Gly Lys Asn Arg Asn His Val Asn Phe Phe Gln Glu Leu Ala Asp Leu
65                  70                  75                  80

Asp Arg Gln Leu Ile Ser Leu Ile His Asp Gln Ala Asn Ala Val Gln

-continued

```
                85                  90                  95

Thr Thr Arg Asp Ile Leu Glu Gly Ala Lys Lys Gly Leu Glu Phe Val
            100                 105                 110

Arg Pro Val Ala Val Asp Leu Thr Tyr Ile Pro Val Val Gly His Ala
        115                 120                 125

Leu Ser Ala Ala Phe Gln Ala Pro Phe Cys Ala Gly Ala Met Ala Val
    130                 135                 140

Val Gly Gly Ala Leu Ala Tyr Leu Val Val Lys Thr Leu Ile Asn Ala
145                 150                 155                 160

Thr Gln Leu Leu Lys Leu Leu Ala Lys Leu Ala Glu Leu Val Ala Ala
                165                 170                 175

Ala Ile Ala Asp Ile Ile Ser Asp Val Ala Asp Ile Ile Lys Gly Thr
            180                 185                 190

Leu Gly Glu Val Trp Glu Phe Ile Thr Asn Ala Leu Asn Gly Leu Lys
        195                 200                 205

Glu Leu Trp Asp Lys Leu Thr Gly Trp Val Thr Gly Leu Phe Ser Arg
    210                 215                 220

Gly Trp Ser Asn Leu Glu Ser Phe Phe Ala Gly Val Pro Gly Leu Thr
225                 230                 235                 240

Gly Ala Thr Ser Gly Leu Ser Gln Val Thr Gly Leu Phe Gly Ala Ala
                245                 250                 255

Gly Leu Ser Ala Ser Ser Gly Leu Ala His Ala Asp Ser Leu Ala Ser
            260                 265                 270

Ser Ala Ser Leu Pro Ala Leu Ala Gly Ile Gly Gly Gly Ser Gly Phe
        275                 280                 285

Gly Gly Leu Pro Ser Leu Ala Gln Val His Ala Ala Ser Thr Arg Gln
    290                 295                 300

Ala Leu Arg Pro Arg Ala Asp Gly Pro Val Gly Ala Ala Ala Glu Gln
305                 310                 315                 320

Val Gly Gly Gln Ser Gln Leu Val Ser Ala Gln Gly Ser Gln Gly Met
                325                 330                 335

Gly Gly Pro Val Gly Met Gly Gly Met His Pro Ser Ser Gly Ala Ser
            340                 345                 350

Lys Gly Thr Thr Thr Lys Lys Tyr Ser Glu Gly Ala Ala Ala Gly Thr
        355                 360                 365

Glu Asp Ala Glu Arg Ala Pro Val Glu Ala Asp Ala Gly Gly Gly Gln
    370                 375                 380

Lys Val Leu Val Arg Asn Val Val
385                 390
```

<210> SEQ ID NO 30
<211> LENGTH: 1441
<212> TYPE: DNA
<213> ORGANISM: Mycobacterium tuberculosis
<220> FEATURE:
<223> OTHER INFORMATION: MTB41 (MTCC#2) cDNA

<400> SEQUENCE: 30

```
gaggttgctg gcaatggatt tcgggctttt acctccggaa gtgaattcaa gccgaatgta     60
ttccggtccg gggccggagt cgatgctagc cgccgcggcc gcctgggacg gtgtggccgc    120
ggagttgact tccgccgcgg tctcgtatgg atcggtggtg tcgacgctga tcgttgagcc    180
gtggatgggg ccggcggcgg ccgcgatggc ggccgcggca acgccgtatg tggggtggct    240
ggccgccacg gcggcgctgg cgaaggagac ggccacacag gcgagggcag cggcggaagc    300
gtttgggacg gcgttcgcga tgacggtgcc accatccctc gtcgcggcca accgcagccg    360
```

```
gttgatgtcg ctggtcgcgg cgaacattct ggggcaaaac agtgcggcga tcgcggctac    420
ccaggccgag tatgccgaaa tgtgggccca agacgctgcc gtgatgtaca gctatgaggg    480
ggcatctgcg gccgcgtcgg cgttgccgcc gttcactcca cccgtgcaag caccggccc     540 ggccgggccc gcggccgcag ccgcggcgac ccaagccgcc ggtgcgggcg ccgttgcgga    600
tgcacaggcg acactggccc agctgccccc ggggatcctg agcgacattc tgtccgcatt    660
ggccgccaac gctgatccgc tgacatcggg actgttgggg atcgcgtcga ccctcaaccc    720
gcaagtcgga tccgctcagc cgatagtgat ccccacccg  ataggggaat tggacgtgat    780
cgcgctctac attgcatcca tcgcgaccgg cagcattgcg ctcgcgatca cgaacacggc    840
cagaccctgg cacatcggcc tatacgggaa cgccggcggg ctgggaccga cgcagggcca    900
tccactgagt tcggcgaccg acgagccgga gccgcactgg ggccccttcg ggggcgcggc    960
gccggtgtcc gcgggcgtcg gccacgcagc attagtcgga gcgttgtcgg tgccgcacag   1020
ctggaccacg gccgccccgg agatccagct cgccgttcag gcaacaccca ccttcagctc   1080
cagcgccggc gccgacccga cggccctaaa cgggatgccg gcaggcctgc tcagcgggat   1140
ggctttggcg agcctggccg cacgcggcac gacgggcggt ggcggcaccc gtagcggcac   1200
cagcactgac ggccaagagg acggccgcaa accccggta  gttgtgatta gagagcagcc   1260
gccgcccgga aaccccccgc ggtaaaagtc cggcaaccgt tcgtcgccgc gcggaaaatg   1320
cctggtgagc gtggctatcc gacgggccgt tcacaccgct tgtagtagcg tacggctatg   1380
gacgacggtg tctggattct cggcggctat cagagcgatt ttgctcgcaa cctcagcaaa   1440
g                                                                   1441
```

<210> SEQ ID NO 31
<211> LENGTH: 423
<212> TYPE: PRT
<213> ORGANISM: Mycobacterium tuberculosis
<220> FEATURE:
<223> OTHER INFORMATION: MTB41 (MTCC#2)

<400> SEQUENCE: 31

```
Met Asp Phe Gly Leu Leu Pro Pro Glu Val Asn Ser Ser Arg Met Tyr
  1               5                  10                  15

Ser Gly Pro Gly Pro Glu Ser Met Leu Ala Ala Ala Ala Ala Trp Asp
             20                  25                  30

Gly Val Ala Ala Glu Leu Thr Ser Ala Ala Val Ser Tyr Gly Ser Val
         35                  40                  45

Val Ser Thr Leu Ile Val Glu Pro Trp Met Gly Pro Ala Ala Ala Ala
     50                  55                  60

Met Ala Ala Ala Ala Thr Pro Tyr Val Gly Trp Leu Ala Thr Ala
 65                  70                  75                  80

Ala Leu Ala Lys Glu Thr Ala Thr Gln Ala Arg Ala Ala Ala Glu Ala
                 85                  90                  95

Phe Gly Thr Ala Phe Ala Met Thr Val Pro Pro Ser Leu Val Ala Ala
            100                 105                 110

Asn Arg Ser Arg Leu Met Ser Leu Val Ala Ala Asn Ile Leu Gly Gln
        115                 120                 125

Asn Ser Ala Ala Ile Ala Ala Thr Gln Ala Glu Tyr Ala Glu Met Trp
    130                 135                 140

Ala Gln Asp Ala Ala Val Met Tyr Ser Tyr Glu Gly Ala Ser Ala Ala
145                 150                 155                 160

Ala Ser Ala Leu Pro Pro Phe Thr Pro Pro Val Gln Gly Thr Gly Pro
```

```
                    165                 170                 175
Ala Gly Pro Ala Ala Ala Ala Ala Thr Gln Ala Gly Ala Gly
            180                 185                 190

Ala Val Ala Asp Ala Gln Ala Thr Leu Ala Gln Leu Pro Gly Ile
            195                 200                 205

Leu Ser Asp Ile Leu Ser Ala Leu Ala Asn Ala Asp Pro Leu Thr
            210                 215                 220

Ser Gly Leu Leu Gly Ile Ala Ser Thr Leu Asn Pro Gln Val Gly Ser
225                 230                 235                 240

Ala Gln Pro Ile Val Ile Pro Thr Pro Ile Gly Glu Leu Asp Val Ile
                245                 250                 255

Ala Leu Tyr Ile Ala Ser Ile Ala Thr Gly Ser Ile Ala Leu Ala Ile
                260                 265                 270

Thr Asn Thr Ala Arg Pro Trp His Ile Gly Leu Tyr Gly Asn Ala Gly
            275                 280                 285

Gly Leu Gly Pro Thr Gln Gly His Pro Leu Ser Ser Ala Thr Asp Glu
            290                 295                 300

Pro Glu Pro His Trp Gly Pro Phe Gly Gly Ala Ala Pro Val Ser Ala
305                 310                 315                 320

Gly Val Gly His Ala Ala Leu Val Gly Ala Leu Ser Val Pro His Ser
                325                 330                 335

Trp Thr Thr Ala Ala Pro Glu Ile Gln Leu Ala Val Gln Ala Thr Pro
                340                 345                 350

Thr Phe Ser Ser Ser Ala Gly Ala Asp Pro Thr Ala Leu Asn Gly Met
            355                 360                 365

Pro Ala Gly Leu Leu Ser Gly Met Ala Leu Ala Ser Leu Ala Ala Arg
            370                 375                 380

Gly Thr Thr Gly Gly Gly Gly Thr Arg Ser Gly Thr Ser Thr Asp Gly
385                 390                 395                 400

Gln Glu Asp Gly Arg Lys Pro Pro Val Val Val Ile Arg Glu Gln Pro
                405                 410                 415

Pro Pro Gly Asn Pro Pro Arg
            420

<210> SEQ ID NO 32
<211> LENGTH: 154
<212> TYPE: DNA
<213> ORGANISM: Mycobacterium tuberculosis
<220> FEATURE:
<223> OTHER INFORMATION: ESAT-6

<400> SEQUENCE: 32
atgacagagc agcagtggaa tttcgcgggt atcgaggccg cggcaagcgc aatccaggga      60
aatgtcacgt ccattcattc cctccttgac gaggggaagc agtccctgac caagctcgca     120
gcggcctggg gcggtagcgg ttcggaagcg tacc                                 154

<210> SEQ ID NO 33
<211> LENGTH: 51
<212> TYPE: PRT
<213> ORGANISM: Mycobacterium tuberculosis
<220> FEATURE:
<223> OTHER INFORMATION: ESAT-6

<400> SEQUENCE: 33

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
```

```
                        20                  25                  30

Lys Gln Ser Leu Thr Lys Leu Ala Ala Ala Trp Gly Gly Ser Gly Ser
             35                  40                  45

Glu Ala Tyr
    50

<210> SEQ ID NO 34
<211> LENGTH: 327
<212> TYPE: DNA
<213> ORGANISM: Mycobacterium tuberculosis
<220> FEATURE:
<223> OTHER INFORMATION: Tb38-1 or 38-1 (MTb11)

<400> SEQUENCE: 34
cggcacgaga gaccgatgcc gctaccctcg cgcaggaggc aggtaatttc gagcggatct      60
ccggcgacct gaaaacccag atcgaccagg tggagtcgac ggcaggttcg ttgcagggcc     120
agtggcgcgg cgcggcgggg acggccgccc aggccgcggt ggtgcgcttc caagaagcag     180
ccaataagca gaagcaggaa ctcgacgaga tctcgacgaa tattcgtcag gccggcgtcc     240
aatactcgag ggccgacgag gagcagcagc aggcgctgtc ctcgcaaatg ggcttctgac     300
ccgctaatac gaaagaaac ggagcaa                                          327

<210> SEQ ID NO 35
<211> LENGTH: 95
<212> TYPE: PRT
<213> ORGANISM: Mycobacterium tuberculosis
<220> FEATURE:
<223> OTHER INFORMATION: Tb38-1 or 38-1 (MTb11)

<400> SEQUENCE: 35

Thr Asp Ala Ala Thr Leu Ala Gln Glu Ala Gly Asn Phe Glu Arg Ile
  1               5                  10                  15

Ser Gly Asp Leu Lys Thr Gln Ile Asp Gln Val Glu Ser Thr Ala Gly
                 20                  25                  30

Ser Leu Gln Gly Gln Trp Arg Gly Ala Ala Gly Thr Ala Ala Gln Ala
             35                  40                  45

Ala Val Val Arg Phe Gln Glu Ala Ala Asn Lys Gln Lys Gln Glu Leu
         50                  55                  60

Asp Glu Ile Ser Thr Asn Ile Arg Gln Ala Gly Val Gln Tyr Ser Arg
 65                  70                  75                  80

Ala Asp Glu Glu Gln Gln Gln Ala Leu Ser Ser Gln Met Gly Phe
                 85                  90                  95

<210> SEQ ID NO 36
<211> LENGTH: 542
<212> TYPE: DNA
<213> ORGANISM: Mycobacterium tuberculosis
<220> FEATURE:
<223> OTHER INFORMATION: TbRa3
<220> FEATURE:
<221> NAME/KEY: modified_base
<222> LOCATION: (406)
<223> OTHER INFORMATION: n = g, a, c or t

<400> SEQUENCE: 36
gaattcggca cgagaggtga tcgacatcat cgggaccagc cccacatcct gggaacaggc      60
ggcggcggag gcggtccagc gggcgcggga tagcgtcgat gacatccgcg tcgctcgggt     120
cattgagcag gacatggccg tggacagcgc cggcaagatc acctaccgca tcaagctcga     180
agtgtcgttc aagatgaggc cggcgcaacc gcgctagcac gggccggcga gcaagacgca     240
```

```
aaatcgcacg gtttgcggtt gattcgtgcg attttgtgtc tgctcgccga ggcctaccag    300
gcgcggccca ggtccgcgtg ctgccgtatc caggcgtgca tcgcgattcc ggcggccacg    360
ccggagttaa tgcttcgcgt cgacccgaac tgggcgatcc gccggngagc tgatcgatga    420
ccgtggccag cccgtcgatg cccgagttgc ccgaggaaac gtgctgccag ccggtagga    480 agcgtccgta gcggcggtg ctgaccggct ctgcctgcgc cctcagtgcg ccagcgagc    540 gg                                                                  542
```

<210> SEQ ID NO 37
<211> LENGTH: 66
<212> TYPE: PRT
<213> ORGANISM: Mycobacterium tuberculosis
<220> FEATURE:
<223> OTHER INFORMATION: TbRa3

<400> SEQUENCE: 37

Val Ile Asp Ile Ile Gly Thr Ser Pro Thr Ser Trp Glu Gln Ala Ala
 1               5                  10                  15

Ala Glu Ala Val Gln Arg Ala Arg Asp Ser Val Asp Asp Ile Arg Val
            20                  25                  30

Ala Arg Val Ile Glu Gln Asp Met Ala Val Asp Ser Ala Gly Lys Ile
        35                  40                  45

Thr Tyr Arg Ile Lys Leu Glu Val Ser Phe Lys Met Arg Pro Ala Gln
    50                  55                  60

Pro Arg
 65

<210> SEQ ID NO 38
<211> LENGTH: 1993
<212> TYPE: DNA
<213> ORGANISM: Mycobacterium tuberculosis
<220> FEATURE:
<223> OTHER INFORMATION: 38 kD

<400> SEQUENCE: 38

```
tgttcttcga cggcaggctg gtggaggaag ggcccaccga acagctgttc tcctcgccga     60
agcatgcgga aaccgcccga tacgtcgccg gactgtcggg ggacgtcaag gacgccaagc    120
gcggaaattg aagagcacag aaaggtatgg cgtgaaaatt cgtttgcata cgctgttggc    180
cgtgttgacc gctgcgccgc tgctgctagc agcggcgggc tgtggctcga aaccaccgag    240
cggttcgcct gaaacgggcg ccggcgccgg tactgtcgcg actaccccg cgtcgtcgcc     300 ggtgacgttg gcggagaccg gtagcacgct gctctacccg ctgttcaacc tgtggggtcc    360 ggccttttcac gagaggtatc cgaacgtcac gatcaccgct cagggcaccg gttctggtgc    420
cgggatcgcg caggccgccg ccgggacggt caacattggg gcctccgacg cctatctgtc    480
ggaaggtgat atggccgcgc acaagggggct gatgaacatc gcgctagcca tctccgctca    540
gcaggtcaac tacaacctgc ccggagtgag cgagcacctc aagctgaacg gaaaagtcct    600
ggcggccatg taccagggca ccatcaaaac ctgggacgac ccgcagatcg ctgcgctcaa    660
ccccggcgtg aacctgcccg gcaccgcggt agttccgctg caccgctccg acgggtccgg    720
tgacaccttc ttgttcaccc agtacctgtc caagcaagat cccgagggct ggggcaagtc    780
gcccggcttc ggcaccaccg tcgacttccc ggcggtgccg ggtgcgctgg gtgagaacgg    840
caacggcggc atggtgaccg gttgcgccga gacaccgggc tgcgtgggcct atatcggcat    900 cagcttcctc gaccaggcca gtcaacgggg actcggcgag gcccaactag gcaatagctc    960
tggcaatttc ttgttgcccg acgcgcaaag cattcaggcc gcggcggctg gcttcgcatc   1020

```
gaaaacccccg gcgaaccagg cgatttcgat gatcgacggg cccgccccgg acggctaccc    1080
gatcatcaac tacgagtacg ccatcgtcaa caaccggcaa aaggacgccg ccaccgcgca    1140
gaccttgcag gcatttctgc actgggcgat caccgacggc aacaaggcct cgttcctcga    1200
ccaggttcat ttccagccgc tgccgcccgc ggtggtgaag ttgtctgacg cgttgatcgc    1260
gacgatttcc agctagcctc gttgaccacc acgcgacagc aacctccgtc gggccatcgg    1320
gctgctttgc ggagcatgct ggcccgtgcc ggtgaagtcg gccgcgctgg cccggccatc    1380 cggtggtttgg gtgggatagg tgcggtgatc ccgctgcttg cgctggtctt ggtgctggtg    1440
gtgctggtca tcgaggcgat gggtgcgatc aggctcaacg ggttgcattt cttcaccgcc    1500
accgaatgga atccaggcaa cacctacggc gaaaccgttg tcaccgacgc gtcgcccatc    1560
cggtcggcgc ctactacggg gcgttgccgc tgatcgtcgg gacgctggcg acctcggcaa    1620
tcgccctgat catcgcggtg ccggtctctg taggagcggc gctggtgatc gtggaacggc    1680
tgccgaaacg gttggccgag gctgtgggaa tagtcctgga attgctcgcc ggaatcccca    1740
gcgtggtcgt cggtttgtgg ggggcaatga cgttcgggcc gttcatcgct catcacatcg    1800
ctccggtgat cgctcacaac gctcccgatg tgccggtgct gaactacttg gcggcgacc    1860 cgggcaacgg ggagggcatg ttggtgtccg gtctggtgtt ggcggtgatg gtcgttccca    1920
ttatcgccac caccactcat gacctgttcc ggcaggtgcc ggtgttgccc cgggagggcg    1980
cgatcgggaa ttc                                                        1993

<210> SEQ ID NO 39
<211> LENGTH: 374
<212> TYPE: PRT
<213> ORGANISM: Mycobacterium tuberculosis
<220> FEATURE:
<223> OTHER INFORMATION: 38 kD

<400> SEQUENCE: 39

Met Lys Ile Arg Leu His Thr Leu Leu Ala Val Leu Thr Ala Ala Pro
 1               5                  10                  15

Leu Leu Leu Ala Ala Ala Gly Cys Gly Ser Lys Pro Pro Ser Gly Ser
             20                  25                  30

Pro Glu Thr Gly Ala Gly Ala Gly Thr Val Ala Thr Pro Ala Ser
         35                  40                  45

Ser Pro Val Thr Leu Ala Glu Thr Gly Ser Thr Leu Leu Tyr Pro Leu
     50                  55                  60

Phe Asn Leu Trp Gly Pro Ala Phe His Glu Arg Tyr Pro Asn Val Thr
 65                  70                  75                  80

Ile Thr Ala Gln Gly Thr Gly Ser Gly Ala Gly Ile Ala Gln Ala Ala
                 85                  90                  95

Ala Gly Thr Val Asn Ile Gly Ala Ser Asp Ala Tyr Leu Ser Glu Gly
            100                 105                 110

Asp Met Ala Ala His Lys Gly Leu Met Asn Ile Ala Leu Ala Ile Ser
        115                 120                 125

Ala Gln Gln Val Asn Tyr Asn Leu Pro Gly Val Ser Glu His Leu Lys
    130                 135                 140

Leu Asn Gly Lys Val Leu Ala Ala Met Tyr Gln Gly Thr Ile Lys Thr
145                 150                 155                 160

Trp Asp Asp Pro Gln Ile Ala Ala Leu Asn Pro Gly Val Asn Leu Pro
                165                 170                 175

Gly Thr Ala Val Val Pro Leu His Arg Ser Asp Gly Ser Gly Asp Thr
            180                 185                 190
```

```
Phe Leu Phe Thr Gln Tyr Leu Ser Lys Gln Asp Pro Glu Gly Trp Gly
            195                 200                 205
Lys Ser Pro Gly Phe Gly Thr Thr Val Asp Phe Pro Ala Val Pro Gly
    210                 215                 220
Ala Leu Gly Glu Asn Gly Asn Gly Gly Met Val Thr Gly Cys Ala Glu
225                 230                 235                 240
Thr Pro Gly Cys Val Ala Tyr Ile Gly Ile Ser Phe Leu Asp Gln Ala
                245                 250                 255
Ser Gln Arg Gly Leu Gly Glu Ala Gln Leu Gly Asn Ser Ser Gly Asn
            260                 265                 270
Phe Leu Leu Pro Asp Ala Gln Ser Ile Gln Ala Ala Ala Ala Gly Phe
        275                 280                 285
Ala Ser Lys Thr Pro Ala Asn Gln Ala Ile Ser Met Ile Asp Gly Pro
    290                 295                 300
Ala Pro Asp Gly Tyr Pro Ile Ile Asn Tyr Glu Tyr Ala Ile Val Asn
305                 310                 315                 320
Asn Arg Gln Lys Asp Ala Ala Thr Ala Gln Thr Leu Gln Ala Phe Leu
                325                 330                 335
His Trp Ala Ile Thr Asp Gly Asn Lys Ala Ser Phe Leu Asp Gln Val
            340                 345                 350
His Phe Gln Pro Leu Pro Pro Ala Val Val Lys Leu Ser Asp Ala Leu
        355                 360                 365
Ile Ala Thr Ile Ser Ser
    370

<210> SEQ ID NO 40
<211> LENGTH: 999
<212> TYPE: DNA
<213> ORGANISM: Mycobacterium tuberculosis
<220> FEATURE:
<223> OTHER INFORMATION: DPEP

<400> SEQUENCE: 40
atgcatcacc atcaccatca catgcatcag gtggacccca acttgacacg tcgcaaggga      60
cgattggcgg cactggctat cgcggcgatg ccagcgcca gcctggtgac cgttgcggtg     120
cccgcgaccg ccaacgccga tccggagcca gcgcccccgg tacccacaac ggccgcctcg     180
ccgccgtcga ccgctgcagc gccacccgca ccggcgacac ctgttgcccc ccaccaccg     240
gccgccgcca acacgccgaa tgcccagccg ggcgatccca cgcagcaccc tccgccggcc     300
gacccgaacg caccgccgcc acctgtcatt gccccaaacg cacccccaacc tgtccggatc     360
gacaacccgg ttggaggatt cagcttcgcg ctgcctgctg ctggggtgga gtctgacgcc     420
gcccacttcg actacggttc agcactcctc agcaaaacca ccggggaccc gccatttccc     480
ggacagccgc cgccggtggc caatgacacc cgtatcgtgc tcggccggct agaccaaaag     540
ctttacgcca gcgccgaagc caccgactcc aaggccgcgg cccggttggg ctcggacatg     600
ggtgagttct atatgcccta cccgggcacc cggatcaacc aggaaaccgt ctcgctcgac     660
gccaacgggg tgtctggaag cgcgtcgtat tacgaagtca agttcagcga tccgagtaag     720
ccgaacggcc agatctggac gggcgtaatc ggctcgcccg cggcgaacgc accggacgcc     780
gggccccctc agcgctggtt tgtggtatgg ctcgggaccg ccaacaaccc ggtggacaag     840
ggcgcggcca aggcgctggc cgaatcgatc cggccttttgg tcgccccgcc gccggcgccg     900
gcaccggctc ctgcagagcc cgctccggcg cggcgccgg ccggggaagt cgctcctacc     960
ccgacgacac cgacaccgca gcggaccttac ccggcctga                          999
```

<210> SEQ ID NO 41
<211> LENGTH: 332
<212> TYPE: PRT
<213> ORGANISM: Mycobacterium tuberculosis
<220> FEATURE:
<223> OTHER INFORMATION: DPEP

<400> SEQUENCE: 41

Met His His His His His Met His Gln Val Asp Pro Asn Leu Thr
1               5                   10                  15

Arg Arg Lys Gly Arg Leu Ala Ala Leu Ala Ile Ala Ala Met Ala Ser
            20                  25                  30

Ala Ser Leu Val Thr Val Ala Val Pro Ala Thr Ala Asn Ala Asp Pro
        35                  40                  45

Glu Pro Ala Pro Pro Val Pro Thr Thr Ala Ala Ser Pro Pro Ser Thr
    50                  55                  60

Ala Ala Ala Pro Pro Ala Pro Ala Thr Pro Val Ala Pro Pro Pro
65                  70                  75                  80

Ala Ala Ala Asn Thr Pro Asn Ala Gln Pro Gly Asp Pro Asn Ala Ala
                85                  90                  95

Pro Pro Pro Ala Asp Pro Asn Ala Pro Pro Pro Val Ile Ala Pro
            100                 105                 110

Asn Ala Pro Gln Pro Val Arg Ile Asp Asn Pro Val Gly Gly Phe Ser
        115                 120                 125

Phe Ala Leu Pro Ala Gly Trp Val Glu Ser Asp Ala Ala His Phe Asp
    130                 135                 140

Tyr Gly Ser Ala Leu Leu Ser Lys Thr Thr Gly Asp Pro Pro Phe Pro
145                 150                 155                 160

Gly Gln Pro Pro Pro Val Ala Asn Asp Thr Arg Ile Val Leu Gly Arg
                165                 170                 175

Leu Asp Gln Lys Leu Tyr Ala Ser Ala Glu Ala Thr Asp Ser Lys Ala
            180                 185                 190

Ala Ala Arg Leu Gly Ser Asp Met Gly Glu Phe Tyr Met Pro Tyr Pro
        195                 200                 205

Gly Thr Arg Ile Asn Gln Glu Thr Val Ser Leu Asp Ala Asn Gly Val
    210                 215                 220

Ser Gly Ser Ala Ser Tyr Tyr Glu Val Lys Phe Ser Asp Pro Ser Lys
225                 230                 235                 240

Pro Asn Gly Gln Ile Trp Thr Gly Val Ile Gly Ser Pro Ala Ala Asn
                245                 250                 255

Ala Pro Asp Ala Gly Pro Pro Gln Arg Trp Phe Val Val Trp Leu Gly
            260                 265                 270

Thr Ala Asn Asn Pro Val Asp Lys Gly Ala Ala Lys Ala Leu Ala Glu
        275                 280                 285

Ser Ile Arg Pro Leu Val Ala Pro Pro Ala Pro Ala Pro Ala Pro
    290                 295                 300

Ala Glu Pro Ala Pro Ala Pro Ala Pro Ala Gly Glu Val Ala Pro Thr
305                 310                 315                 320

Pro Thr Thr Pro Thr Pro Gln Arg Thr Leu Pro Ala
                325                 330

<210> SEQ ID NO 42
<211> LENGTH: 702
<212> TYPE: DNA
<213> ORGANISM: Mycobacterium tuberculosis
<220> FEATURE:

```
<223> OTHER INFORMATION: TbH4
<220> FEATURE:
<221> NAME/KEY: modified_base
<222> LOCATION: (1)..(702)
<223> OTHER INFORMATION: n = g, a, c or t

<400> SEQUENCE: 42
cggcacgagg atcggtaccc cgcggcatcg gcagctgccg attcgccggg tttccccacc    60
cgaggaaagc cgctaccaga tggcgctgcc gaagtagggc gatccgttcg cgatgccggc   120
atgaacgggc ggcatcaaat tagtgcagga acctttcagt ttagcgacga taatggctat   180
agcactaagg aggatgatcc gatatgacgc agtcgcagac cgtgacggtg atcagcaag    240
agattttgaa cagggccaac gaggtggagg ccccgatggc ggacccaccg actgatgtcc   300
ccatcacacc gtgcgaactc acggnggnta aaaacgccgc caacagntg gtnttgtccg    360
ccgacaacat gcgggaatac ctggcggccg gtgccaaaga gcggcagcgt ctggcgacct   420
cgctgcgcaa cgcggccaag gngtatggcg aggttgatga ggaggctgcg accgcgctgg   480
acaacgacgg cgaaggaact gtgcaggcag aatcggccgg ggccgtcgga ggggacagtt   540
cggccgaact aaccgatacg ccgagggtgg ccacggccgg tgaacccaac ttcatggatc   600
tcaaagaagc ggcaaggaag ctcgaaacgg gcgaccaagg cgcatcgctc gcgcactgng   660
gggatgggtg gaacacttnc accctgacgc tgcaaggcga cg                     702

<210> SEQ ID NO 43
<211> LENGTH: 286
<212> TYPE: PRT
<213> ORGANISM: Mycobacterium tuberculosis
<220> FEATURE:
<223> OTHER INFORMATION: TbH4
<220> FEATURE:
<221> NAME/KEY: MOD_RES
<222> LOCATION: (1)..(286)
<223> OTHER INFORMATION: Xaa = any amino acid

<400> SEQUENCE: 43

Gly Asp Ser Phe Trp Ala Ala Asp Gln Met Ala Arg Gly Phe Val
  1               5                  10                  15

Leu Gly Ala Thr Ala Gly Arg Thr Thr Leu Thr Gly Glu Gly Leu Gln
                 20                  25                  30

His Ala Asp Gly His Ser Leu Leu Leu Asp Ala Thr Asn Pro Ala Val
             35                  40                  45

Val Ala Tyr Asp Pro Ala Phe Ala Tyr Glu Ile Gly Tyr Ile Xaa Glu
         50                  55                  60

Ser Gly Leu Ala Arg Met Cys Gly Glu Asn Pro Glu Asn Ile Phe Phe
 65                  70                  75                  80

Tyr Ile Thr Val Tyr Asn Glu Pro Tyr Val Gln Pro Pro Glu Pro Glu
                 85                  90                  95

Asn Phe Asp Pro Glu Gly Val Leu Gly Gly Ile Tyr Arg Tyr His Ala
            100                 105                 110

Ala Thr Glu Gln Arg Thr Asn Lys Xaa Gln Ile Leu Ala Ser Gly Val
        115                 120                 125

Ala Met Pro Ala Ala Leu Arg Ala Ala Gln Met Leu Ala Ala Glu Trp
    130                 135                 140

Asp Val Ala Ala Asp Val Trp Ser Val Thr Ser Trp Gly Glu Leu Asn
145                 150                 155                 160

Arg Asp Gly Val Val Ile Glu Thr Glu Lys Leu Arg His Pro Asp Arg
                165                 170                 175

Pro Ala Gly Val Pro Tyr Val Thr Arg Ala Leu Glu Asn Ala Arg Gly
```

```
                        180                 185                 190
Pro Val Ile Ala Val Ser Asp Trp Met Arg Ala Val Pro Glu Gln Ile
            195                 200                 205
Arg Pro Trp Val Pro Gly Thr Tyr Leu Thr Leu Gly Thr Asp Gly Phe
        210                 215                 220
Gly Phe Ser Asp Thr Arg Pro Ala Gly Arg Arg Tyr Phe Asn Thr Asp
225                 230                 235                 240
Ala Glu Ser Gln Val Gly Arg Gly Phe Arg Gly Trp Pro Gly Arg
                245                 250                 255
Arg Val Asn Ile Asp Pro Phe Gly Ala Gly Arg Gly Pro Pro Ala Gln
            260                 265                 270
Leu Pro Gly Phe Asp Glu Gly Gly Leu Arg Pro Xaa Lys
        275                 280                 285

<210> SEQ ID NO 44
<211> LENGTH: 339
<212> TYPE: DNA
<213> ORGANISM: Mycobacterium tuberculosis
<220> FEATURE:
<223> OTHER INFORMATION: DPPD genomic DNA

<400> SEQUENCE: 44
atgaagttga agtttgctcg cctgagtact gcgatactgg gttgtgcagc ggcgcttgtg      60
tttcctgcct cggttgccag cgcagatcca cctgacccgc atcagccgga catgacgaaa     120
ggctattgcc cggtggccg atggggtttt ggcgacttgg ccgtgtgcga cggcgagaag     180
taccccgacg gctcgttttg gcaccagtgg atgcaaacgt ggtttaccgg cccacagttt     240
tacttcgatt gtgtcagcgg cggtgagccc ctccccggcc cgccgccacc gggtggttgc     300
ggtggggcaa ttccgtccga gcagcccaac gctccctga                           339

<210> SEQ ID NO 45
<211> LENGTH: 112
<212> TYPE: PRT
<213> ORGANISM: Mycobacterium tuberculosis
<220> FEATURE:
<223> OTHER INFORMATION: DPPD

<400> SEQUENCE: 45

Met Lys Leu Lys Phe Ala Arg Leu Ser Thr Ala Ile Leu Gly Cys Ala
1               5                   10                  15
Ala Ala Leu Val Phe Pro Ala Ser Val Ala Ser Ala Asp Pro Pro Asp
            20                  25                  30
Pro His Gln Pro Asp Met Thr Lys Gly Tyr Cys Pro Gly Gly Arg Trp
        35                  40                  45
Gly Phe Gly Asp Leu Ala Val Cys Asp Gly Glu Lys Tyr Pro Asp Gly
    50                  55                  60
Ser Phe Trp His Gln Trp Met Gln Thr Trp Phe Thr Gly Pro Gln Phe
65                  70                  75                  80
Tyr Phe Asp Cys Val Ser Gly Gly Glu Pro Leu Pro Gly Pro Pro Pro
                85                  90                  95
Pro Gly Gly Cys Gly Gly Ala Ile Pro Ser Glu Gln Pro Asn Ala Pro
            100                 105                 110

<210> SEQ ID NO 46
<211> LENGTH: 921
<212> TYPE: DNA
<213> ORGANISM: Artificial Sequence
<220> FEATURE:
<223> OTHER INFORMATION: Description of Artificial Sequence:tri-fusion
``` protein DPV-MTI-MSL (designated MTb31F) cDNA
<220> FEATURE:
<221> NAME/KEY: CDS
<222> LOCATION: (1)..(900)
<223> OTHER INFORMATION: MTb31F

<400> SEQUENCE: 46

```
cat atg cat cac cat cac cat cac gat ccc gtg gac gcg gtc att aac      48
His Met His His His His His His Asp Pro Val Asp Ala Val Ile Asn
 1               5

```
            cac act ggc ggc cgc tcg agc aga tcc ggc tgc taa caaagcccga        910
            His Thr Gly Gly Arg Ser Ser Arg Ser Gly Cys
                290                 295 aaggaagctg a                                                                  921
```

<210> SEQ ID NO 47
<211> LENGTH: 299
<212> TYPE: PRT
<213> ORGANISM: Artificial Sequence
<220> FEATURE:
<223> OTHER INFORMATION: Description of Artificial Sequence:tri-fusion
      protein DPV-MTI-MSL (designated MTb31F) cDNA

<400> SEQUENCE: 47

<223> OTHER INFORMATION: Description of Artificial Sequence:tetra-fusion
    protein DPV-MTI-MSL-MTC

```
gat ttc ggg ctt tta cct ccg gaa gtg aat tca agc cga atg tat tcc    912
Asp Phe Gly Leu Leu Pro Pro Glu Val Asn Ser Ser Arg Met Tyr Ser
    290                 295                 300 ggt ccg ggg ccg gag tcg atg cta gcc gcc gcg gcc tgg gac ggt        960
Gly Pro Gly Pro Glu Ser Met Leu Ala Ala Ala Ala Trp Asp Gly
305                 310                 315                 320 gtg gcc gcg gag ttg act tcc gcc gcg gtc tcg tat gga tcg gtg gtg   1008
Val Ala Ala Glu Leu Thr Ser Ala Ala Val Ser Tyr Gly Ser Val Val
                325                 330                 335 tcg acg ctg atc gtt gag ccg tgg atg ggg ccg gcg gcg gcc gcg atg   1056
Ser Thr Leu Ile Val Glu Pro Trp Met Gly Pro Ala Ala Ala Ala Met
            340                 345                 350 gcg gcc gcg gca acg ccg tat gtg ggg tgg ctg gcc gcc acg gcg gcg   1104
Ala Ala Ala Ala Thr Pro Tyr Val Gly Trp Leu Ala Ala Thr Ala Ala
355                 360                 365 ctg gcg aag gag acg gcc aca cag gcg agg gca gcg gaa gcg ttt       1152
Leu Ala Lys Glu Thr Ala Thr Gln Ala Arg Ala Ala Glu Ala Phe
    370                 375                 380 ggg acg gcg ttc gcg atg acg gtg cca cca tcc ctc gtc gcg gcc aac   1200
Gly Thr Ala Phe Ala Met Thr Val Pro Pro Ser Leu Val Ala Ala Asn
385                 390                 395                 400 cgc agc cgg ttg atg tcg ctg gtc gcg gcg aac att ctg ggg caa aac   1248
Arg Ser Arg Leu Met Ser Leu Val Ala Ala Asn Ile Leu Gly Gln Asn
                405                 410                 415 agt gcg gcg atc gcg gct acc cag gcc gag tat gcc gaa atg tgg gcc   1296
Ser Ala Ala Ile Ala Ala Thr Gln Ala Glu Tyr Ala Glu Met Trp Ala
            420                 425                 430 caa gac gct gcc gtg atg tac agc tat gag ggg gca tct gcg gcc gcg   1344
Gln Asp Ala Ala Val Met Tyr Ser Tyr Glu Gly Ala Ser Ala Ala Ala
        435                 440                 445 tcg gcg ttg ccg ccg ttc act cca ccc gtg caa ggc acc ggc ccg gcc   1392
Ser Ala Leu Pro Pro Phe Thr Pro Pro Val Gln Gly Thr Gly Pro Ala
450                 455                 460 ggg ccc gcg gcc gca gcc gcg gcg acc caa gcc gcc ggt gcg ggc gcc   1440
Gly Pro Ala Ala Ala Ala Ala Ala Thr Gln Ala Ala Gly Ala Gly Ala
465                 470                 475                 480 gtt gcg gat gca cag gcg aca ctg gcc cag ctg ccc ccg ggg atc ctg   1488
Val Ala Asp Ala Gln Ala Thr Leu Ala Gln Leu Pro Pro Gly Ile Leu
                485                 490                 495 agc gac att ctg tcc gca ttg gcc gcc aac gct gat ccg ctg aca tcg   1536
Ser Asp Ile Leu Ser Ala Leu Ala Ala Asn Ala Asp Pro Leu Thr Ser
            500                 505                 510 gga ctg ttg ggg atc gcg tcg acc ctc aac ccg caa gtc gga tcc gct   1584
Gly Leu Leu Gly Ile Ala Ser Thr Leu Asn Pro Gln Val Gly Ser Ala
        515                 520                 525 cag ccg ata gtg atc ccc acc ccg ata ggg gaa ttg gac gtg atc gcg   1632
Gln Pro Ile Val Ile Pro Thr Pro Ile Gly Glu Leu Asp Val Ile Ala
530                 535                 540 ctc tac att gca tcc atc gcg acc ggc agc att gcg ctc gcg atc acg   1680
Leu Tyr Ile Ala Ser Ile Ala Thr Gly Ser Ile Ala Leu Ala Ile Thr
545                 550                 555                 560 aac acg gcc aga ccc tgg cac atc ggc cta tac ggg aac gcc ggc ggg   1728
Asn Thr Ala Arg Pro Trp His Ile Gly Leu Tyr Gly Asn Ala Gly Gly
                565                 570                 575 ctg gga ccg acg cag ggc cat cca ctg agt tcg gcg acc gac gag ccg   1776
Leu Gly Pro Thr Gln Gly His Pro Leu Ser Ser Ala Thr Asp Glu Pro
            580                 585                 590 gag ccg cac tgg ggc ccc ttc ggg ggc gcg gcg ccg gtg tcc gcg ggc   1824
Glu Pro His Trp Gly Pro Phe Gly Gly Ala Ala Pro Val Ser Ala Gly
        595                 600                 605
```

```
gtc ggc cac gca gca tta gtc gga gcg ttg tcg gtg ccg cac agc tgg    1872
Val Gly His Ala Ala Leu Val Gly Ala Leu Ser Val Pro His Ser Trp
            610             615             620 acc acg gcc gcc ccg gag atc cag ctc gcc gtt cag gca aca ccc acc    1920
Thr Thr Ala Ala Pro Glu Ile Gln Leu Ala Val Gln Ala Thr Pro Thr
625             630             635             640 ttc agc tcc agc gcc ggc gcc gac ccg acg gcc cta aac ggg atg ccg    1968
Phe Ser Ser Ser Ala Gly Ala Asp Pro Thr Ala Leu Asn Gly Met Pro
                645             650             655 gca ggc ctg ctc agc ggg atg gct ttg gcg agc ctg gcc gca cgc ggc    2016
Ala Gly Leu Leu Ser Gly Met Ala Leu Ala Ser Leu Ala Ala Arg Gly
            660             665             670 acg acg ggc ggt ggc ggc acc cgt agc ggc acc agc act gac ggc caa    2064
Thr Thr Gly Gly Gly Gly Thr Arg Ser Gly Thr Ser Thr Asp Gly Gln
    675             680             685 gag gac ggc cgc aaa ccc ccg gta gtt gtg att aga gag cag ccg ccg    2112
Glu Asp Gly Arg Lys Pro Pro Val Val Val Ile Arg Glu Gln Pro Pro
690             695             700 ccc gga aac ccc ccg cgg taa gatttctaaa tccatcacac tggcggccgc       2163
Pro Gly Asn Pro Pro Arg
705             710 tcgag                                                              2168

<210> SEQ ID NO 49
<211> LENGTH: 710
<212> TYPE: PRT
<213> ORGANISM: Artificial Sequence
<220> FEATURE:
<223> OTHER INFORMATION: Description of Artificial Sequence:tetra-fusion
      protein DPV-MTI-MSL-MTCC#2 (designated MTb71F)

<400> SEQUENCE: 49

His Met His His His His His His Asp Pro Val Asp Ala Val Ile Asn
  1               5                  10                  15

Thr Thr Cys Asn Tyr Gly Gln Val Val Ala Ala Leu Asn Ala Thr Asp
                 20                  25                  30

Pro Gly Ala Ala Ala Gln Phe Asn Ala Ser Pro Val Ala Gln Ser Tyr
             35                  40                  45

Leu Arg Asn Phe Leu Ala Ala Pro Pro Pro Gln Arg Ala Ala Met Ala
         50                  55                  60

Ala Gln Leu Gln Ala Val Pro Gly Ala Ala Gln Tyr Ile Gly Leu Val
 65                  70                  75                  80

Glu Ser Val Ala Gly Ser Cys Asn Asn Tyr Glu Leu Met Thr Ile Asn
                 85                  90                  95

Tyr Gln Phe Gly Asp Val Asp Ala His Gly Ala Met Ile Arg Ala Gln
            100                 105                 110

Ala Ala Ser Leu Glu Ala Glu His Gln Ala Ile Val Arg Asp Val Leu
        115                 120                 125

Ala Ala Gly Asp Phe Trp Gly Gly Ala Gly Ser Val Ala Cys Gln Glu
    130                 135                 140

Phe Ile Thr Gln Leu Gly Arg Asn Phe Gln Val Ile Tyr Glu Gln Ala
145                 150                 155                 160

Asn Ala His Gly Gln Lys Val Gln Ala Ala Gly Asn Asn Met Ala Gln
                165                 170                 175

Thr Asp Ser Ala Val Gly Ser Ser Trp Ala Thr Ser Met Ser Leu Leu
            180                 185                 190

Asp Ala His Ile Pro Gln Leu Val Ala Ser Gln Ser Ala Phe Ala Ala
        195                 200                 205
```

```
Lys Ala Gly Leu Met Arg His Thr Ile Gly Gln Ala Glu Gln Ala Ala
    210                 215                 220

Met Ser Ala Gln Ala Phe His Gln Gly Glu Ser Ser Ala Ala Phe Gln
225                 230                 235                 240

Ala Ala His Ala Arg Phe Val Ala Ala Ala Lys Val Asn Thr Leu
                245                 250                 255

Leu Asp Val Ala Gln Ala Asn Leu Gly Glu Ala Ala Gly Thr Tyr Val
            260                 265                 270

Ala Ala Asp Ala Ala Ala Ser Thr Tyr Thr Gly Phe Asp Ile Met
            275                 280                 285

Asp Phe Gly Leu Leu Pro Pro Glu Val Asn Ser Ser Arg Met Tyr Ser
        290                 295                 300

Gly Pro Gly Pro Glu Ser Met Leu Ala Ala Ala Ala Trp Asp Gly
305                 310                 315                 320

Val Ala Ala Glu Leu Thr Ser Ala Ala Val Ser Tyr Gly Ser Val Val
                325                 330                 335

Ser Thr Leu Ile Val Glu Pro Trp Met Gly Pro Ala Ala Ala Ala Met
            340                 345                 350

Ala Ala Ala Ala Thr Pro Tyr Val Gly Trp Leu Ala Ala Thr Ala Ala
            355                 360                 365

Leu Ala Lys Glu Thr Ala Thr Gln Ala Arg Ala Ala Glu Ala Phe
    370                 375                 380

Gly Thr Ala Phe Ala Met Thr Val Pro Pro Ser Leu Val Ala Ala Asn
385                 390                 395                 400

Arg Ser Arg Leu Met Ser Leu Val Ala Ala Asn Ile Leu Gly Gln Asn
                405                 410                 415

Ser Ala Ala Ile Ala Ala Thr Gln Ala Glu Tyr Ala Glu Met Trp Ala
            420                 425                 430

Gln Asp Ala Ala Val Met Tyr Ser Tyr Glu Gly Ala Ser Ala Ala Ala
    435                 440                 445

Ser Ala Leu Pro Pro Phe Thr Pro Pro Val Gln Gly Thr Gly Pro Ala
    450                 455                 460

Gly Pro Ala Ala Ala Ala Ala Thr Gln Ala Ala Gly Ala Gly Ala
465                 470                 475                 480

Val Ala Asp Ala Gln Ala Thr Leu Ala Gln Leu Pro Pro Gly Ile Leu
                485                 490                 495

Ser Asp Ile Leu Ser Ala Leu Ala Ala Asn Ala Asp Pro Leu Thr Ser
            500                 505                 510

Gly Leu Leu Gly Ile Ala Ser Thr Leu Asn Pro Gln Val Gly Ser Ala
    515                 520                 525

Gln Pro Ile Val Ile Pro Thr Pro Ile Gly Glu Leu Asp Val Ile Ala
    530                 535                 540

Leu Tyr Ile Ala Ser Ile Ala Thr Gly Ser Ile Ala Leu Ala Ile Thr
545                 550                 555                 560

Asn Thr Ala Arg Pro Trp His Ile Gly Leu Tyr Gly Asn Ala Gly Gly
                565                 570                 575

Leu Gly Pro Thr Gln Gly His Pro Leu Ser Ser Ala Thr Asp Glu Pro
        580                 585                 590

Glu Pro His Trp Gly Pro Phe Gly Gly Ala Ala Pro Val Ser Ala Gly
            595                 600                 605

Val Gly His Ala Ala Leu Val Gly Ala Leu Ser Val Pro His Ser Trp
    610                 615                 620

Thr Thr Ala Ala Pro Glu Ile Gln Leu Ala Val Gln Ala Thr Pro Thr
```

-continued

```
                625                 630                 635                 640
        Phe Ser Ser Ala Gly Ala Asp Pro Thr Ala Leu Asn Gly Met Pro
                        645                 650                 655

Ala Gly Leu Leu Ser Gly Met Ala Leu Ala Ser Leu Ala Ala Arg Gly
                        660                 665                 670

Thr Thr Gly Gly Gly Gly Thr Arg Ser Gly Thr Ser Thr Asp Gly Gln
                    675                 680                 685

Glu Asp Gly Arg Lys Pro Pro Val Val Val Ile Arg Glu Gln Pro Pro
                690                 695                 700

Pro Gly Asn Pro Pro Arg
        705                 710

<210> SEQ ID NO 50
<211> LENGTH: 588
<212> TYPE: DNA
<213> ORGANISM: Mycobacterium tuberculosis
<220> FEATURE:
<223> OTHER INFORMATION: Ra35 N-terminus of MTB32A (Ra35FL)

<400> SEQUENCE: 50
gccccgccgg ccttgtcgca ggaccggttc gccgacttcc ccgcgctgcc cctcgacccg         60
tccgcgatgg tcgcccaagt ggggccacag gtggtcaaca tcaacaccaa actgggctac       120
aacaacgccg tgggcgccgg gaccggcatc gtcatcgatc ccaacggtgt cgtgctgacc       180
aacaaccacg tgatcgcggg cgccaccgac atcaatgcgt tcagcgtcgg ctccggccaa       240
acctacggcg tcgatgtggt cgggtatgac cgcacccagg atgtcgcggt gctgcagctg       300
cgcggtgccg gtggcctgcc gtcggcggcg atcggtggcg gcgtcgcggt tggtgagccc       360
gtcgtcgcga tgggcaacag cggtgggcag ggcggaacgc cccgtgcggt gcctggcagg       420
gtggtcgcgc tcggccaaac cgtgcaggcg tcggattcgc tgaccggtgc cgaagagaca       480
ttgaacgggt tgatccagtt cgatgccgcg atccagcccg gtgaggcggg cgggcccgtc       540
gtcaacggcc taggacaggt ggtcggtatg aacacggccg cgtcctag                    588
```